US010393726B2

(12) United States Patent
Soper et al.

(10) Patent No.: US 10,393,726 B2
(45) Date of Patent: Aug. 27, 2019

(54) UNIVERSAL MOLECULAR PROCESSOR FOR PRECISION MEDICINE

(71) Applicants: The University of North Carolina at Chapel Hill, Chapel Hill, NC (US); Cornell University, Ithaca, NY (US); Board of Supervisors of Louisiana State University and Agricultural and Mechanical College, Baton Rouge, LA (US)

(72) Inventors: Steven A. Soper, Baton Rouge, LA (US); Francis Barany, New York, NY (US); Sunggook Park, Baton Rouge, LA (US); Michael Murphy, Baton Rouge, LA (US); Collin J. McKinney, Durham, NC (US); John William Efcavitch, San Carlos, CA (US); Mateusz Hupert, Chapel Hill, NC (US)

(73) Assignees: The University of North Carolina at Chapel Hill, Chapel Hill, NC (US); Cornell University, Ithaca, NY (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/560,028

(22) PCT Filed: Mar. 23, 2016

(86) PCT No.: PCT/US2016/023769
§ 371 (c)(1),
(2) Date: Sep. 20, 2017

(87) PCT Pub. No.: WO2016/154302
PCT Pub. Date: Sep. 29, 2016

(65) Prior Publication Data
US 2018/0074039 A1    Mar. 15, 2018

Related U.S. Application Data

(60) Provisional application No. 62/137,028, filed on Mar. 23, 2015.

(51) Int. Cl.
*G01N 33/487* (2006.01)
*C12M 1/40* (2006.01)
(Continued)

(52) U.S. Cl.
CPC ...... *G01N 33/48721* (2013.01); *B01L 3/5027* (2013.01); *B01L 3/502753* (2013.01);
(Continued)

(58) Field of Classification Search
CPC .............................. C12Q 1/6869; C12M 1/40
See application file for complete search history.

(56) References Cited

U.S. PATENT DOCUMENTS 8,586,301 B2    11/2013   Kokoris et al.
8,652,779 B2    2/2014    Turner et al.
(Continued)

FOREIGN PATENT DOCUMENTS

DE    10 2011 081 472 A1    2/2013
WO    2012170560               12/2012
(Continued)

OTHER PUBLICATIONS

Satake et al , A sensor for blood cell counter using MEMS technology, 2002, Sensors and Actuators B, 83, 77-81. (Year: 2002).*
(Continued)

*Primary Examiner* — Narayan K Bhat
(74) *Attorney, Agent, or Firm* — Myers Bigel, P.A.

(57) ABSTRACT

The present invention is directed to a device that comprises a biomolecular processor and one or more nanotubes. Each biomolecular processor comprises a bioreactor chamber defined by a solid substrate, a plurality of spaced support structures within said bioreactor chamber and attached to the solid substrate, and one or more capture molecules immobilized to some or all of said plurality of spaced support structures, said one or more capture molecules suitable to bind to a portion of a target nucleic acid molecule in a sample. The device also comprises one or more nanotubes defined by the solid substrate and fluidically coupled to the bioreactor chamber.

7 Claims, 66 Drawing Sheets

(51) Int. Cl.
| | |
|---|---|
| B01L 3/00 | (2006.01) |
| C12M 3/06 | (2006.01) |
| C12Q 1/6806 | (2018.01) |
| C12Q 1/6869 | (2018.01) |
| C12Q 1/6837 | (2018.01) |
| C12Q 1/6874 | (2018.01) |

(52) U.S. Cl.
CPC ......... *B01L 3/502761* (2013.01); *C12M 1/40* (2013.01); *C12M 23/16* (2013.01); *C12Q 1/6806* (2013.01); *C12Q 1/6869* (2013.01); *B01L 3/502715* (2013.01); *B01L 2200/0647* (2013.01); *B01L 2300/0645* (2013.01); *B01L 2300/0861* (2013.01); *B01L 2300/0896* (2013.01); *C12Q 1/6837* (2013.01); *C12Q 1/6874* (2013.01)

(56) References Cited

U.S. PATENT DOCUMENTS

| | | | |
|---|---|---|---|
| 8,889,348 | B2 | 11/2014 | Ju |
| 8,975,095 | B2 | 3/2015 | Han et al. |
| 2007/0237680 | A1* | 10/2007 | Lee ................. C12M 47/02 422/83 |
| 2010/0291548 | A1 | 11/2010 | Sharaf et al. |
| 2010/0297709 | A1 | 11/2010 | Rashtchian |
| 2010/0331194 | A1 | 12/2010 | Turner et al. |
| 2011/0011781 | A1* | 1/2011 | Blankenstein .... B01L 3/502715 210/205 |
| 2012/0080361 | A1 | 4/2012 | Walavalkar et al. |
| 2012/0100521 | A1 | 4/2012 | Soper et al. |
| 2012/0157344 | A1 | 6/2012 | Rosenfeld et al. |
| 2012/0164651 | A1 | 6/2012 | Kazakov et al. |
| 2012/0220047 | A1* | 8/2012 | Seifried ............ B01L 3/502753 436/178 |
| 2012/0237997 | A1 | 9/2012 | Koser |
| 2013/0022977 | A1 | 1/2013 | Lapidus et al. |
| 2013/0244313 | A1 | 9/2013 | Dunn et al. |
| 2013/0327644 | A1 | 12/2013 | Turner et al. |
| 2014/0134646 | A1 | 5/2014 | Martin et al. |
| 2014/0179909 | A1 | 6/2014 | O'Halloran et al. |
| 2016/0161378 | A1* | 6/2016 | Kim ..................... G01N 1/4077 422/527 |

FOREIGN PATENT DOCUMENTS

| | | |
|---|---|---|
| WO | WO 2013/012440 A2 | 1/2013 |
| WO | WO 2013/160408 A2 | 10/2013 |
| WO | WO 2013/191793 A1 | 12/2013 |
| WO | WO 2014/124365 A2 | 8/2014 |
| WO | WO 2014/160199 A1 | 10/2014 |
| WO | 2016154337 | 9/2016 |

OTHER PUBLICATIONS

Machine translation in English of Description DE102011081472, printed on Nov. 7, 2018, pp. 1-20. (Year: 2018).*
Machine translation in English of Claims DE102011081472, printed on Nov. 7, 2018, pp. 1-2. (Year: 2018).*
Partial Supplementary European Search Report corresponding to European Patent Application No. 16769605.3 (8 pages) (dated Sep. 4, 2018).
U.S. Appl. No. 15/560,805, Barany et al., filed Sep. 22, 2017.
Ashton et al. "MinION nanopore sequencing identifies position and structure of a bacterial antibiotic resistance island" *Nature Biotechnology* 33:296-300 (2015).
Atas et al. "DNA sequencing and bar-coding using solid-state nanopores" *Electrophoresis* 33:3437-3447 (2012).
Brown et al. "Novel, Gasketless, Interconnect Using Parallel Superhydrophobic Surfaces for Modular Microfluidic Systems" *Proceedings of the ASME 2011 International Mechanical Engineering Congress & Exposition* (5 pages) (2011).
Cherf et al. "Automated forward and reverse ratcheting of DNA in a nanopore at 5-Å precision" *Nature Biotechnology* 30(4):344-348 (2012).
Hernandez-Ainsa et al. "DNA Origami Nanopores for Controlling DNA Translocation" *ACS Nano* 7(7):6024-6030 (2013).
Kant et al. "The Influence of Nanopore Dimensions on the Electrochemical Properties of Nanopore Arrays Studied by Impedance Spectroscopy" *Sensors* 14:21316-21328 (2014).
Kumar et al. "PEG-Labeled Nucleotides and Nanopore Detection for Single Molecule DNA Sequencing by Synthesis" *Scientific Reports* 2(684):1-8 (2012).
Langecker et al. "Electrophoretic Time-of-Flight Measurements of Single DNA Molecules with Two Stacked Nanopores" *Nano Letters* 11:5002-5007 (2011).
Laszlo et al. "Nanopore sequencing of the phi X 174 genome" *arXiv* 1406(4214) (39 pages) (2014).
Lee et al. "Single-molecule DNA digestion in various alkanethiol-functionalized gold nanopores" *Talanta* 107:297-303 (2013).
Manrao et al. "Reading DNA at single-nucleotide resolution with a mutant MspA nanopore and phi29 DNA polymerase" *Nature Biotechnology* 30(4):349-354 (2012).
Matthews, Jerney M.A. "Nanopore DNA sequencing inches closer to commercial debut" *Physics Today* 65:29-31 (2012).
Pennisi, Elizabeth "Search for Pore-fection" *Science* 336:534-537 (2012).
Quick et al. "Real-time, portable genome sequencing for Ebola surveillance" *Nature* 530:228-232 (2016).
Saleh et al. "An Artificial Nanopore for Molecular Sensing" *Nano Letters* 3(1):37-38 (2003).
Steinbock et al. "The emergence of nanopores in next-generation sequencing" *Nanotechnology* 25:1-5 (2015).
Venta et al. "Differentiation of Short, Single-Stranded DNA Homopolymers in Solid-State Nanopores" *ACS Nano* 7(5):4629-4636 (2013).
Wang et al. "The evolution of nanopore sequencing" *Frontiers in Genetics* 5:1-20 (2015).
Zhang et al. "Programming Nanopore Ion Flow for Encoded Multiplex MicroRNA Detection" *ACS Nano* 8(4):3444-3450 (2014).
International Search Report and the Written Opinion of the International Searching Authority corresponding to International Patent Application No. PCT/US2016/023769 (20 pages) (dated Jul. 21, 2016).
Murphy et al. "Technology for Modular Microfluidic Systems" Louisiana State University's Center for Biomodular Multi-Scale Systems Presentation (43 pages) (Dec. 17, 2012).

* cited by examiner

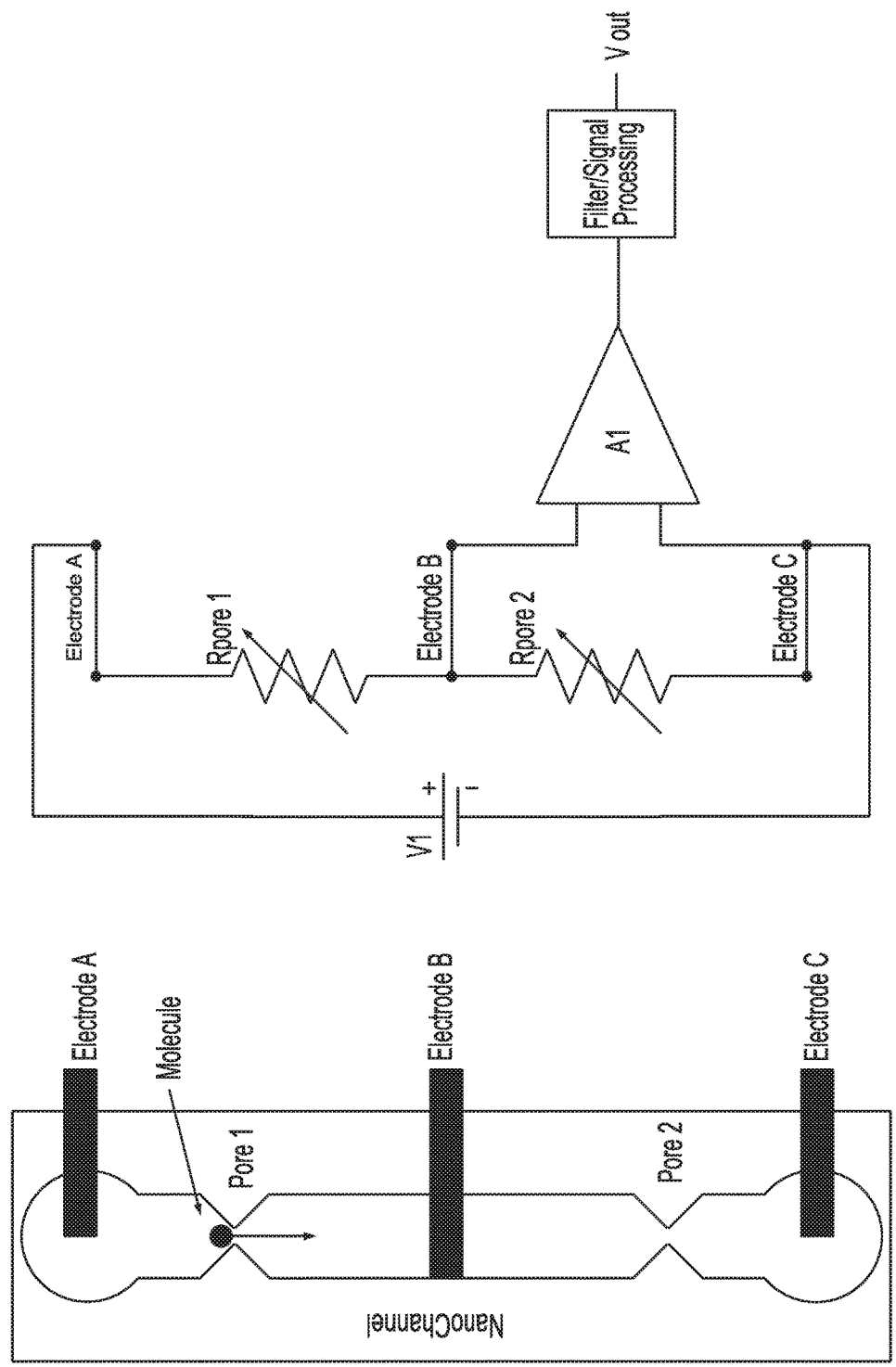

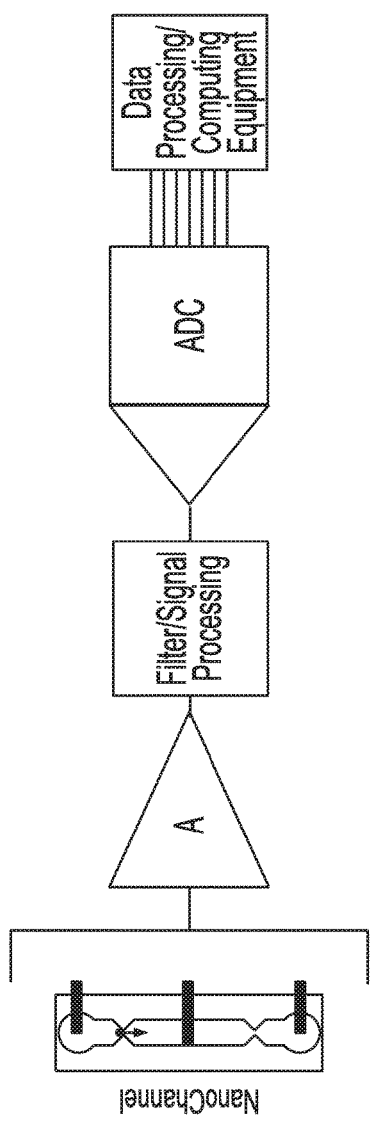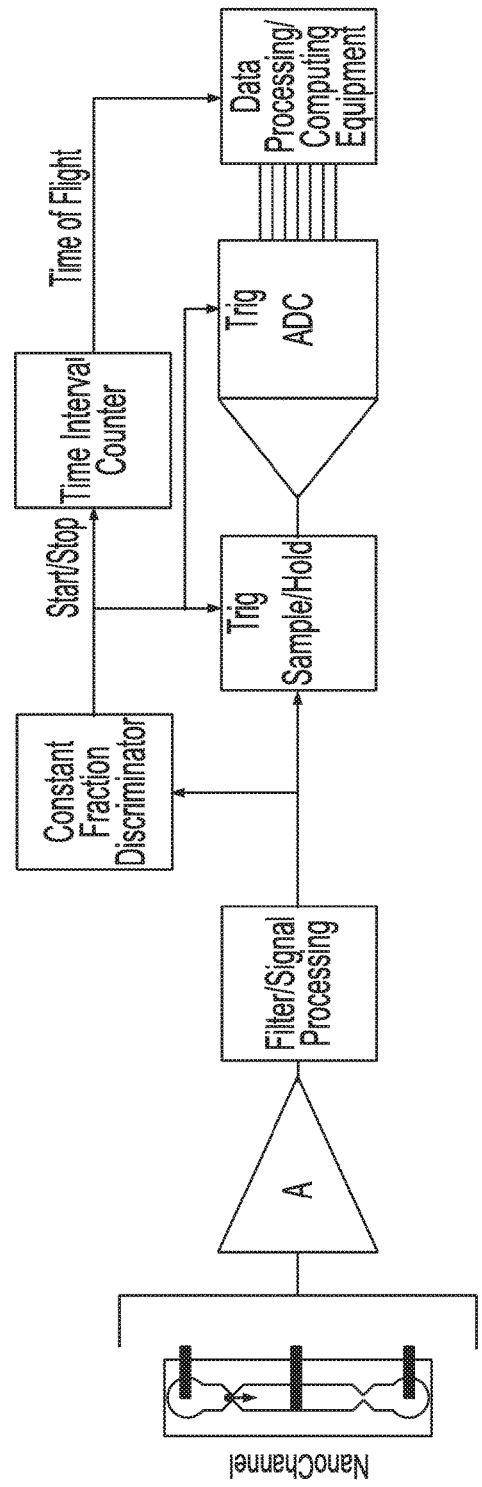
FIG. 15A
FIG. 15B

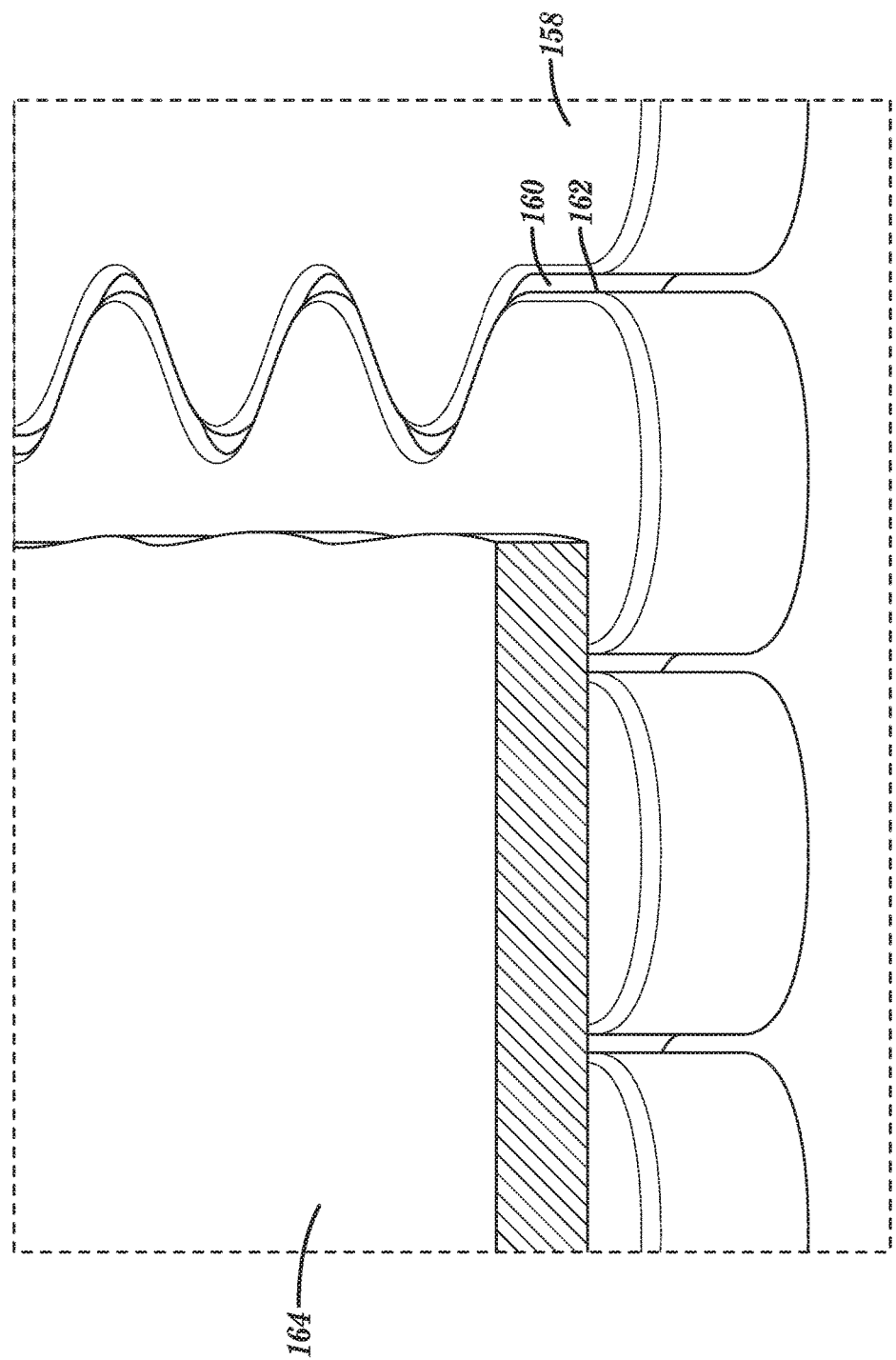

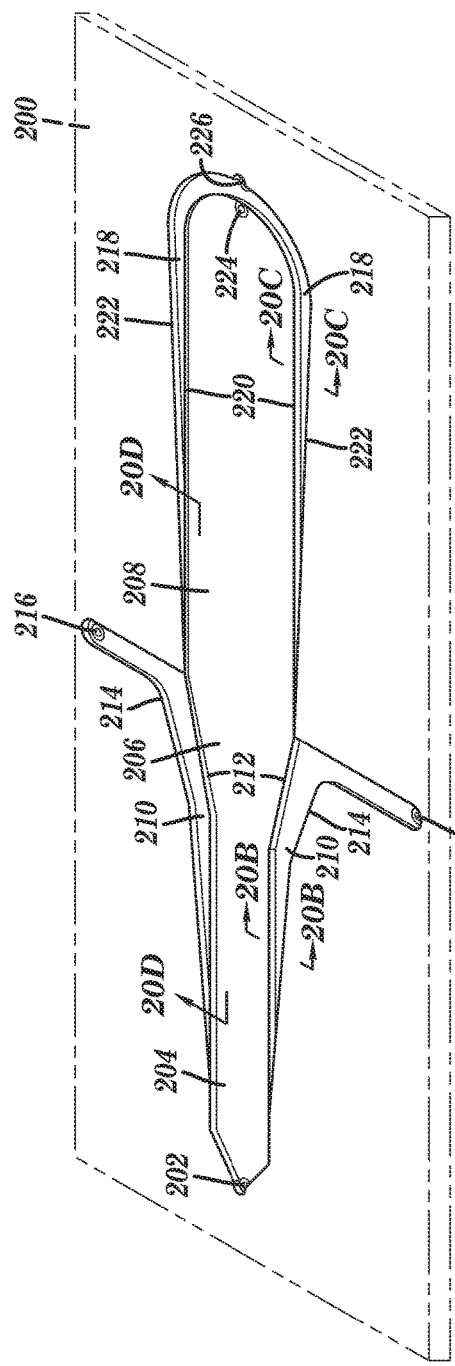
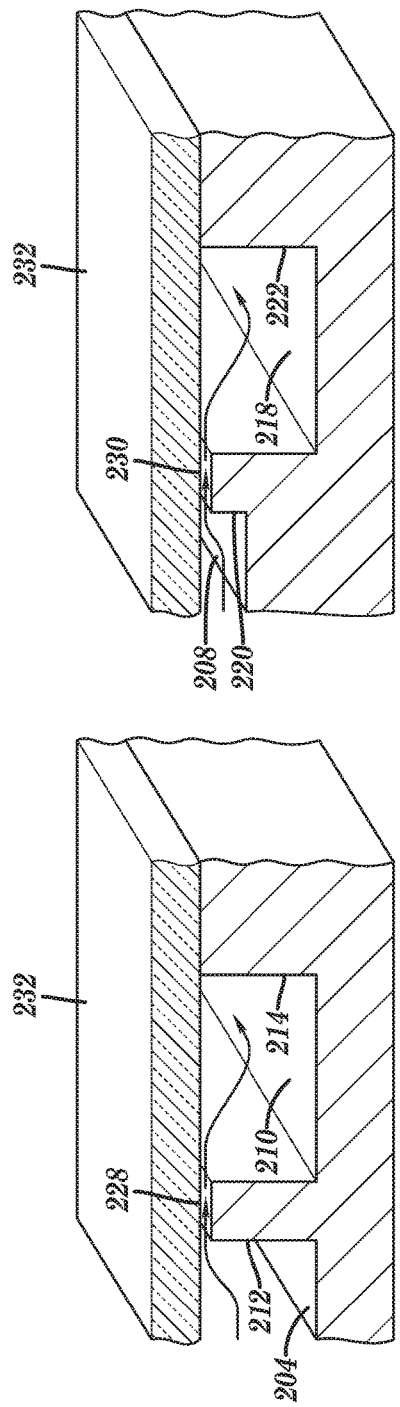
FIG. 20A
FIG. 20B
FIG. 20C

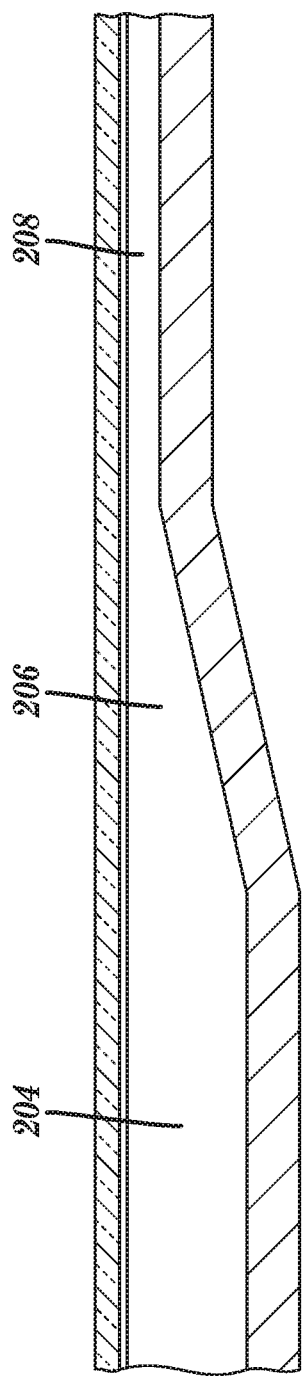

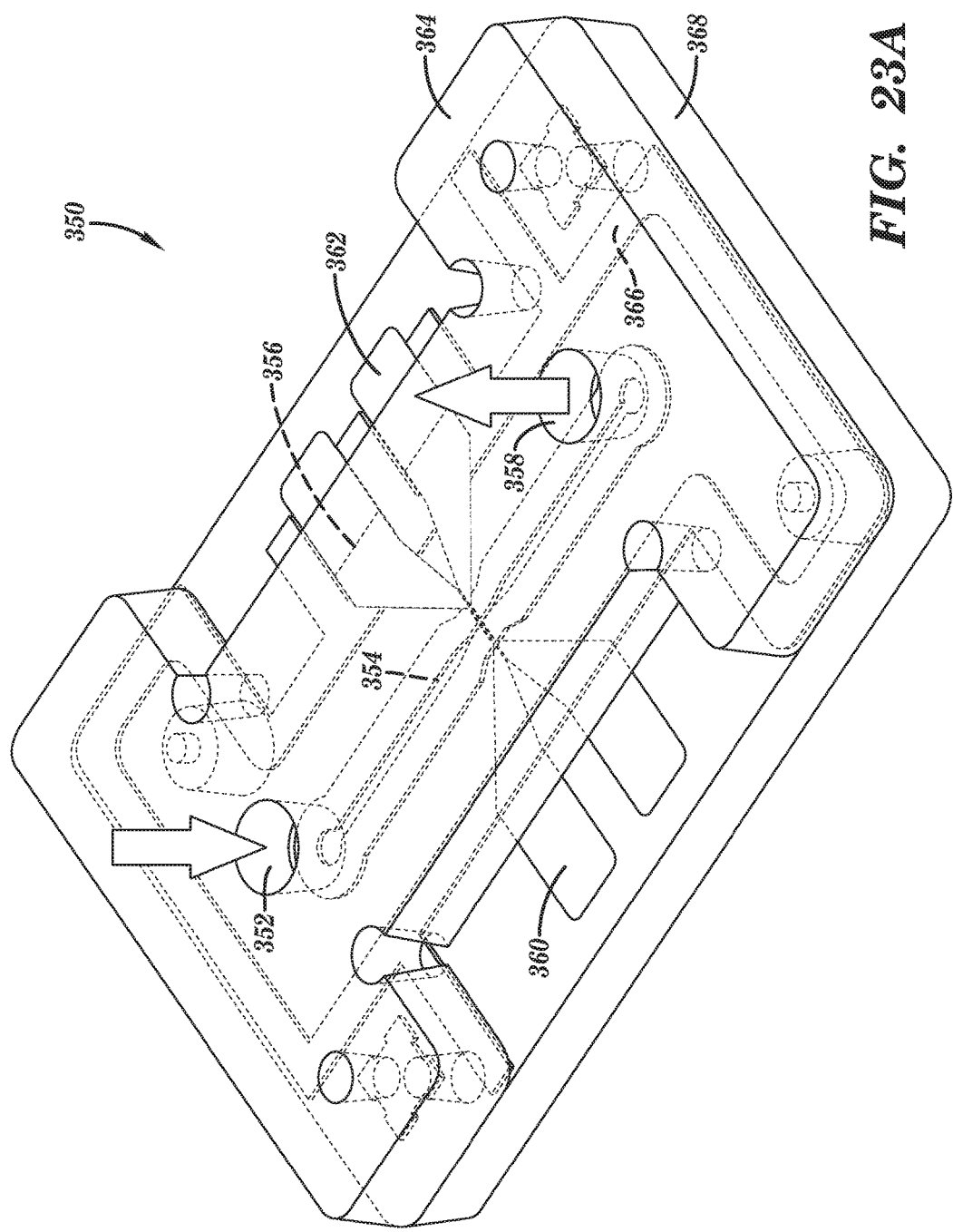

(A) REGULAR MOLD INSERT
(C) MODIFIED POST MOLD INSERT
(B) EMBOSSED POST
(D) EMBOSSED POST

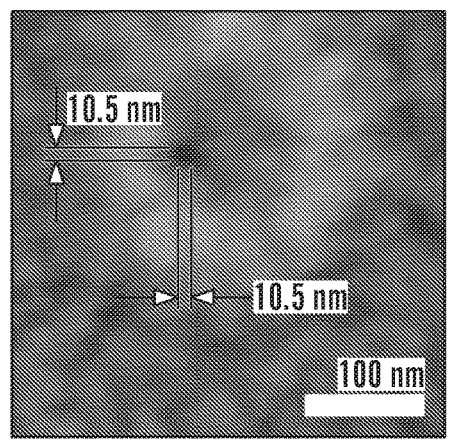
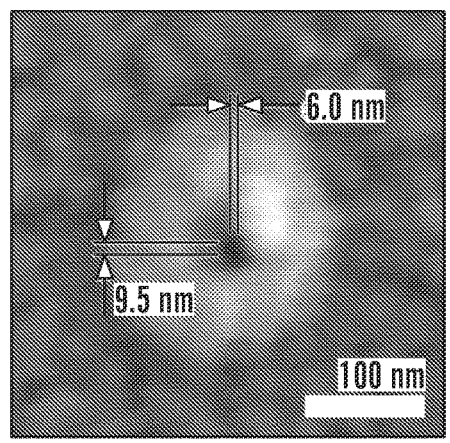
*FIG. 38A*        *FIG. 38B*
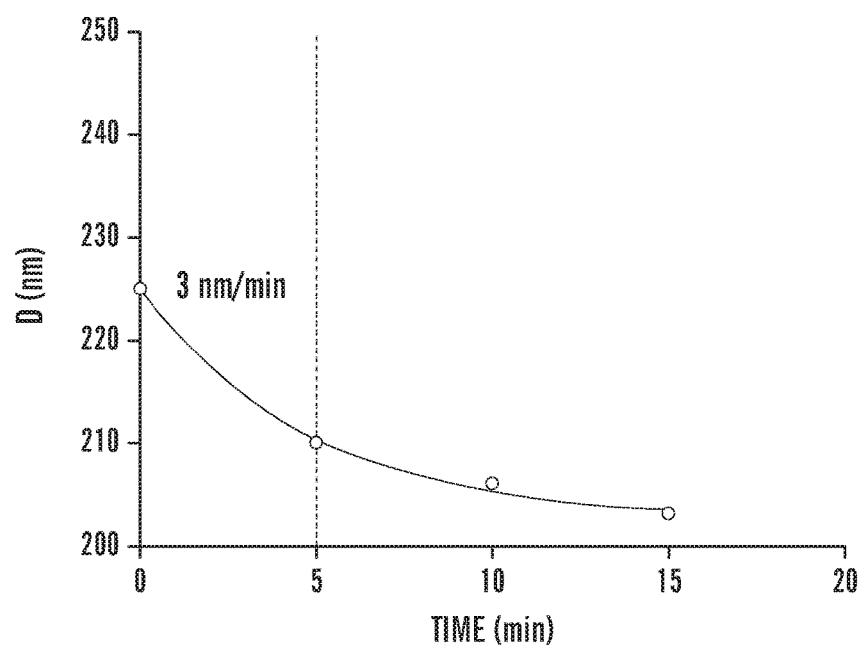
*FIG. 38C*

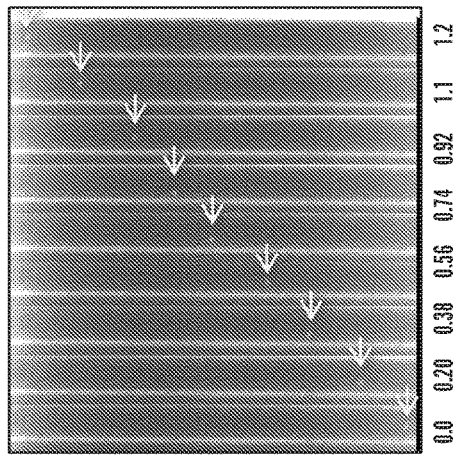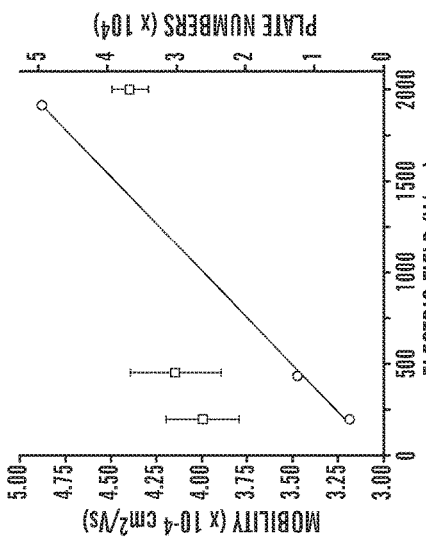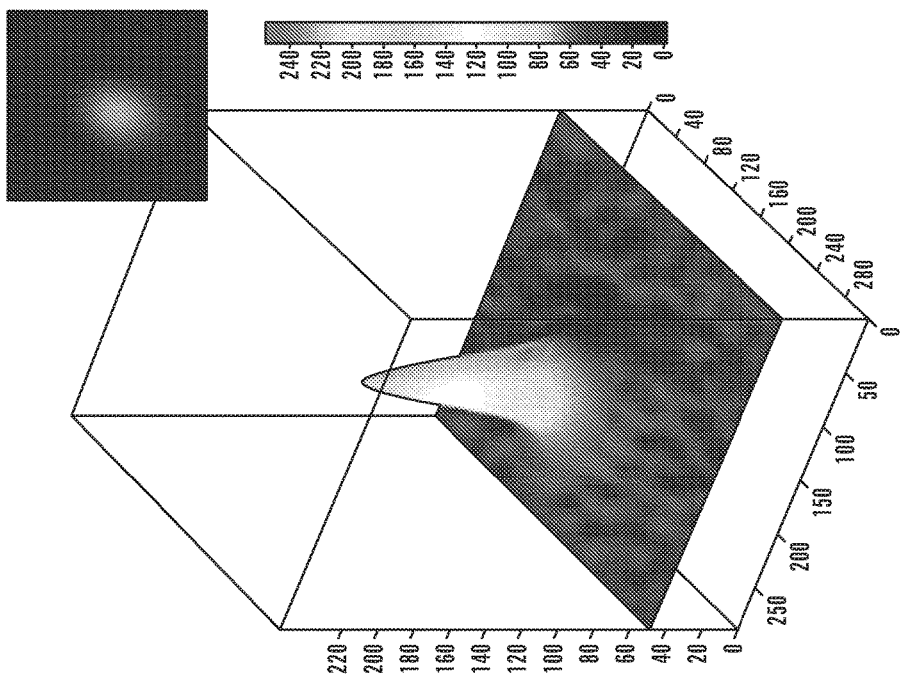
FIG. 40A
FIG. 40B
FIG. 40C

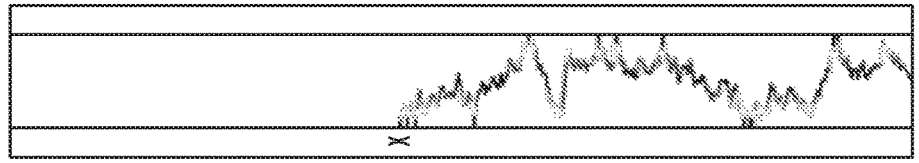
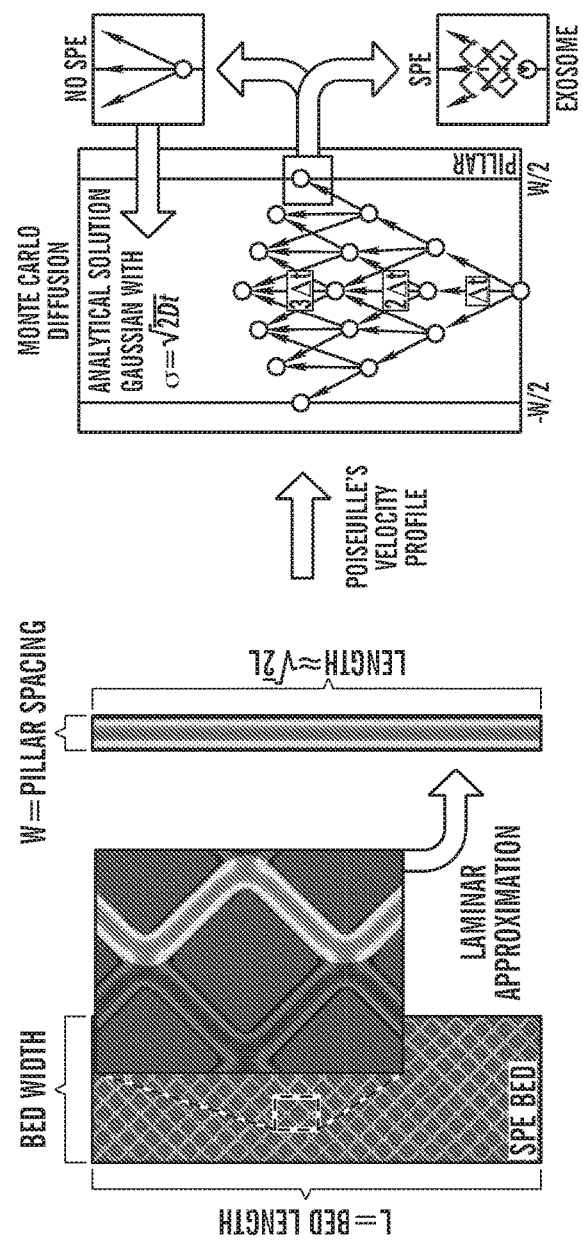
FIG. 45A
FIG. 45B
FIG. 45C

UNIVERSAL MOLECULAR PROCESSOR FOR PRECISION MEDICINE

This application claims the benefit of U.S. Provisional Patent Application Ser. No. 62/137,028, filed Mar. 23, 2015, which is hereby incorporated by reference in its entirety.

STATEMENT OF FEDERAL SUPPORT

This invention was made with government support under Grant Numbers HG006278, EB010087 and EB020594 awarded by the National Institutes of Health and Grant Number CEBT-1067583 from the National Science Foundation. The government has certain rights in this invention.

FIELD OF THE INVENTION

The present invention relates to devices and methods suitable for nucleic acid sequence detection and enumeration.

BACKGROUND OF THE INVENTION

Health care is evolving from "symptom-based" diagnostics to "molecular-based" in vitro diagnostics (IVD). Although IVD accounts for <1% of the annual US health care market, 70% of all clinical decisions are based on results from these tests. Their importance and complexity are growing with increasingly sophisticated and personalized medicine efforts.

Molecular diagnostics are a large contributor to the global IVD market currently accounting for 11% of the market. Unfortunately, the majority of these tests are expensive, involve slow turnaround times from centralized labs and require highly specialized equipment with seasoned technicians to carry out the assay. Therefore, a need exists for molecular platforms and streamlined assays to facilitate more timely and frequent monitoring of patient health to help realize personalized or precision medicine. Not only will new testing paradigms gradually displace centralized laboratory services as one moves to point-of-care testing, but new systems will greatly expand the total market demand for molecular diagnostics.

The present invention is directed at overcoming these and other deficiencies of the art.

SUMMARY OF THE INVENTION

One aspect of the present invention is directed to a device that comprises a biomolecular processor and one or more nanotubes. Each biomolecular processor comprises a bioreactor chamber defined by a solid substrate, a plurality of spaced support structures within said bioreactor chamber and attached to the solid substrate, and one or more capture molecules immobilized to some or all of said plurality of spaced support structures, said one or more capture molecules suitable to bind to a portion of a target nucleic acid molecule in a sample. The one or more nanotubes of the device are defined by the solid substrate and fluidically coupled to the bioreactor chamber. Each of the one or more nanotubes has a passage extending between an input end proximate to the bioreactor chamber and an output end distal to the bioreactor chamber, and comprises one or more nanopores within the passage with each nanopore having a reduced diameter relative to the passage.

Another aspect of the present invention is directed to a device comprising a longitudinally-extending plasma isolation unit defined by the solid substrate and comprising: an entrance passage; a discharge passage which is wider and shallower than the entrance passage; a transition passage connecting the entrance passage and the discharge passage, said transition passage becoming wider and shallower as the transition passages progresses from the entrance passage to the discharge passage; primary side channels extending laterally away from the entrance passage, wherein a separator, positioned between the entrance passage and each primary side channel, is sized to permit plasma, but not cells, to pass from the entrance passage to the primary side channels; and secondary side channels extending laterally away from the discharge passage, wherein a separator, positioned between the discharge passage and each secondary side channel, is sized to permit plasma, but not cells, to pass from the entrance passage to the secondary side channels.

Another aspect of the present invention is directed to a device comprising an extractor unit defined by a solid substrate and comprising an inlet, an outlet, a plurality of separate chambers each extending between and sharing the inlet and said outlet. The device also comprises a plurality of solid pillars in each of the chambers, wherein the pillars have passages between them, and are provided with a material suitable to immobilize cells, nucleic acids, or exosomes from a sample.

Another aspect of the present invention is directed to a device comprising a sensor unit defined by a solid substrate and comprising: an inlet; an outlet; and a cell counter positioned to count cells passing from the inlet to the outlet of said sensor unit.

Another aspect of the present invention is directed to a method for identifying, in a sample, one or more target nucleotide sequences differing from other nucleotide sequences in the sample by one or more nucleotides, one or more copy numbers, one or more transcript sequences, and/or one or more methylated residues. This method involves providing a sample containing one or more target nucleic acid molecules containing the target nucleotide sequence or complements thereof and providing a solid support comprising one or more immobilized capture molecules, said capture molecules suitable to bind to a portion of the one or more target nucleic acid molecules. The method further involves binding the one or more target nucleic acid molecules to the one or more immobilized capture molecules on the solid support thereby immobilizing the one or more target nucleic acid molecules on said solid support, and subjecting the immobilized target nucleic acid molecules or immobilized extension products that are complementary to said target nucleic acid molecule to a ligase detection reaction to produce ligation products hybridized to said immobilized target nucleic acid molecules or immobilized extension products thereof. The ligation products are denatured from the immobilized target nucleic acid molecules or immobilized extension products thereof to release the ligation products from the solid support, and the denatured ligation products are fed through one or more nanopores capable of detecting said ligation products. The method further involves detecting, as a result of said feeding, an identifying signature of each ligation product that is generated when each product passes through the one or more nanopores, and identifying, based on said detecting, the presence of one or more target nucleotide sequences differing from other nucleotide sequences in the sample by one or more nucleotides, one or more copy numbers, one or more transcript sequences, and/or one or more methylated residues.

Another aspect of the present invention is directed to a method for identifying, in a sample, one or more nucleotides in a target nucleotide sequence. This method involves providing a sample containing one or more target nucleic acid molecules containing the target nucleotide sequence or a complement thereof, and providing a solid support comprising one or more immobilized capture molecules, said capture molecules suitable to bind to a portion of the one or more target nucleic acid molecules. The method further involves binding the one or more target nucleic acid molecule to the one or more immobilized capture molecules on the solid support thereby immobilizing the one or more target nucleic acid molecules on said solid support, and contacting the immobilized target nucleic acid molecules or immobilized extension products that are complementary to the target nucleic acid molecule with a solution to form a nucleotide extension reaction mixture. The solution comprises one or more oligonucleotide primers, wherein said oligonucleotide primers are complementary to a portion of said immobilized target nucleic acid molecule or immobilized extension product thereof, a polymerase, and a collection of nucleotide triphosphates, each type of nucleotide triphosphate in the collection having (i) a different cleavable identifying signature-generating moiety, and (ii) a cleavable blocking moiety that inhibits addition of a subsequent nucleotide triphosphate. The nucleotide extension reaction mixture is subjected to a hybridization treatment wherein the one or more oligonucleotide primers hybridize in a base specific manner to their complementary immobilized target nucleic acid molecules or immobilized extension products thereof, and the hybridized oligonucleotide primers are extended by a single base-specific addition of a nucleotide triphosphate from the collection of nucleotide triphosphates to the 3' end of the hybridized oligonucleotide primers. The identifying signature-generating moiety and the blocking moiety are cleaved from each nucleotide added to the hybridized oligonucleotide primers after said extending, and the cleaved identifying signature-generating moiety is fed through one or more nanopores capable of detecting said identifying signature-generating moiety. The method further involves detecting, as a result of said feeding, an identifying signature generated by the cleaved identifying signature-generating moiety when said cleaved moiety passes through the one or more nanopores, and identifying, based on said detecting, the nucleotide triphosphate from the collection of nucleotide triphosphates that was added during said extending, thereby identifying one or more nucleotides in a target nucleotide sequence in the sample.

Circulating markers from blood represents an exciting in vitro diagnostic scenario because of the minimally invasive nature of securing these markers and the plethora of marker types found in blood, such as biological cells, cell-free molecules (proteins and cell-free DNA) and vesicles (nanometer assemblies such as exosomes). Unfortunately, many of these blood-borne markers have not been effectively utilized in clinical practice to manage challenging diseases such as cancer, infectious diseases and stroke to name a few. This deficiency has arisen primarily from the fact that disease associated blood markers are a vast minority in a mixed population making them difficult to find and analyze due to the lack of efficient platforms for their isolation and systems that can determine the molecular structural variations they may harbor. To address this pressing need, an innovative diagnostic platform device capable of selecting circulating markers from whole blood and processing disease-specific molecular signatures is described herein. The envisioned system takes advantage of multiple length scales (mm→nm) to affect unique processing capabilities offered by the system. The system will process whole blood (≥1 mL) and concentrate clinically relevant markers to nL volumes (>10$^6$ enrichment factor) and search for a variety of sequence variations from both DNA and RNA molecules using a solid-phase ligase detection reaction (spLDR) carried out on millions of polymer pillars fabricated in a single step using replication-based technologies. spLDR products are electrokinetically swept into nanometer flight tubes with their identification based on molecular-dependent electrophoretic mobilities; single-molecule processing will be carried out using nanometer flight tubes with detection performed non-optically. The system will provide the ability to select all clinically relevant markers (cells, cell-free DNA and exosomes) from a single blood draw and secure pertinent information from those markers in a fully automated fashion to allow transitioning the platform into clinical practice.

BRIEF DESCRIPTION OF THE DRAWINGS

FIG. 1A is a perspective view of a nanosensor chamber 30 within a nanosensor module. In this embodiment, each nanosensor chamber 30 contains eight biomolecular processors 1, each coupled to a single nanotube 6. FIG. 1B is perspective view of the biomolecular processor 1 and nanotube 6. FIG. 1C is a top view of a nanopore 8 within the nanotube 6 shown in FIG. 1B.

FIG. 2A is a perspective view of a nanosensor chamber containing eight biomolecular processors 1 and eight nanotubes, where only the input end 12 of the nanotube is shown. FIG. 2B is a perspective view showing an isolated biomolecular processor and vertically positioned nanotube. FIG. 2C is a cross-sectional view through the vertically positioned nanotube.

FIGS. 9A-9B show a top view of a nanotube (FIG. 9A) and a circuit diagram of the nanotube with electrodes and measuring circuitry (FIG. 9B). The circuit diagram of FIG. 9B depicts an alternative embodiment for measuring a biomolecule's identifying signature as it passes through a nanopore of the nanotube.

FIGS. 15A-15B are electronic system block diagrams showing two methods for detecting and processing biomolecular identifying signatures from a single nanotube.

FIGS. 18A-18B depict the cell isolation module of the uMPS. FIG. 18A is a perspective view of the cell isolation module comprising the cell capture bed. FIG. 18B (inset of FIG. 18A) is a perspective view of the sinusoidal channels that make up the capture bed of the cell isolation module.

FIGS. 20A-20D depict the plasma isolation module of the uMPS. FIG. 20A is a perspective view of the plasma isolation module. FIG. 20B is a cross-sectional perspective view (through line 20B-20B of FIG. 20A) showing the first main chamber, the first side chamber, and the passageway between the first main chamber and first side chamber of the plasma isolation module. FIG. 20C is a cross-sectional perspective view (through line 20C-20C of FIG. 20A) showing the second main chamber, the second side chamber, and the passageway between the second main chamber and second side chamber of the plasma isolation module. FIG. 20D is a cross-sectional view of the plasma isolation unit taken through line 20D-20D of FIG. 20A.

FIG. 21A is a perspective view of this plasma isolation unit. FIG. 21B is a cross-sectional view of this plasma isolation unit taken through line 21B-21B of FIG. 21A.

FIGS. 23A-23B depict the impedance module of the uMPS. FIG. 23A is a perspective view of the impedance module, and FIG. 23B is an exploded perspective view showing the three layers of the impedance module.

FIG. 26A is a perspective view of the diffusional purification module, and FIG. 26B is a top-view of the inset from FIG. 26A showing the spacing between obstacles within the diffusional purification bed.

FIG. 28B shows an assembled gasket-less seal. The alignment accuracy is ~10 µm. FIG. 28C shows that the superhydrophobic seals between mated pieces when aligned.

FIG. 29A shows the process of making the resin stamp that is used in the process of making the nanofluidic chambers and channels as depicted in FIG. 29B.

FIG. 30A is a schematic of the assembly of the hybrid-based fluidic devices and the thermal press instrument. FIG. 30B shows the temperature-pressure process profile showing the six stages for the thermal fusion bonding cycle.

FIG. 37A is a graph showing the change in current amplitude within the nanopore over time. FIG. 37B shows the statistics for the amplitude of the current peaks obtained from 156 translocation events through the differentially sized nanopores.

FIGS. 38A and 38B are SEM images for SU-8 membranes with perforated conical nanopores having differing diameters. FIG. 38C is graph plotting the reduction of pore size as a function of reflow time.

FIGS. 40A-40F show various aspects of the electrophoretic transport of silver nanoparticles (AgNP) through a nanotube. FIG. 40A is an intensity image of a single AgNP parked in a nanotube showing the intensity of the localized surface plasmon resonance of the single nanoparticle. FIG. 40B is representation of the electrophoretic transport for a single nanoparticle event (60 nm AgNP) in a nanotube. FIG. 40C shows a plot of the electrophoretic mobility and the theoretical plate number, which measures the variance of the mobility, as a function of field strength. FIGS. 40D-40F are histograms of time-of-flight events for silver nanoparticle in nanotube.

FIG. 45A shows a computational fluid dynamics simulation of plasma flow through a solid-phase extraction bed comprised of diamond micropillars with 15 µm side length and 5 µm spacing. FIG. 45B shows a Monte Carlo diffusion simulation. FIG. 45C represents results from the Monte Carlo diffusion simulation for the transport (pressure driven flow) through a 10 µm wide channel whose walls are coated with an affinity agent specific for an exosome. The "X" marks the location where the exosome has become bound to the surface through the association between the surface attached affinity agent and the targeting antigen resident on the surface of the exosome.

DETAILED DESCRIPTION OF THE INVENTION

One aspect of the present invention is directed to a device that comprises a biomolecular processor and one or more nanotubes. Each biomolecular processor comprises a bioreactor chamber defined by a solid substrate, a plurality of spaced support structures within said bioreactor chamber and attached to the solid substrate, and one or more capture molecules immobilized to some or all of said plurality of spaced support structures, said one or more capture molecules suitable to bind to a portion of a target nucleic acid molecule in a sample. The one or more nanotubes of the device are defined by the solid substrate and fluidically coupled to the bioreactor chamber of the biomolecular processor. Each of the one or more nanotubes has a passage extending between an input end proximate to the bioreactor chamber and an output end distal to the bioreactor chamber, and comprises one or more nanopores within the passage with each nanopore having a reduced diameter relative to the passage.

Figure 1A:
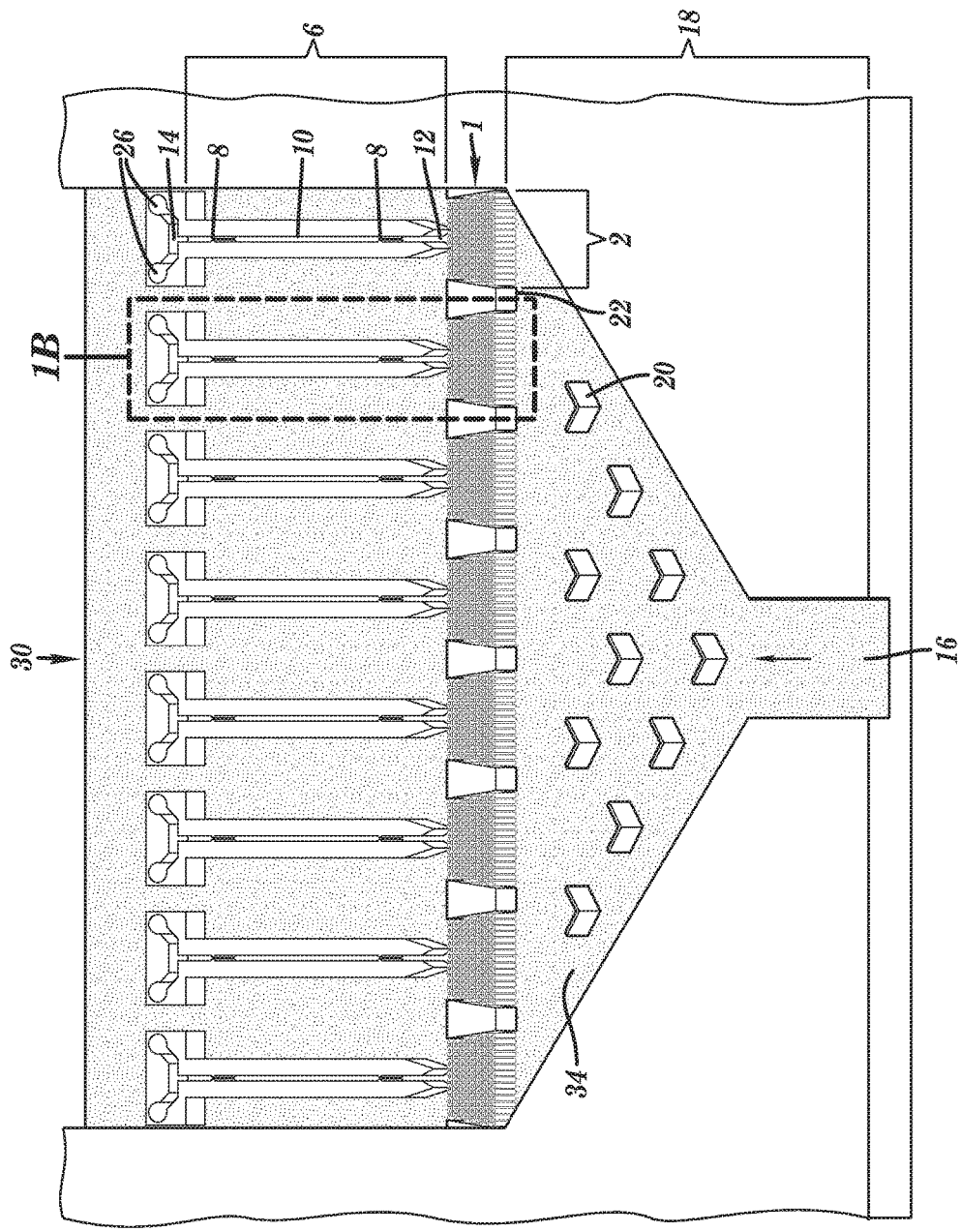
FIGS. 1A-1C are perspective views of the biomolecular processor and one or more nanotubes of a device as described herein.

FIG. 1A is perspective view of a nanosensor chamber 30 containing a series of biomolecular processors 1 and nanotubes 6 as described herein. Each biomolecular processor 1 has a bioreactor chamber 2 that contains a plurality of spaced solid support structures 4 attached to the solid substrate. Two walls of each bioreactor chamber 2 are defined by separators 22 that help direct material within the bioreactor chamber 2 into the nanotube 6 that is coupled to the bioreactor chamber 2. The bioreactor chamber is further defined by a top cover plate, which is not shown in FIG. 1A. The nanosensor chamber also comprises a fluidic input port 16 and a feeder channel 18. The feeder channel 18 fluidically couples the input port 16 and the plurality of biomolecular processors 1 to deliver a sample from the input port 16 to the plurality of biomolecular processors 1. The feeder channel optionally contains one or more or a plurality of baffles 20 that function to disperse the sample entering the input port 16 to the plurality of biomolecular processors 1.

Figure 1B:
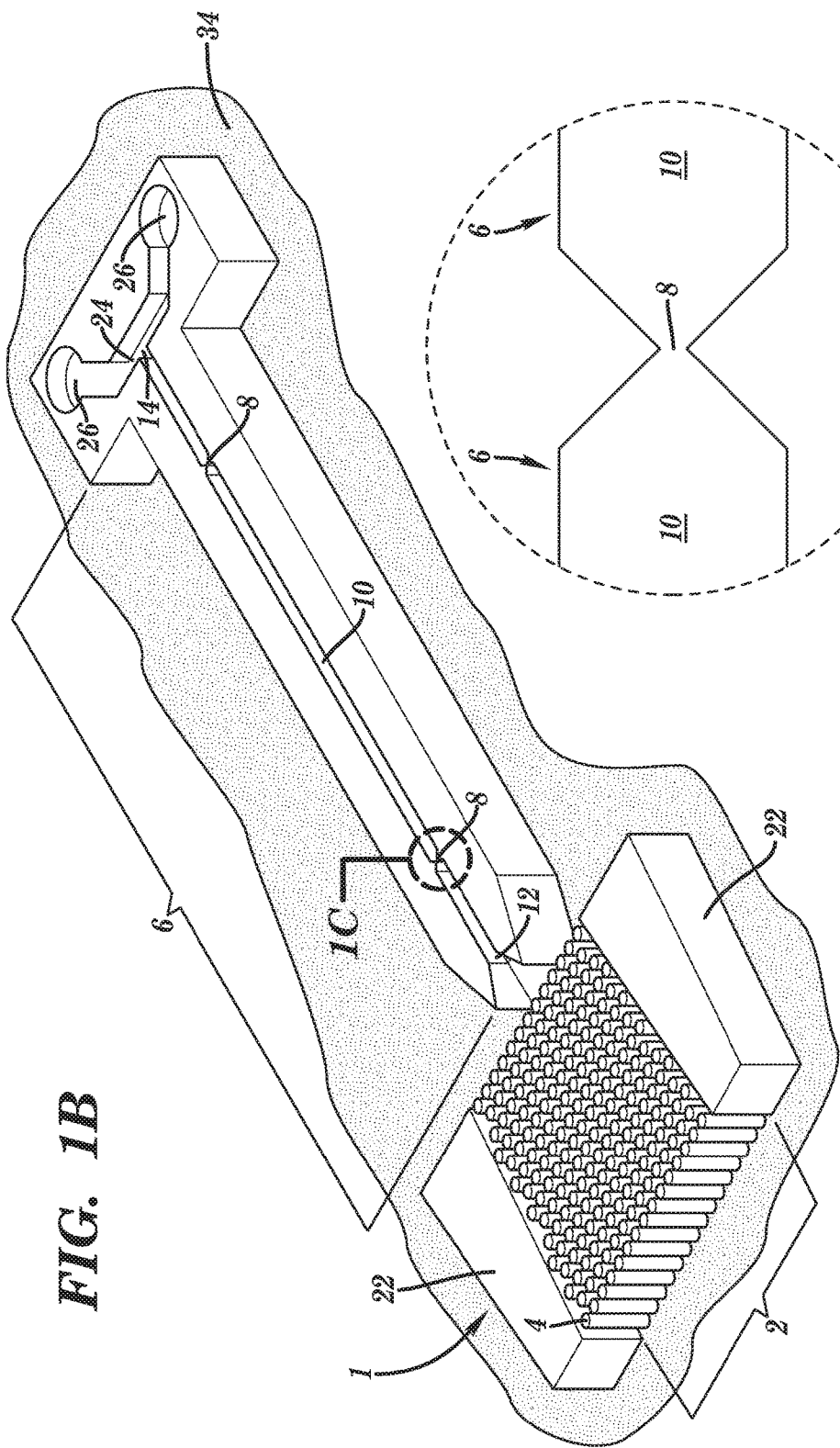
Figure 1C:
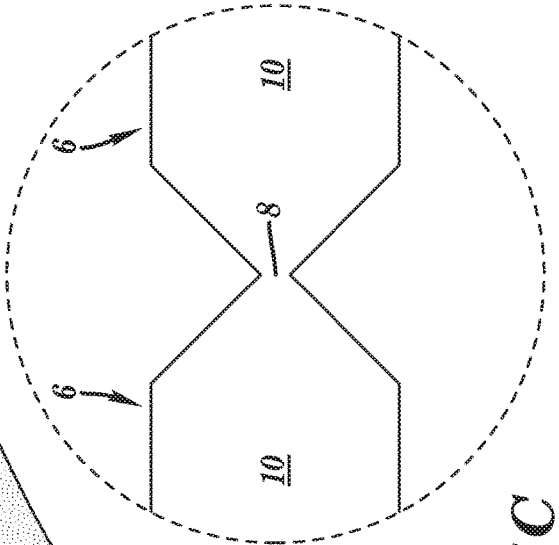

As depicted in FIG. 1A, each biomolecular processor is coupled to a nanotube. The perspective view of FIG. 1B shows a magnified view of nanotube 6 and biomolecular processor 1 containing bioreactor chamber 2. The nanotube 6 contains an input end 12 that is proximate to the bioreactor chamber 2 of the biomolecular processor 1, an output end 14 that is distal to bioreactor chamber 2, and a passage 10 that extends between the input 12 and output 14 ends. Input end 12 of nanotube 6 shown in FIG. 1B has a tapered inlet to help electrically load molecules into nanotube 6. The output end 14 of the nanotube 6 can be coupled to a microfluidic network 24 and microscale reservoirs 26 for inlet and outlet of fluids and bioreagents. Within the passage 10 of the nanotube 6 is one or more nanopores 8. The embodiment depicted in FIG. 1B shows a nanotube 6 having two nanopores 8; however as described herein and shown in FIG. 4, the nanotube can contain more than two nanopores. Each nanopore 8 has a reduced diameter relative to the remaining passage 10 of the nanotube 6 as shown in FIG. 1C.

In one embodiment, the biomolecular processors, one or more nanotubes, and any further units to which the biomolecular processors and nanotubes are, directly or indirectly, fluidically coupled to are positioned on a base plate. A cover plate is fitted on the base plate to form a compartment that seals the biomolecular processor, the nanotubes, and any further units.

Figure 2A:
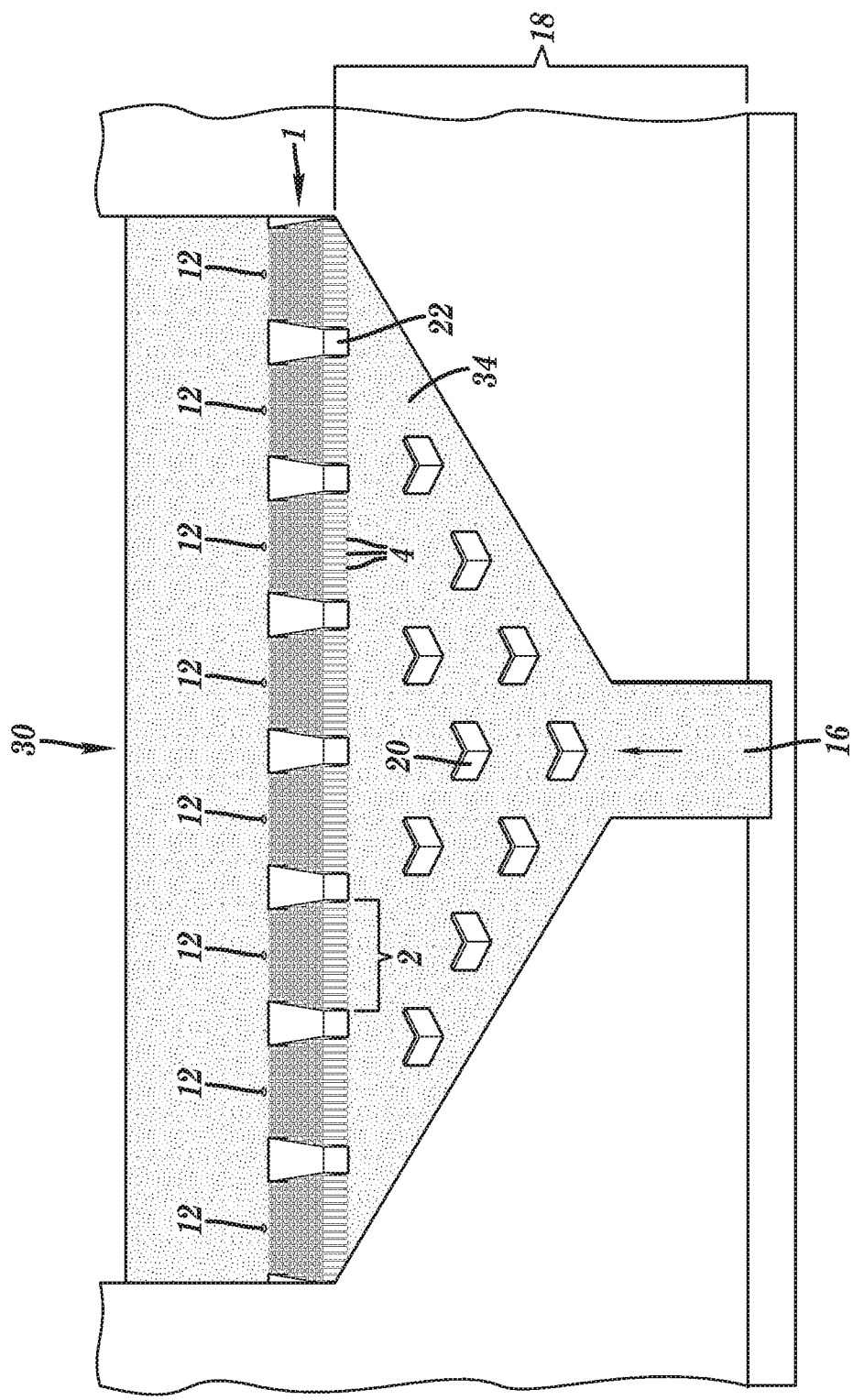
FIGS. 2A-2C are views of the biomolecular processor and one or more vertically orientated nanotubes of a device as described herein.
Figure 2B:
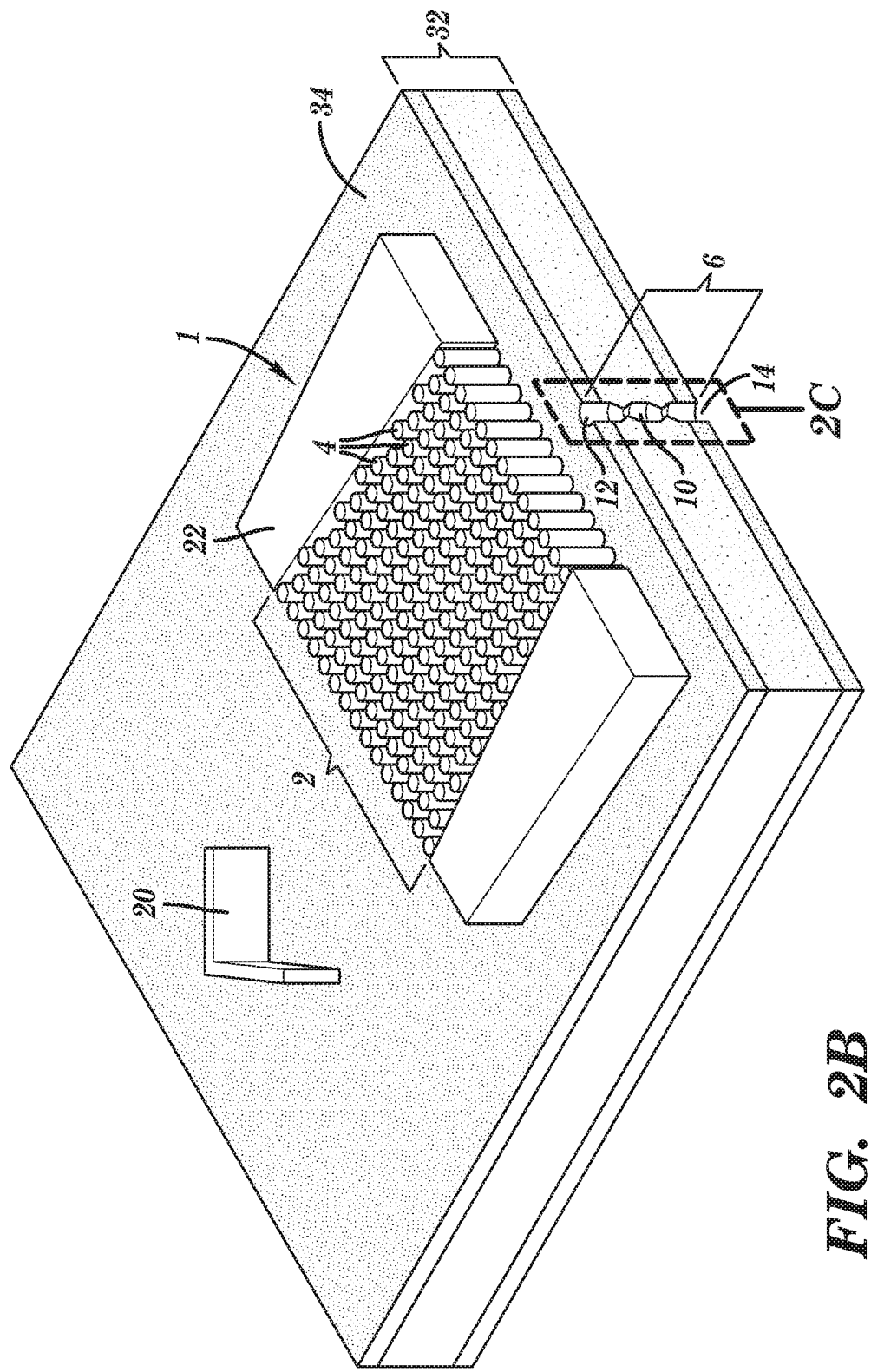
Figure 2C:
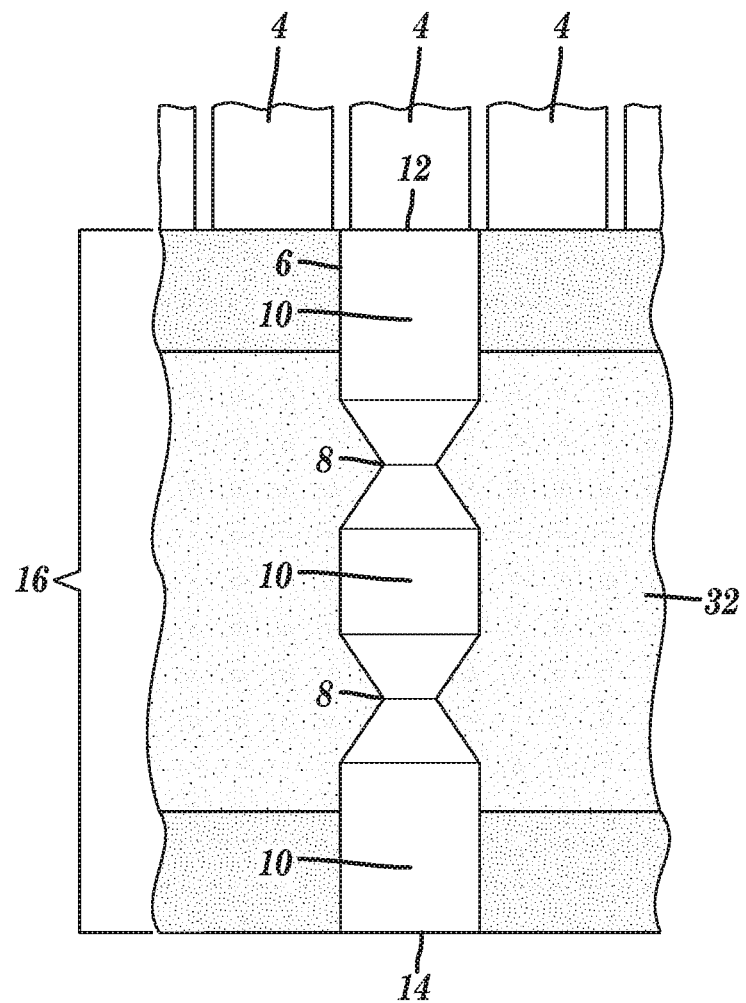

FIGS. 2A-2C show an alternative arrangement of the biomolecular processor and nanotube of a device of the present invention. FIG. 2A is a perspective view of a nanosensor chamber 30 containing eight biomolecular processors 1 and eight nanotubes, where only the input end 12 of the nanotube is visible in this perspective. In this embodiment, nanotube 6 is positioned vertically within solid substrate 32, while bioreactor chamber 2 of biomolecular processor 1 is located on the surface of solid substrate 34 adjacent to the input end 12 of the nanotube. Sample enters the bioreactor chamber 2 via the fluidic input 16, flows through the feeder channel 18 of the nanosensor chamber 30 where it is distributed among the bioreactor chambers 2 by the baffles 20 present in the feeder channel 18. The sample flows through the plurality of spaced support structures 4 within the bioreactor chamber 2, where target molecules are captured by capture molecules that are immobilized on the solid support structures 4. Upon release of the target molecules or other biomolecular products representative of the target molecules from the capture molecules, the target molecules or biomolecular products thereof are directed into the input end 12 of the nanotube for detection. FIG. 2B shows a magnified perspective view of one biomolecular processor 1 in nanosensor chamber on the surface 34 of substrate 32 and adjacent to nanotube 6 which is vertically positioned within the substrate 32. FIG. 2C is a cross-section of nanotube 6 vertically positioned in the substrate 32, showing the passageway 10 (also referred to as a nanochannel) and nanopores 8 of nanotube 6.

The solid substrate of the bioreactor chamber of the biomolecular processor can be made from a wide variety of materials. The solid substrate may be biological, nonbiological, organic, inorganic, or a combination of any of these. In one embodiment, the solid substrate is a polymeric material or other moldable material. Suitable polymeric materials include, without limitation, poly(methyl methacrylate) (PMMA), polycarbonates (PC), epoxy-based resins, copolymers, polysulfones, elastomers, cyclic olefin copolymer (COC), and polymeric organosilicons. The bioreactor chamber can be fabricated from thermoplastic via, for example, Nano-Imprint Lithography (NIL) as described herein and sits atop a heating element.

The spaced support structures 4 of the bioreactor chamber 2 encompass any raised structures, such as pillars as depicted in FIG. 1B. The space support structures 4 sit on top of the solid substrate surface 34 and have exposed top, bottom, and side surfaces. These spaced support structures 4 can be any geometrical three-dimensional shape, including, without limitation, spherical, cone, cylinder, triangular prism or tetrahedron, cube, rectangular prism, dodecahedron, hexagonal prism, octagonal prism, etc. Capture molecules are immobilized to the support structure surfaces (i.e., the top and side surfaces of the structures). In one embodiment, the capture molecules are oligonucleotides comprising a nucleotide sequence that is complementary to a nucleotide sequence that is a part of or is appended to a target molecule in a sample. For example, in one embodiment, the capture molecule is a poly-dA$_{30}$ oligonucleotide that is complementary to a poly-dT tail appended to a target nucleic acid molecule. The capture molecules are immobilized to the support structure surfaces via any suitable linker molecule.

The dimensions of the bioreactor chamber vary depending on a number of factors, including e.g., the device it is housed on and the type of sample being analyzed. The bioreactor chamber can be 5, 10, 15, 20, 25, 30, 35, 40, 45, 50 µm wide by 5, 10, 15, 20, 25, 30, 35, 40, 45, 50 µm deep, with a height of 1, 2, 3, 4, 5, 6, 7, 8, 10, 11, 12, 13, 14, 15, 16, 17, 18, 19, 20, 25, 30, 35, 40, 45, 50 µm. In one embodiment, the bioreactor chamber of the biomolecular processor is 20 µm×20 µm. The size of the bioreactor chamber dictates the number of solid support structures housed inside. Each bioreactor chamber may contain 100, 150, 200, 250, 300, 350, 400, 500, 550, 600, 650, 700, 750, 800, 850, 900, 950, 1000, or more spaced support structures, where each support structure is 0.1, 0.5, 1, 1.5, 2, 2.5, 3, 3.5, 4, 4.5, 5, 5.5, 6, 6.5, 7, 7.5 8, 8.5, 9, 9.5, or 10 µm in diameter and 0.5, 1, 2, 3, 4, 5, 6, 7, 8, 9, 10, 11, 12, 13, 14, 15, 16, 17, 18, 19, 20 µm tall. The support structures must be spaced apart from each other within the bioreactor chamber to allow flow through of a fluidic sample. In one embodiment, a bioreactor chamber of a biomolecular processor contains 250-300 spaced support structures that are 1 µm in diameter and 5 µm tall.

Design of the biomolecular processor is based on maximum loading capacity to accommodate the target nucleic acid molecules present in, e.g., a 1 mL of test sample, e.g., plasma. A pillar 1.0 µm in diameter and 5.0 µm in height (aspect ratio=5.0) has an available surface area of $1.57 \times 10^{-7}$ cm$^2$. With the known surface density of functional groups on UV-activated cyclic olefin copolymer (COC) ($19.0 \times 10^{-9}$ moles cm$^{-2}$) (Jackson et al., *Lab Chip* 14:106-117 (2014), which is hereby incorporated by reference in its entirety), there are $1.8 \times 10^9$ available sites on a pillar of these dimensions. When immobilizing dA$_{30}$ oligonucleotides (radius of gyration=3 nm) for capturing TdT tailed targets, the highest surface density that can be achieved for a hexagonally packed surface is $8 \times 10^{-12}$ moles cm$^{-2}$, which is smaller than the density of surface carboxylates upon UV/O$_3$ activation. UV exposure (254 nm) of the polymer pillars generates surface-confined carboxylic acids only at sites exposed to the activating radiation, and suitable for attaching NH$_2$-dA$_{30}$ primers in the presence of EDC/NHS to generate a stable amide bond of the primer to the surface (Jackson et al., *Lab Chip* 14:106-117 (2014), which is hereby incorporated by reference in its entirety). However, not every capture molecule will capture a target. Based on literature reports of 5,000 molecules per 1 µm$^2$, it is estimated that a given pillar can accommodate 78,500 molecules (Ma et al., *Proc Natl Acad Sci USA* 110:14320-14323 (2013), which is hereby incorporated by reference in its entirety). Thus, for a full load and no replication to accommodate capture of ~400 billion ssDNA molecules the array would have 5.1 million pillars. For a 20×20 µm bioreactor chamber that has pillars (each pillar being 1 µm in diameter) spaced by 0.25 µm with hexagonal packing, the number of pillars per bioreactor chamber is 288; the minimum number of bioreactor chambers required is 17,674. Thus, in one embodiment a nanosensor module has ~17,700 biomolecular processors.

Figure 3:
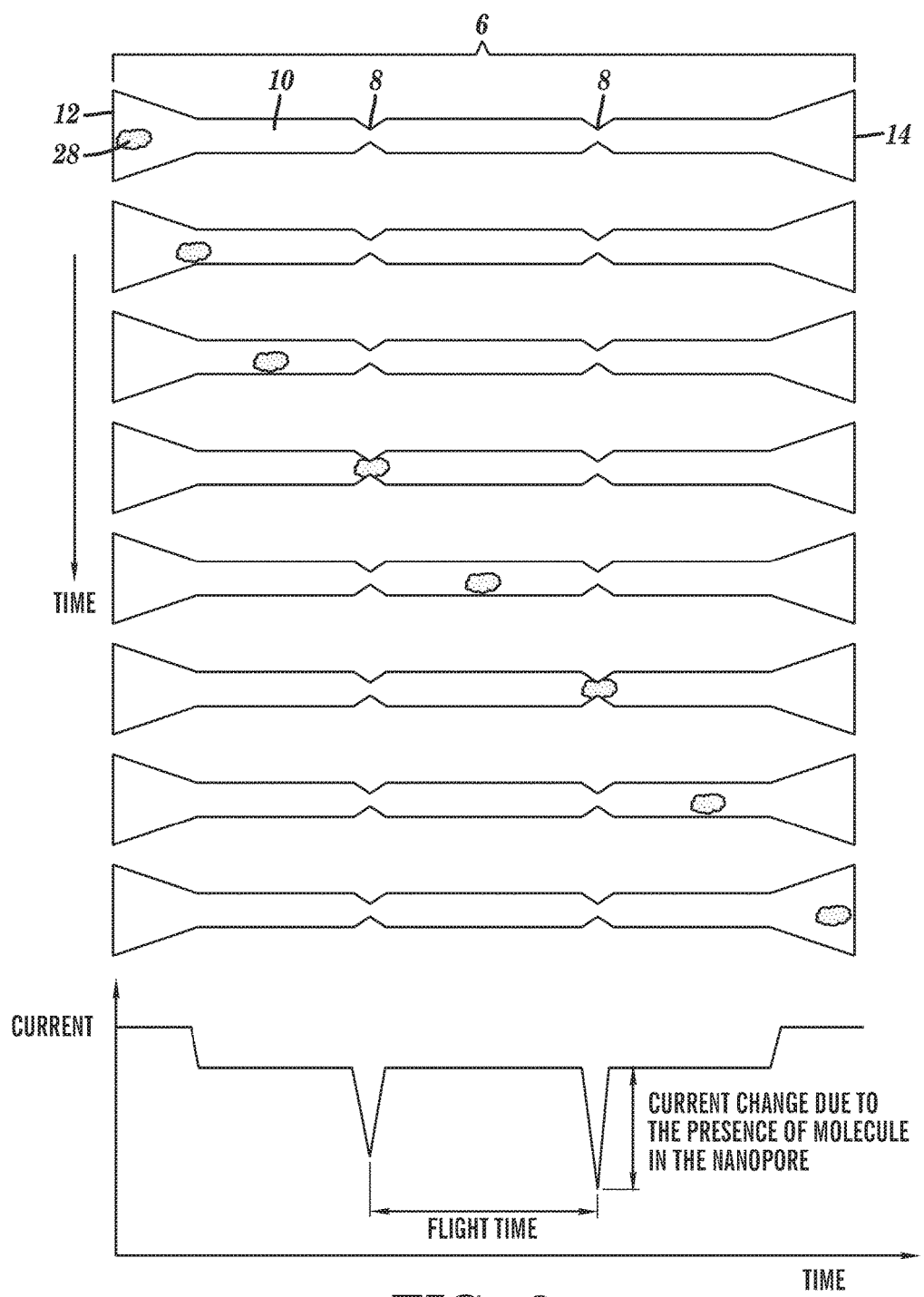
FIG. 3 is series of panels depicting the travel of a single molecule through a nanotube. Each panel shows a different position of the single molecule in the nanotube, with the graph at the bottom of the figure tracking the change in current as the molecule traverses the nanotube and nanopores within the nanotube.

As described in more detail herein, the nanotube functions to detect single molecules generated and/or processed within the bioreactor chamber of the biomolecular processor. Single molecules from the bioreactor chamber enter the nanotube at the input end and electrokinetically travel through the passageway of the nanotube containing the nanopores and exit at the output end. When the molecule passes through a nanopore, a current signature is generated depending on the ionic salt concentration and the size of the molecule that is detected. FIG. 3 is a schematic illustration of this process. The series of panels in FIG. 3 show the position of a biomolecule 28 in the nanotube 6 over time and the resulting current transient that is generated as the biomolecule 28 moves through the nanotube passage 10. The graph at the bottom of this figure tracks the change in current as a function of travel time of the single biomolecule through the flight tube. When a single biomolecule 28 enters into the nanotube 6 at the input end 12, there is a change in the transient current. When the single biomolecule 28 enters into a nanopore 8, there is additional change in the transient current, which will return to the previous value when the biomolecule 28 exits the nanopore 8, thus generating a drop in the current vs. time plot shown at the bottom of FIG. 3. Upon reaching the second in-plane synthetic pore, another current transient is generated and from the time difference between the first and second current transients, the flight time of the single molecule can be deduced and used to identify the single molecule traveling through the flight tube. The flight time depends on molecular structure and charge of the single molecule.

The nanotube may be 10-200 nm wide, 10-200 nm deep, and 5 to 250 µm long. In one embodiment, the nanotube is 10, 20, 30, 40, 50, 60, 70, 80, 90, 100, 110, 120, 130, 140, 150, 160, 170, 180, 190, or 200 nm wide. In another embodiment, the nanotube is 10, 20, 30, 40, 50, 60, 70, 80, 90, 100, 110, 120, 130, 140, 150, 160, 170, 180, 190, or 200 nm deep. In another embodiment the nanotube is 5, 10, 20, 30, 40, 50, 60, 70, 80, 90, 100, 110, 120, 130, 140, 150, 160, 170, 180, 190, 200, 210, 220, 230, 240, or 250 µm in length. In one embodiment, the dimensions of the nanotube passageway are less than or equal to 50 nm wide and less than or equal to 50 nm deep. In another embodiment of the present invention, the dimensions of the nanotube passageway are less than or equal to 25 nm wide and less than or equal to 25 nm deep. In another embodiment of the present invention, the dimensions of the nanotube passageway are less than or equal to 15 nm wide and less than or equal to 15 nm deep. In another embodiment of the present invention, the dimensions of the nanotube passageway are less than or equal to 10 nm wide and less than or equal to 10 nm deep. In another embodiment of the present invention, the dimensions of the nanotube passageway are less than or equal to 5 nm wide and less than or equal to 5 nm deep. The nanotube passageway can be 1 µm to >250 µm in length or 5 µm to 250 µm in length, and may have any desired geometrical cross-section, i.e., hemispherical, triangle, square, rectangle, pentagon, hexagon, heptagon, or octagon.

In one embodiment of the present invention, the nanotube channel comprises a polymeric material, e.g., PMMA, PC, epoxy-based resins, copolymers, polysulfones, elastomers, and polymeric organosilicons, or any combination of these materials. The polymeric material may be in its native state, or, alternatively, surface modified to enhance biomolecule discrimination and detection. For example, a polymeric passage wall may comprise a neutral, hydrophobic, hydrocarbon surface with different degrees of chain order. In another example, the nanotube passage wall surface may comprise a charge neutral, hydrophilic surface. In yet another example, the nanotube passage wall surface may comprise a charged, hydrophilic surface. As noted above, the composition of the nanotube passage wall will effect the time-of-flight of the biomolecule, and therefore helps define the identifying signature of a biomolecule.

The wall surface of the nanotube passageway comprising a neutral, hydrophobic, hydrocarbon surface with different degrees of chain order can be formed from monolayers of methyl-terminated alkane chains having various lengths that are built on the polymer nanochannel surfaces (Henry et al., "Surface Modification of Poly(methyl methacrylate) Used in the Fabrication of Microanalytical Devices," *Anal. Chem.* 72:5331-5337 (2000), which is hereby incorporated by reference in its entirety). The monolayers can be formed by attachment of amino-alkanes to carboxylic acid-terminated surfaces (McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Alternatively, the monolayers can be formed from urea-linked alkane layers on amine functionalities attached to the polymer via amide bonds (Henry, A. C., "Surface Modification and Characterization of PMMA Used in the Construction of Microelectromechanical Systems," In *Chemistry*, pp. 147, Louisiana State University, Baton Rouge (2001); Henry et al., "Surface Modification of Poly(methyl methacrylate) Used in the Fabrication of Microanalytical Devices," *Anal. Chem.* 72:5331-5337 (2000), which are hereby incorporated by reference in their entirety). For example, well-ordered octadecyl monolayers can be formed on PMMA surfaces by reaction of n-octadecylisocyanate with amine-terminated PMMA surfaces (Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001), which is hereby incorporated by reference in its entirety), and these C$_{18}$-PMMA surfaces are excellent for chromatographic separations in embossed channels (Galloway et al., "Contact Conductivity Detection in Poly(methyl methacylate)-Based Microfluidic Devices for Analysis of Mono- and Polyanionic Molecules," *Anal. Chem.* 74:2407-2415 (2002), which is hereby incorporated by reference in its entirety).

Thus, various chain length n-alkylisocyanates can be used to make hydrophobic polymer surfaces possessing different degrees of order, which will affect the flight-time of passing molecules. Issues regarding non-zero electroosmotic flows (EOFs) can be addressed by capping unreacted foundation groups (Henry, A. C., "Surface Modification and Characterization of PMMA Used in the Construction of Microelectromechanical Systems," In *Chemistry*. Louisiana State University, Baton Rouge (2001); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety).

One approach for creating hydrophilic, charge neutral surfaces, involves reacting properly activated carboxylic-acid terminated polymer surfaces with ethanolamine or amino-tri(ethyleneglycol) (Wei, S., "Multianalyte Detection of Breast Cancer by Fabrication of Hybridmicroarrays on Polymer-based Microanalytical Devices," In *Chemistry*. Louisiana State University, Baton Rouge (2005), which is hereby incorporated by reference in its entirety). As an alternative, amine-terminated PMMA and PC surfaces can be modified with glycols having surface generated carboxylic groups, such as glycolic acid or carboxyl-tri(ethyleneglycol). Cationic surfaces can be formed using well-established methods for production of amine-terminated polymers (Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001); Henry et al., "Surface Modification of Poly(methyl methacrylate) Used in the Fabrication of Microanalytical Devices," *Anal. Chem.* 72:5331-5337 (2000); McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Anionic surfaces will result from routes that lead to either carboxylic-acid terminated surfaces (McCarley et al., "Resist-Free Patterning of Surface Architectures in Polymer-Based Microanalytical Devices," *J. Am. Chem. Soc.* 127:842-843 (2005); Vaidya et al., "Surface Modification and Characterization of Microfabricated Poly(carbonate) Devices: Manipulation of Electroosmotic Flow," *Analyst* 127:1289-1292 (2002), which are hereby incorporated by reference in their entirety) or those bearing sulfonic acids, with the latter having an almost pH-independent surface charge (Henry, A. C., "Surface Modification and Characterization of PMMA Used in the Construction of Microelectromechanical Systems," In *Chemistry*, pp. 147, Louisiana State University, Baton Rouge (2001), which is hereby incorporated by reference in its entirety).

Figure 4:
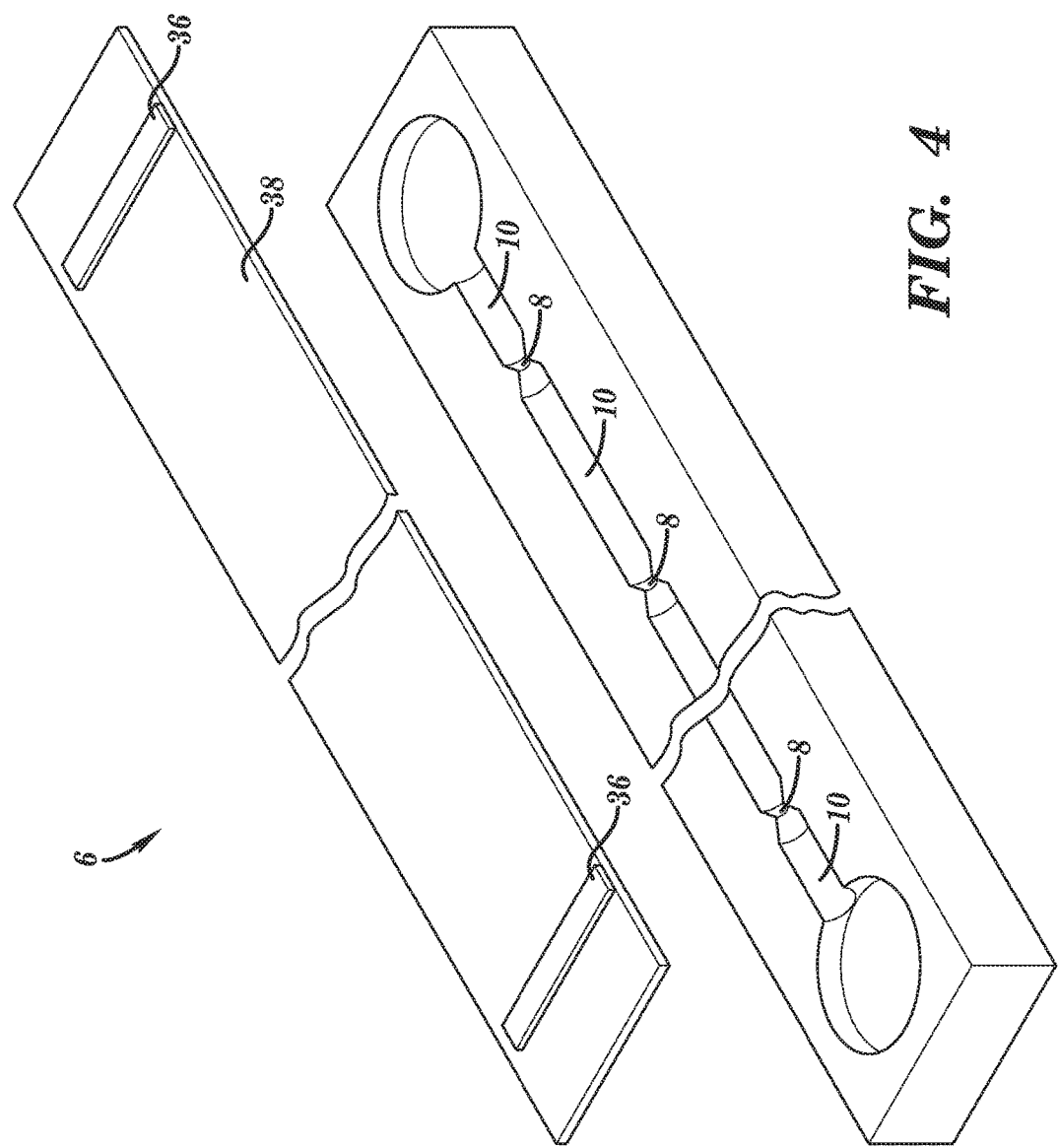
FIG. 4 is a perspective view of a nanotube showing the positioning of three or more (represented by the break in the nanotube) synthetic nanopores within a single nanotube. This figure also shows the nanotube cover and placement of the electrodes on the cover.

The nanotube as described herein may comprise one time-of-flight segment that is situated between two nanopores within a nanotube. Alternatively, as shown in FIG. 4, the nanotube may comprise multiple, i.e., three of more, time-of-flight segments coupled together, with each time-of-flight segment situated between two nanopores. In one embodiment, each time-of-flight segment is characterized by a passage wall having a unique chemistry that differentially interacts with the passing molecules and their identifying signature modifiers or generators. The time-of-flight segments can be the same length or different lengths, having the same or different surface chemistries. The time-of-flight channels have the same dimensional limitations as the nanotube with regard to the width and depth. In other words, the time-of-flight channel may be 10-200 nm wide and 10-200 nm deep. With regard to length, the time-of-flight channel is the length of the nanotube between two nanopores. Therefore, the length of the time-of-fight channel may be <5 µm and >200 µm or anywhere between 5-200 µm in length. These design formats allow for multidimensional separations to enhance identification and characterization of individual molecules moving through the nanotube.

The dimensions of the nanopores of the nanotube are significantly smaller than the passageway of the nanotube. For example the nanopore can be 1-150 nm in width or depth or both, and may be 5-500 nm long. The nanopore may be 1, 2, 3, 4, 5, 10, 20, 30, 40, 50, 60, 70, 80, 90, 100, 110, 120, 130, 140, or 150 nm in width or depth or both, and may be 5, 10, 20, 30, 40, 50, 60, 70, 80, 90, 100, 110, 120, 130, 140, 150, 160, 170, 180, 190, 200, 210, 220, 230, 240, 250 260, 270, 280, 290, 300, 310, 320, 330, 340, 350, 360, 370, 380, 390, 400, 410, 420, 430, 440, 450, 460, 470, 480, 490, 500 nm long. When two or more nanopores are present in a nanotube, each or some of the two or more nanopores may have the same or different dimensions. In one embodiment, two or more spaced nanopores are of different dimensions so that when the detector measures changes in current levels across the spaced two or more nanopores for a particular biomolecule, current change differences between the two or more spaced nanopores establish that that biomolecule is passing through the two or more spaced nanopores in a sequential manner and the time between those current changes.

As described herein, the nanopore is a small hole within the nanotube, having a diameter that is smaller than the diameter of passage extending through the nanotube on either side of the nanopore. As noted above, one nanotube may contain two or more nanopores, each nanopore being the same or different. The diameter of the nanopore is of a size such that when molecules of interest pass through the nanopore, the passage of the molecules is detected by a change in electrical signal, for example, current, though the nanopore. In one embodiment the nanopore comprises a protein, such as alpha-hemolysin or MspA, which can be modified or unmodified. In another embodiment, the nanopore is a synthetic nanopore, e.g., a solid state nanopore or graphene nanopore. Solid state nanopores can be produced as described herein or as described in U.S. Pat. No. 7,258,838 which are hereby incorporated by reference in their entirety. Exemplary solid state nanopores are disclosed by Storm et al., *Nature Mater.* 2:537-540 (2003); Venkatesan et al., *Adv. Mater.* 21:2771-2776 (2009); Kim et al., *Adv. Mater.* 18:3149-3153 (2006); Nam et al., *Nano Lett.* 9:2044-2048 (2009) and Healy et al., *Nanomedicine* 2:875-897 (2007) which are incorporated herein by reference in their entirety. In another embodiment, the nanopore comprises a hybrid protein/solid state nanopore in which a nanopore protein is incorporated into a solid state nanopore. Suitable nanopores are described, for example in Mager, M. D. & Melosh, N. A, *Adv. Mater.* 20:4423-4427 (2008); White, R. J. et al., *Langmuir* 22:10777-10783 (2006); Venkatesan, B. M. et al., *Biomed. Microdevices* 13:671-682 (2011); Iqbal et al., *Nature Nanotech.* 2:243-248 (2007); Wanunu et al., *Nano Lett.* 7:1580-1585 (2007); Siwy et al., *Chem. Soc. Rev.* 39:1115-1132 (2009); Kowalczy et al. *Nature Nanotech.* 6:433-438 (2011); and U.S. Patent Application Publ. No. US20100331194, which are hereby incorporated by reference in their entirety.

In another embodiment, the nanopore is a graphene nanopore. Suitable graphene nanopores are described in Geim, A.

K., *Science* 324:1530-1534 (2009); Fischbein et al., *Appl. Phys. Lett.* 93:113107-113103 (2008); Girit et al. *Science* 323:1705-1708 (2009); Garaj et al., *Nature* 467:190-193 (2010); Merchant et al., *Nano Lett.* 10:2915-2921 (2010); Schneider et al., *Nano Lett.* 10:3163-3167 (2010), which are hereby incorporated by reference in their entirety.

In one embodiment, the device of the present invention comprises 1-100 biomolecular processors and nanotubes, 100-1,000 biomolecular processors and nanotubes, 1,000-10,000 biomolecular processors and nanotubes, 10,000-100,000 biomolecular processors and nanotubes, or 100,000-1,000,000 biomolecular processors and nanotubes. In another embodiment, the device of the present invention comprises more than 1,000,000 biomolecular processors and nanotubes. A series of biomolecular processors and nanotubes can be housed together in a nanosensor chamber, with a series of nanosensor chambers being housed together in a nanosensor unit or module on a device as described in more detail herein. For example, in one embodiment, 8 biomolecular processors and 8 nanotubes are housed together to form one nanosensor chamber, with the nanosensor unit comprising 2,500 nanosensor chambers.

In accordance with this aspect of the present invention, the device further comprises electrodes positioned at locations upstream of the bioreactor chamber and downstream of the one or more nanotubes, and a voltage source is electrically coupled to the electrodes to establish a voltage gradient between the location upstream of the bioreactor chamber and downstream of the one or more nanotubes. This voltage gradient causes molecules to pass from said bioreactor chamber through the one or more nanotubes to the output end. A detector is positioned within the device to measure changes in current levels across the one or more nanopores as biomolecules pass through said one or more nanotubes.

The series of schematics shown in FIG. 3 represent the travel of a single molecule through a flight tube fitted with two nanopores and the change in current ($\Delta I_B$) as a function of travel time of the single molecule through the flight tube. As can be seen in the plot at the bottom of FIG. 3, current flow is at an open channel state before the molecule enters into the nanochannel. When the molecule enters the channel but before entering the pore in this example, $\Delta I_B$ begins to show a negative response, indicating that the ion flux is reduced when the particle enters this channel. At the in-plane pore, the value of $\Delta I_B$ drops to a lower value, but with a transient nature indicating that the particle is within the pore interstitial volume and drops to its nanochannel value as the molecule exists the first pore. Upon reaching the second in-plane nanopore, another current transient is generated. The time difference between the first and second current transients, the flight time of the single molecule can be deduced. The amplitude of $\Delta I_B$ is greater for the second in-plane nanopore with respect to the first, because the pore diameter is smaller; the difference in the $\Delta I_B$ for the first and second pore can be deduced by either making the pore longer or adjusting the pore diameter.

It is also possible to use a series of three or more nanopores within the flight tube. In FIG. 4, the break in the nanotube represents the presence of "n" pores placed in series, where "n" is any desired number. This can provide many benefits such as the ability to generate consensus between time-of-flight measurements to reduce error in the determination. In addition, different types of surface coatings can be imposed on the nanotube walls between a set of pores as described supra to improve single molecule identification by taking advantage of a technique called multi-dimensional chromatography. This multidimensional approach can also increase the peak capacity of the system to allow for higher multiplexing capabilities.

FIG. 4 also illustrates a top cover 38 of the nanotube 6, and placement of the two electrodes 36 on the top cover 38, where the electrodes are positioned near the input and output ends of the nanotube. In another embodiment, the cover plate may contain a third electrode that is positioned between the nanopores. In accordance with this embodiment, a nanotube containing "n" nanopores, may contain "n" electrodes positioned on the cover plate.

Figure 5:
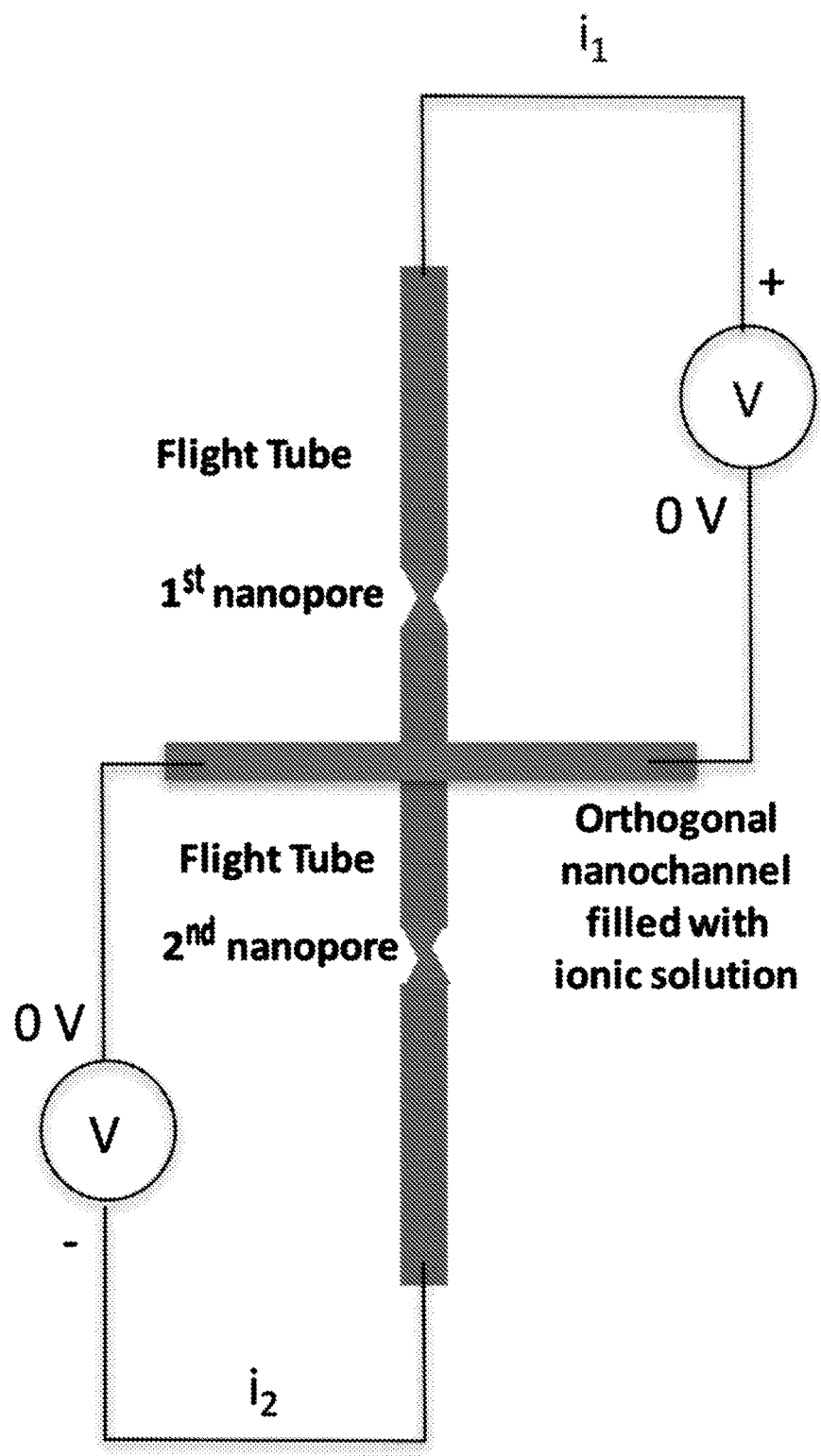
FIG. 5 shows a simplified electrical diagram of one embodiment of the nanotube described herein.
Figure 6:
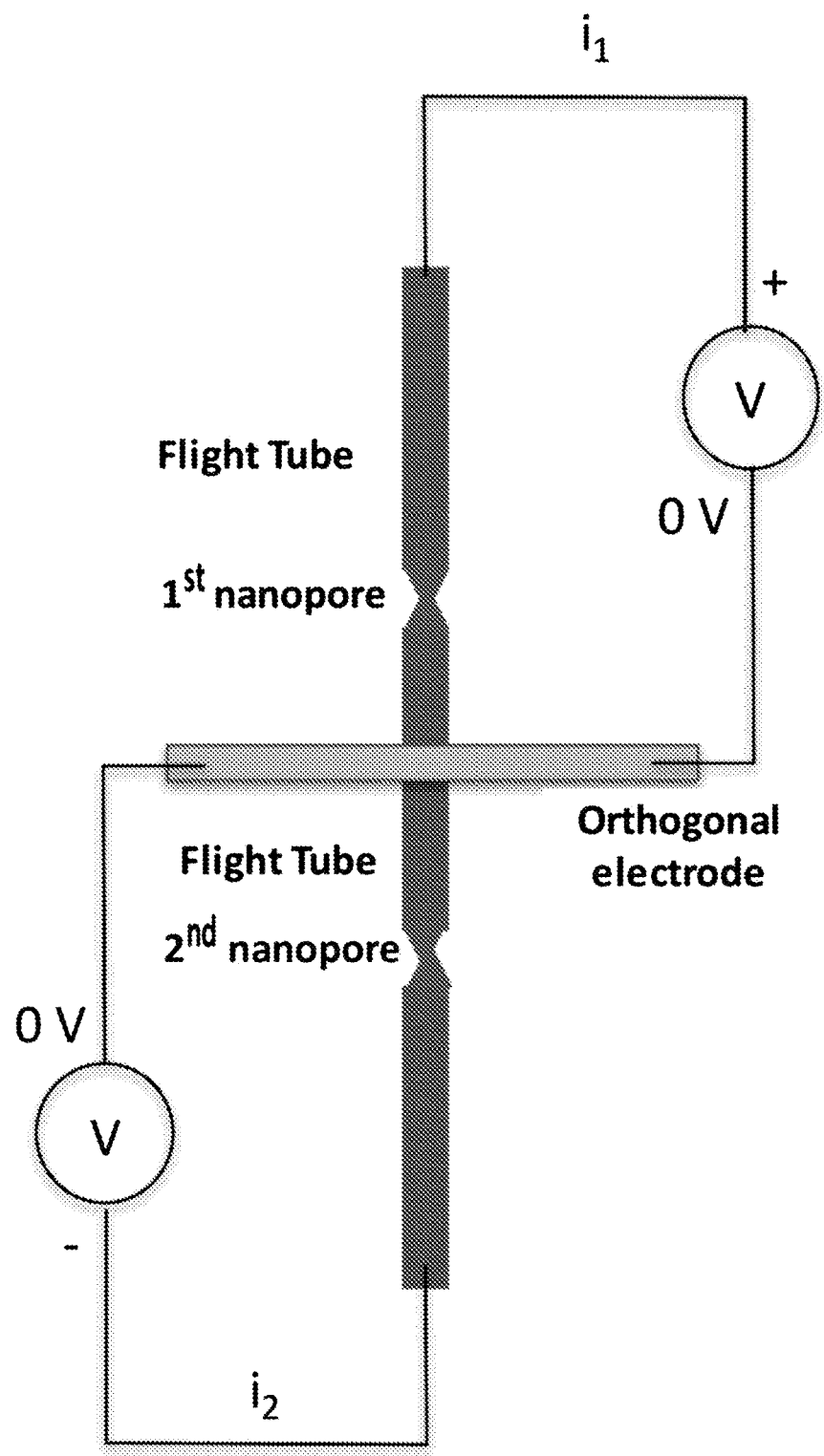
FIG. 6 shows a simplified electrical diagram of one embodiment of the nanotube described herein.

FIGS. 5 and 6 depict alternative single electrode arrangements for detecting current changes in the nanotubes.

In the embodiment depicted in FIG. 5, an additional nanochannel is placed orthogonal to the nanotube containing the nanopores and situated between the two nanopores. When the nanochannel is filled with an ionic solution and connected to an external electrode, the nanochannel filled with ionic solution serves as a common floating ground for separate transient current measurements at the two individual nanopores, which also allows for determining the time-of-flight of a molecule between the two nanopores. A similar structure has been disclosed by Menard et al., *ACS Nano* 6 (10): 9087-9094 (2012), which is hereby incorporated by reference in its entirety.

The embodiment depicted in FIG. 6 also shows an electrode built orthogonal to the nanotube between the two nanopores. In order not to hinder the movement of the molecules passing through passageway of the nanotube, the orthogonal electrode is situated to pass through the top or bottom surface of the flight tube. A thin insulating layer may be coated on the electrode surface. The orthogonal electrode serves as a common floating ground for separate transient current measurements at the two individual nanopores, which also allows for determining the time-of-flight of a molecule between the two nanopores.

Electronic amplification circuitry is necessary to detect changes in current as molecules pass through and occlude the nanopores of the nanotube. The circuit diagrams of FIGS. 7-14 show various alternative embodiments of the electronic circuitry suitable to detect current changes within the nanotube of the device as described herein.

Figures 7A, 7B:
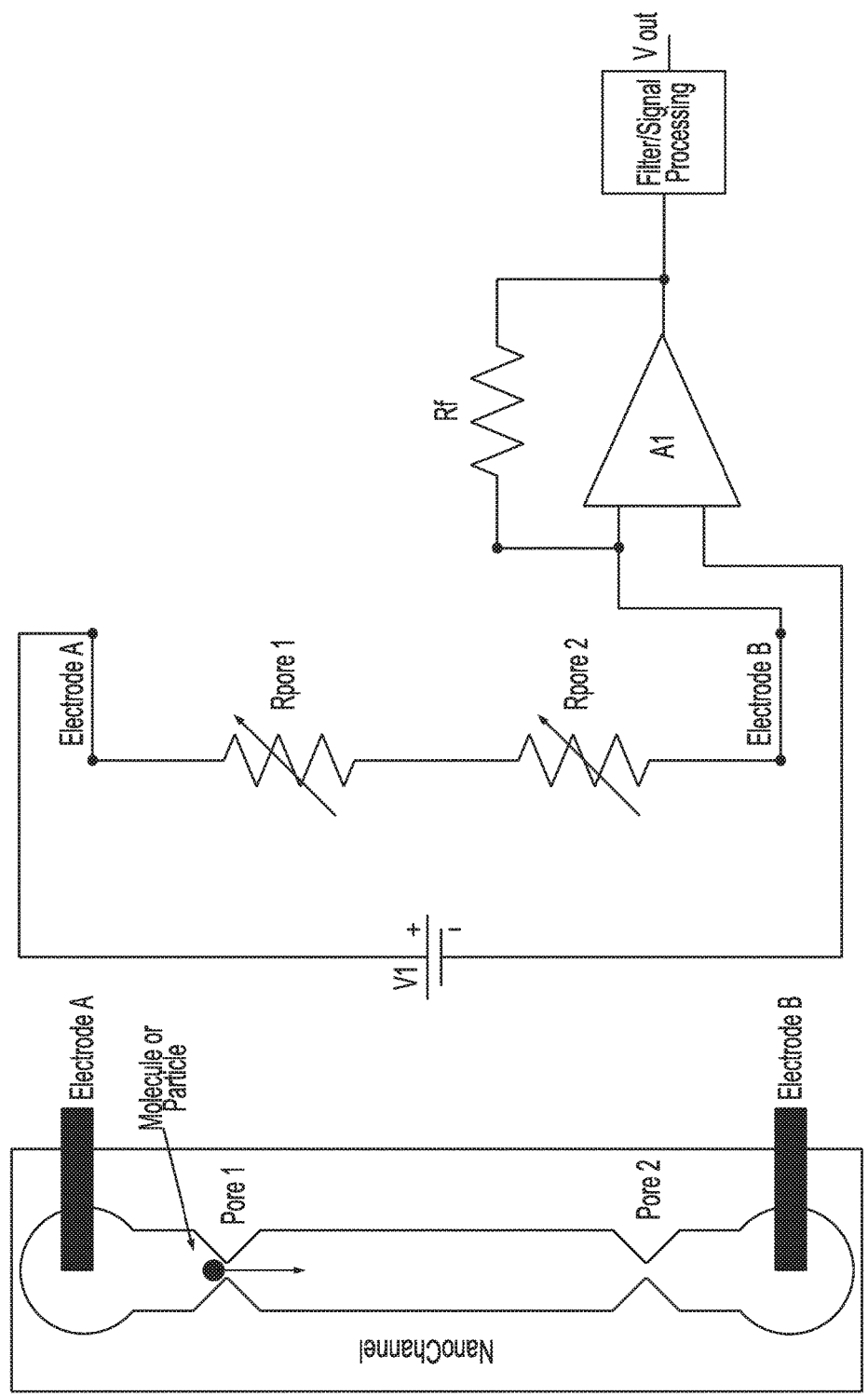
FIGS. 7A-7B show a top view of a nanotube (FIG. 7A), and a circuit diagram of the nanotube with electrodes and measuring circuitry (FIG. 7B). The circuit diagram of FIG. 7B depicts one embodiment for measuring a biomolecule's identifying signature as it passes through a nanopore of the nanotube.

FIG. 7A shows a top view of a nanotube with an entry pore (Pore 1) and an exit pore (Pore 2). Above the entry pore is a fluid chamber, or well, with conductive Electrode A in contact with the fluid contents of the well. In the same fashion, below the exit pore is another fluid chamber with an electrode in it. Biomolecules or nano-particles suspended in an ionic solution are driven from the top well to the bottom well iontophoretically. As the biomolecule moves through the pore and obstructs it, a change in current occurs (blockage current).

FIG. 7B is a circuit diagram of the nanotube with electrodes and measuring circuitry. The circuit diagram shows voltage (V1), which is the potential source for driving molecules or nano-particles through the nanotube. V1 is adjusted to provide the desired speed of transit of the molecules through the nanotube and its pores. The very small diameter of each of the nanopores causes a resistance to the flow of electrical current, represented by "Rpore1" and "Rpore2". Each of these resistances is indicated as a variable resistor, because, when the pore is blocked by a molecule or particle, the resistance increases proportionally to the percentage of the diameter of the pore that is blocked (or alternatively, proportionally to the size of the molecule or particle). This change in current is then measured by the current-to-voltage converter amplifier as shown, and its output is:

$$V_{out} = I * Rf$$

Where:

$V_{out}$ is the output voltage of the amplifier

I is the current resulting from the drive voltage applied across the pores

Rf is the value of the feedback resistor

The output voltage is a pulse with a duration that is proportional to the speed of the molecule or particle and the pore length. The amplitude of the voltage pulse is proportional to the change in current due to the blockage event in each pore. Note that filtering or pulse shaping circuitry, whether in analog or digital form can be used with all of the circuits shown herein to improve the S/N ratio or to improve detectability of the blockage events.

Figures 8A, 8B:
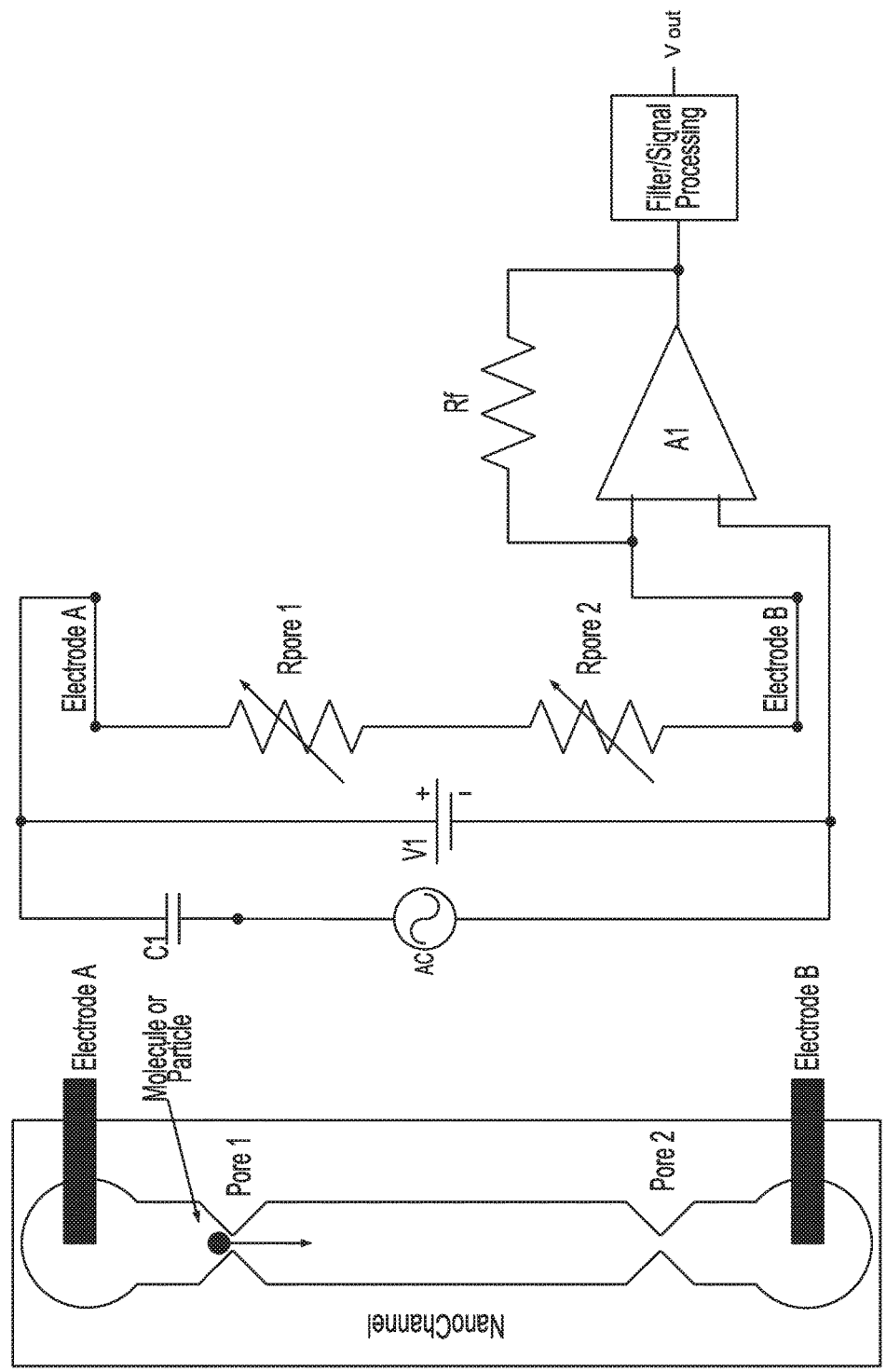
FIGS. 8A-8B show a top view of a nanotube (FIG. 8A) and a circuit diagram of the nanotube with electrodes and measuring circuitry (FIG. 8B). The circuit diagram of FIG. 8B depicts an alternative embodiment for measuring a biomolecule's identifying signature as it passes through a nanopore of the nanotube.

FIGS. 8A-B repeat many of the same features shown in FIGS. 7A-B; however, FIG. 8B shows the introduction of an AC source. In this case, the DC voltage source, V1, still supplies the voltage gradient required to transport the molecules or particles through the nanochannel and its pores, but now the blockage current measurements are not dependent on the DC current from V1. In this case, an AC signal source is capacitively coupled across the nanochannel superimposing an AC signal on top of the DC drive voltage. The changes in the AC current are now used to detect the blockage events instead of the DC current. This decouples the measurement of the blockage currents from the drive voltage and any changes that can occur in the drive voltage. In normal operation, the drive voltage, V1, must be kept at very low potentials to avoid any electrochemistry from occurring at the electrodes. This limits the amplitude of the current change that can be measured. With the AC source, however, the frequency will be chosen to be high enough to prevent electrochemistry from occurring. In addition, since the AC signal is symmetric around zero, no ion polarization will occur. This allows higher voltages to be applied across the nanotube without affecting the transit of the molecules or particles, thus increasing the resulting current which improves the measurability of the blockage event. In addition, filtering (i.e., low pass, bandpass, high pass, or any other filter topology) may be effectively applied to remove noise and drift. Also, signal processing can be implemented to measure the amplitude and phase of the blockage current changes, thus presenting additional correlated measurements that can be used to improve the signal-to-noise ratio for measuring the current blockage event (e.g. molecule resident within the nanopore). Note that in this embodiment, and all subsequent embodiments described below, the AC source can also be transformer-coupled and a secondary center tap can be used to establish the mid-point, or common, voltage.

FIGS. 9A-B illustrate an alternative embodiment to measuring the blockage current as shown in FIGS. 7A-B and 8A-B. This method involves measuring voltage change instead of the current change directly. A similar method has been described in Fraikin et al., "A High-throughput Label-free Nanoparticle Analyser," *Nature Nanotechnology* 6: 308-313 (2011), which is hereby incorporated by reference in its entirety. In this embodiment, a third electrode is placed in the middle of the nanotube between the pores. FIGS. 9A-B show measuring the voltage change across the second pore; however, the voltage change can be measure across either pore (Rpore1 or Rpore2). A standard voltage amplifier with gain can be used to make this measurement as shown. In this embodiment, a blockage event in Pore 1 will cause the voltage measured across Rpore2 to increase. A blockage event in Pore 2 will cause the measured voltage to decrease. This arrangement works best when the resistances of the nanopores are identical in order to obtain the largest voltage change for a blockage event in each pore. However, when the resistances of the nanopores differ greatly, a physical resistor may be added in series with the lowest resistance pore to equalize the voltages. This measurement method offers certain advantages over the current measurement method of FIGS. 7A-B and 8A-B, because for certain values of Rpore, the signal-to-noise ratio and bandwidth of a pure voltage amplifier can be better than those of a current-to-voltage amplifier.

Figures 10A, 10B:
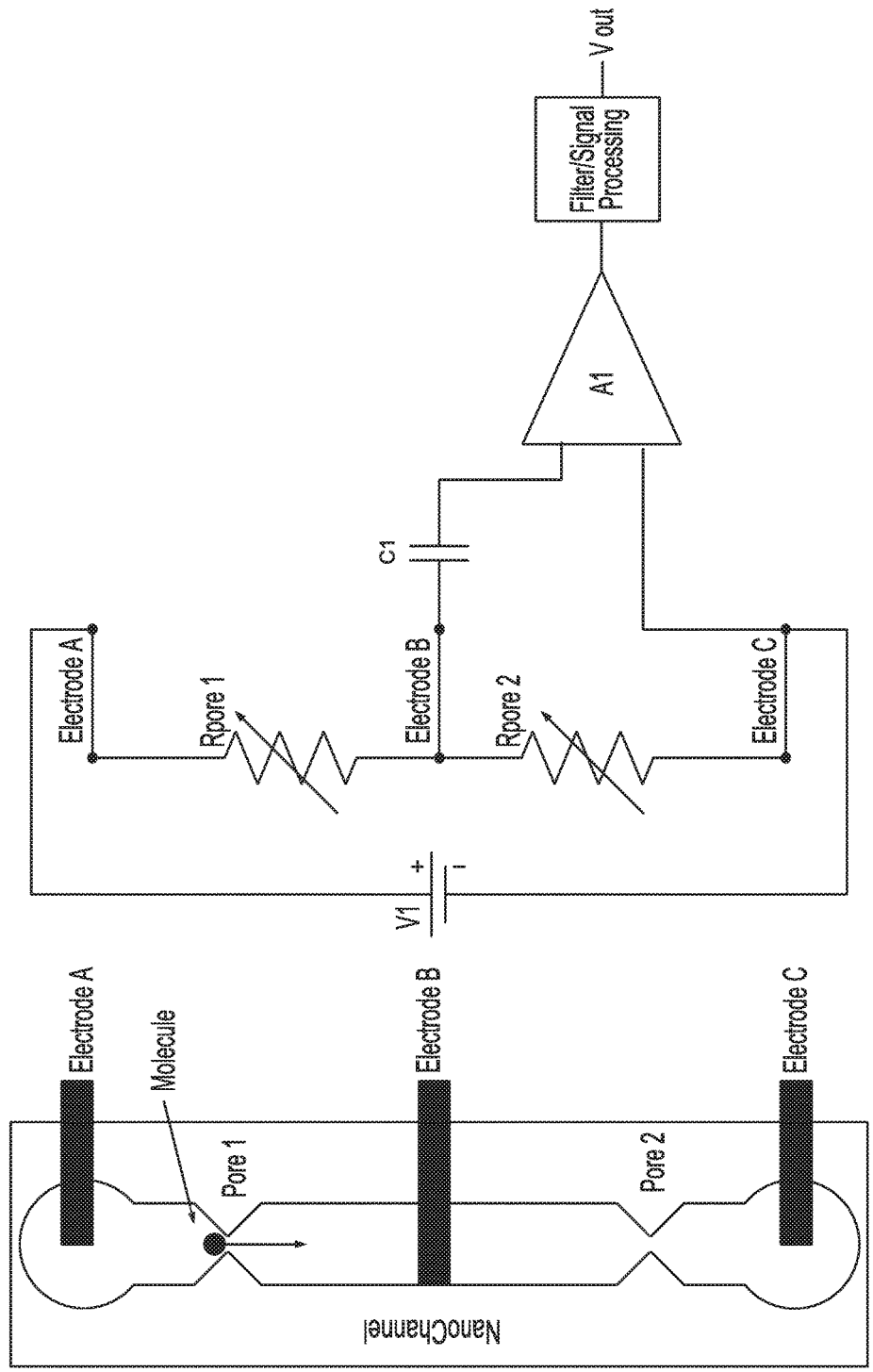
FIGS. 10A-10B show a top view of a nanotube (FIG. 10A) and a circuit diagram of the nanotube with electrodes and measuring circuitry (FIG. 10B). The circuit diagram of FIG. 10B depicts an alternative embodiment for measuring a biomolecule's identifying signature as it passes through a nanopore of the nanotube.

The embodiment depicted in FIGS. 10A-B shows all of the features of FIGS. 9A-B, except that the voltage amplifier is now capacitively coupled. This capacitive coupling can be created by the use of a physical capacitor in series with the electrode, or can be from a dielectric insulator applied to the middle electrode itself (or due to other physical properties of the electrode itself). The first method of capacitive coupling creates a high-pass filter which can be designed to remove low frequency noise and drift from the measurement. The second method of capacitive coupling due to the application of an insulator to the electrode can help to make the electrode chemically inert and thus reduce or eliminate its effect on the DC field potentials and on the molecules or particles as they traverse the nanotube. This capacitive coupling can be used because the voltage signature of a blockage event is theoretically a single square pulse that can be reproduced reasonably well by capturing only its high frequency content. The value of C1 can be adjusted to optimize the cutoff frequency of the high pass filter that is formed.

Figures 11A, 11B:
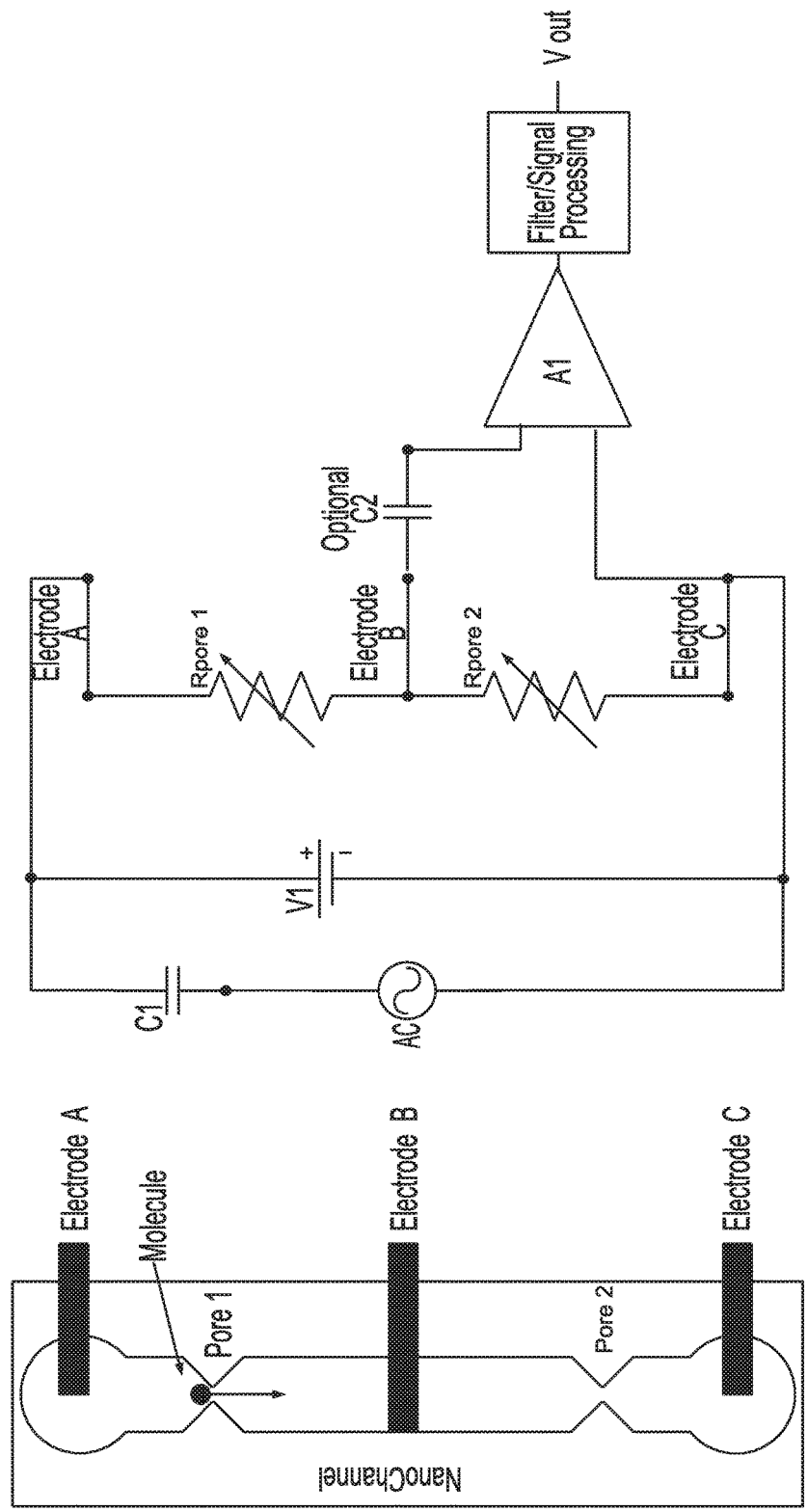
FIGS. 11A-11B show a top view of a nanotube (FIG. 11A) and a circuit diagram of the nanotube with electrodes and measuring circuitry (FIG. 11B). The circuit diagram of FIG. 11B depicts an alternative embodiment for measuring a biomolecule's identifying signature as it passes through a nanopore of the nanotube.

FIGS. 11A-B depict the use of an AC voltage signal superimposed on the DC drive voltage (V1) which, like FIGS. 8A-B above, separate the drive voltage source from the measurement source and has all of the same advantages as those described for FIGS. 8A-B. A1 can be AC or DC coupled through C2. C2 can either be a series capacitor, or as described above, can be a dielectric associated with the electrode itself.

Figures 12A, 12B:
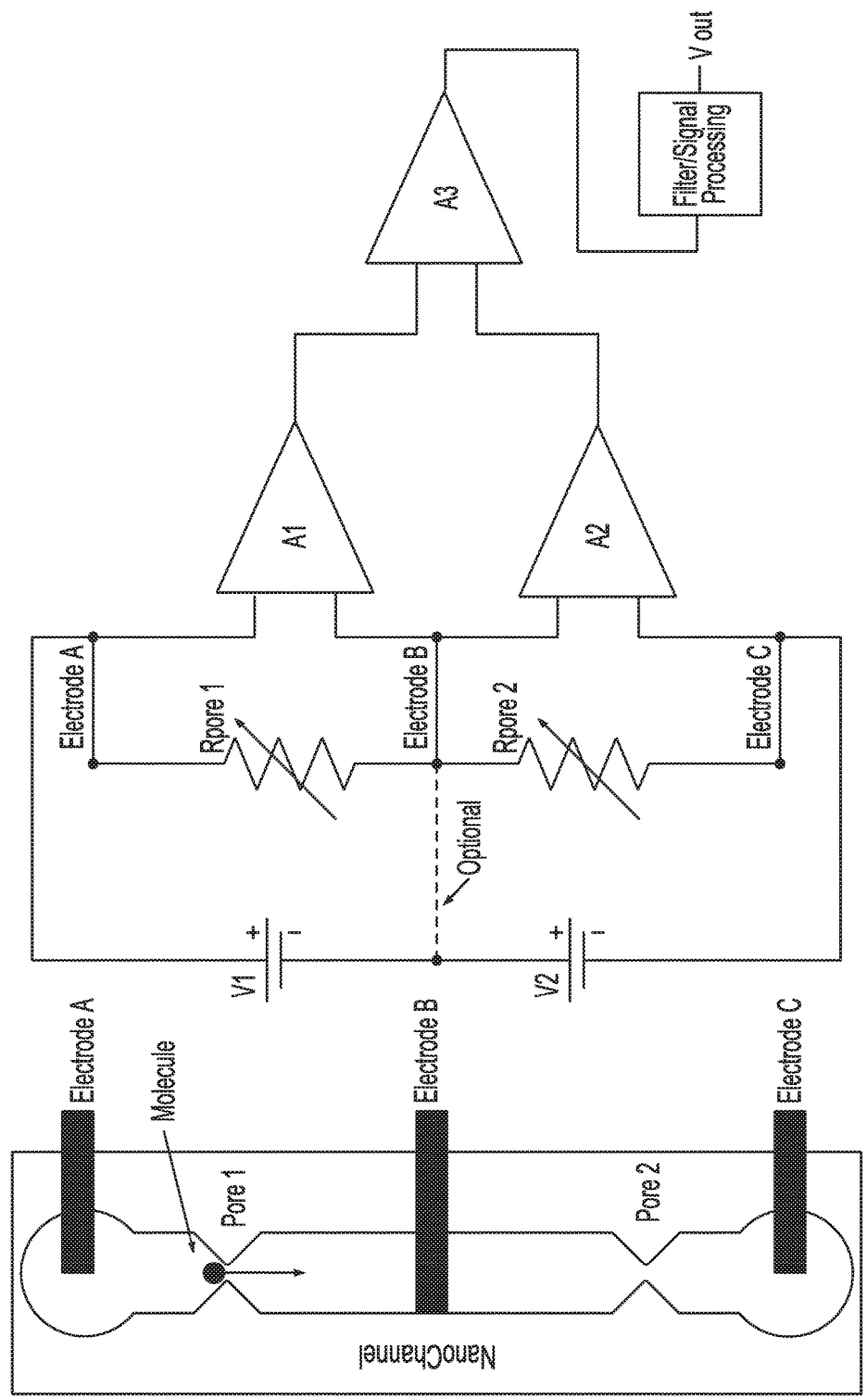
FIGS. 12A-12B show a top view of a nanotube (FIG. 12A) and a circuit diagram of the nanotube with electrodes and measuring circuitry (FIG. 12B). The circuit diagram of FIG. 12B depicts an alternative embodiment for measuring a biomolecule's identifying signature as it passes through a nanopore of the nanotube.

In FIGS. 12A-B, two DC voltage sources arranged in a bipolar fashion are used to drive molecules or particles through the nanotube. These voltage sources can be replaced by a single source, but having a bipolar source allows a mid-point connection to be used optionally as a common, or reference, in the circuitry when that may provide an advantage. This bipolar drive method also allows for different drive voltages to be applied across the two pores, allowing full differential control of speed through the individual pores. Amplifiers A1, A2, and A3 are arranged in a typical differential amplifier or instrumentation amplifier (InAmp) topology. This circuit topology can be fashioned from discrete components (transistors or OpAmps) or one of the many commercial implementations of instrumentation amplifiers can be used.

Figures 13A, 13B:
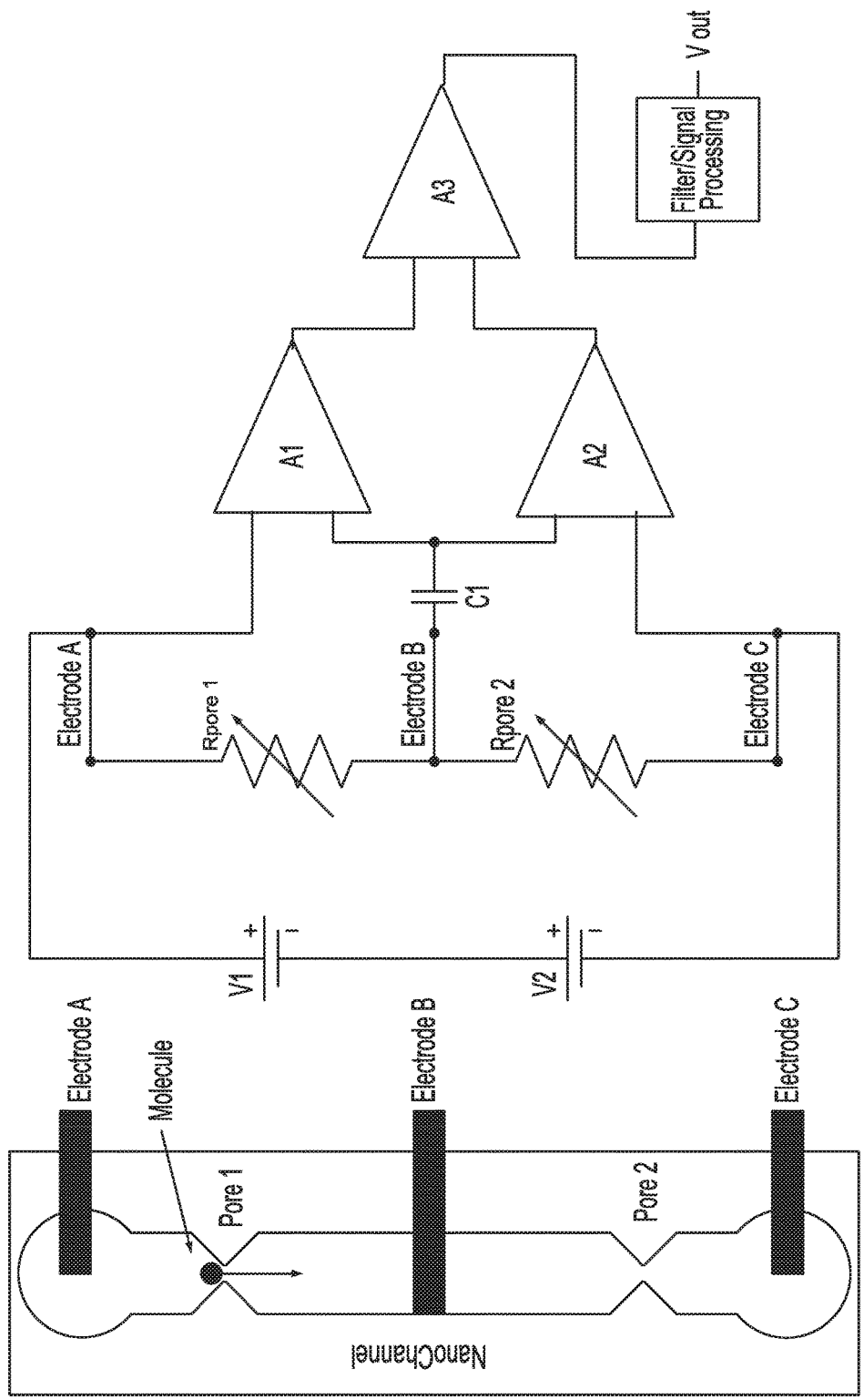
FIGS. 13A-13B show a top view of a nanotube (FIG. 13A) and a circuit diagram of the nanotube with electrodes and measuring circuitry (FIG. 13B). The circuit diagram of FIG. 13B depicts an alternative embodiment for measuring a biomolecule's identifying signature as it passes through a nanopore of the nanotube.

The embodiments depicted in FIGS. 13A-B are identical to that shown in FIGS. 12A-B, except that it shows AC coupling of the center electrode. As above, C1 can be a series coupling capacitor or it can be due to a dielectric associated with the electrode itself.

Figures 14A, 14B:
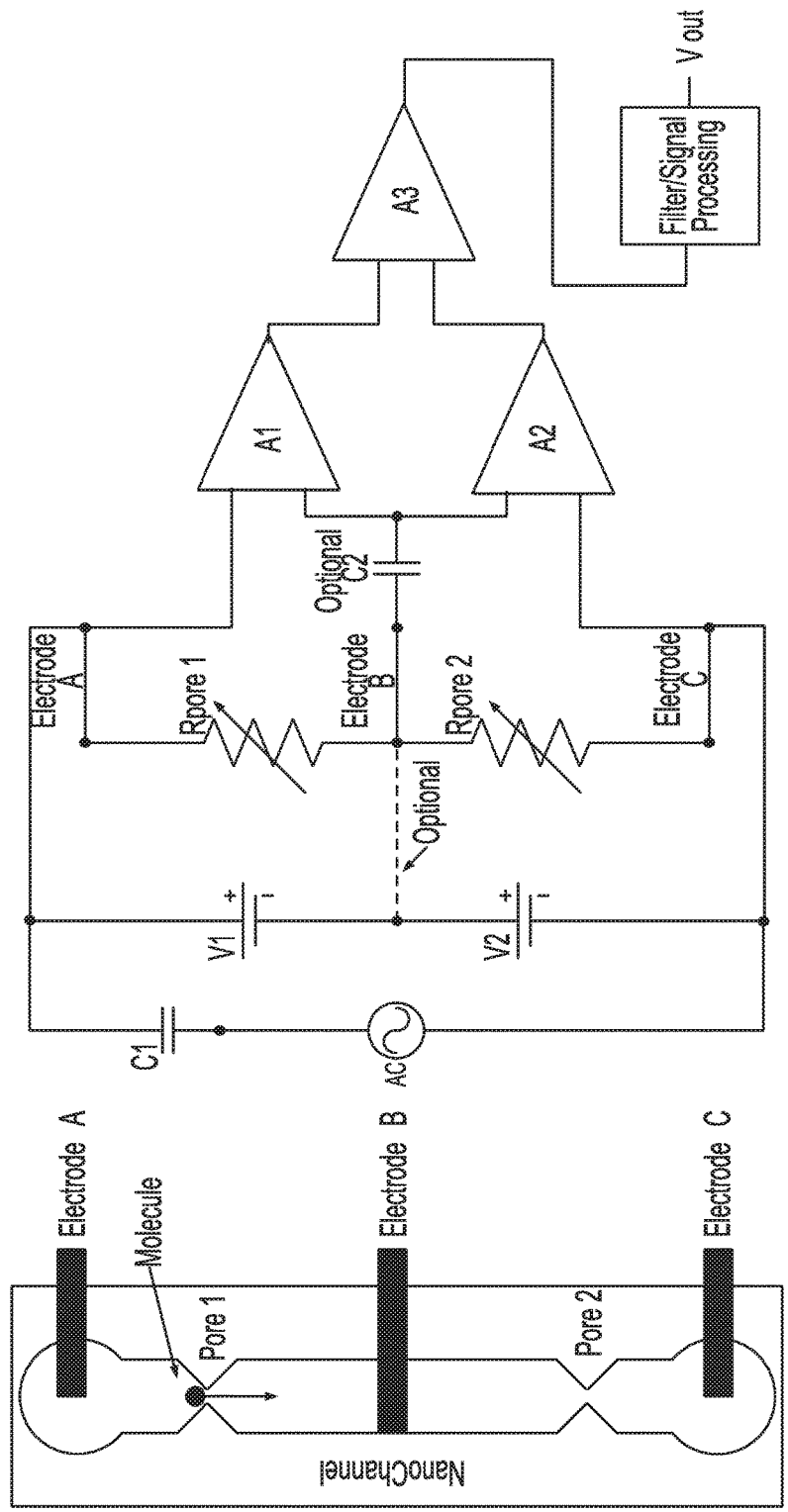
FIGS. 14A-14B show a top view of a nanotube (FIG. 14A) and a circuit diagram of the nanotube with electrodes and measuring circuitry (FIG. 14B). The circuit diagram of FIG. 14B depicts an alternative embodiment for measuring a biomolecule's identifying signature as it passes through a nanopore of the nanotube.

The embodiment shown in FIGS. 14A-B illustrates the use of a capacitively-coupled AC source superimposed on the DC drive voltage. The use of the AC source has the same advantages listed in the previous embodiments described above. The differential amplifier(s) can be either AC or DC coupled as described above through the use of C2. Filtering or signal processing can be used on the output.

FIG. 15 shows two methods for detecting and processing the blockage event signals generated by a biomolecule in a single nanotube. In both cases, amplifier A along with the filtering/signal processing can represent any of the measurement methods shown in FIGS. 7 to 14. In the method depicted in FIG. 15A, the pulse signals from blockage events at either pore are continuously converted in an Analog to Digital Convertor (ADC) and presented over a bus to the data processing/computing equipment. This requires a high conversion bandwidth for the ADC and it presents a significant amount of data to the processing equipment over time. In addition, this method collects data at the high conversion rate even when there are no blockage signals present. The data processing equipment must take this data and utilize algorithms to determine pulse height and time-of-flight. This method works well for research experiments or low-throughput analysis, but when the process is scaled up to thousands or millions of nanotubes, the data throughput becomes unsustainable. FIG. 15B shows an alternative method which allows the quantity of data required to be reduced. In embodiments where only time-of-flight data is gathered, the blockage signals can be routed to a constant fraction discriminator that provides a timing pulse for the entry blockage event and another timing pulse for the exit event. The entry pulse starts the Time Interval Counter while the exit pulse stops the counter. The Time Interval Counter then passes a single number to the data processing equipment that represents the time-of-flight. This reduces potentially millions of samples per second down to only one value for every pair of blockage events. In embodiments where the blockage event magnitude is measured, the constant fraction discriminator can be used to trigger a sample/hold and the ADC so that only a few values are converted for each blockage event. This reduces the quantity of data down to just a few points during each blockage event instead of running the ADC continuously.

Figure 16A:
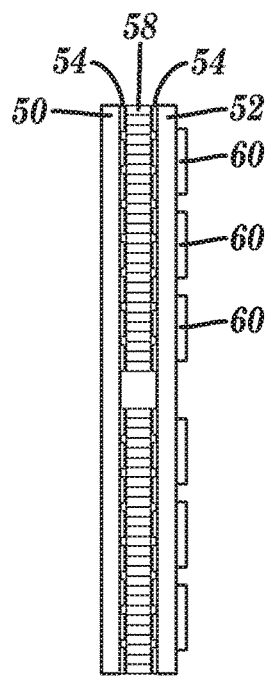
FIG. 16A is a side view and FIG. 16B is a top view of the high-density electrical connections between the nanosensor module and a printed circuit board (PCS).
Figure 16B:
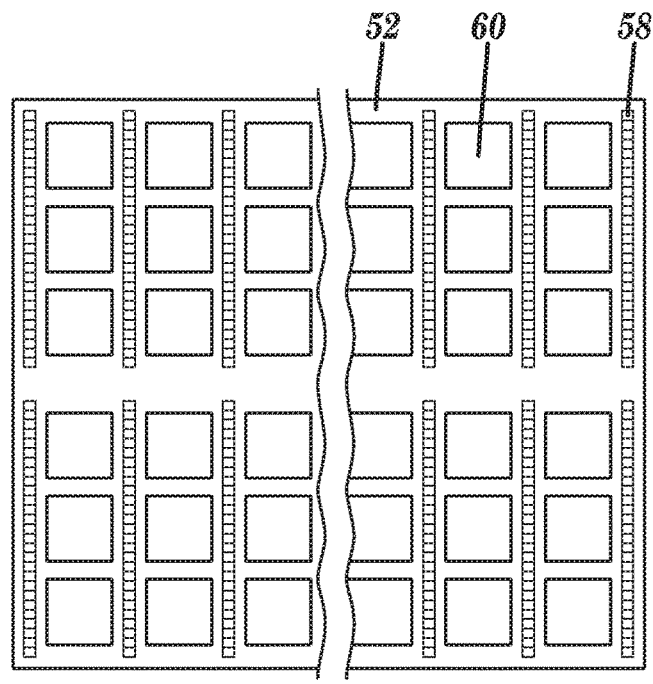

Electrical connections between the nanosensor unit and external electronic circuitry are required to measure the current transients generated when molecules travel through the in-plane synthetic nanopores. In addition, the drive voltage for producing the electrophoresis of the solid-phase generated products following release from the space solid supports of the bioreactor chamber must occur as well. FIG. 16 is a diagram showing a configuration allowing high-density electrical connections between the nanosensor unit 50 and a typical printed circuit board (PCB) 52. Gold contacts 54, 56 are plated onto the nanosensor 50 and on the PCB 52 as described below. Elastomeric ("Zebra") connectors 58 are used to make connection between the gold pads 54, 56. The elastomeric connectors 58 are commercially-available connectors comprising alternating conductive and insulating layers in a compressible elastomer. Gold pads 54, 56 with a width to accept at least two conductive layers in the elastomeric connector 58 are used to ease the alignment of the panels and the connector. The nanosensor 50 and the PCB 52 are then put under compression to make the connection. The nanosensor can be removed and replaced allowing the nanosensor to be a disposable component.

The electrical connections can be fabricated adopting the strategy described in Kong et al., *Electrophoresis* 27:2940-2950 (2006), which is hereby incorporated by reference in its entirety. In this case, the top cover plate is injection molded from the appropriate plastic to make the necessary through holes. The position of the electrical leads on the plastic plate are defined by exposing the plastic cover plate with UV/$O_3$ radiation through an optical mask that creates the carboxylic acid functional groups only at places where the plastic was exposed to the radiation. The photopatterned plate is immersed in a solution of ethylenediamine solution containing EDC for selective amination of the photolysed area. The selectively aminated substrate is sequentially immersed in an aqueous solutions of $HAuCl_4$, $NaBH_4$, and KSCN to prepare for electroless plating. Gold micro-contacts are electrolessly plated onto the selectively activated area of the plastic plate by placing the plate in a gold plating bath containing $Na_3Au(SO_3)_2$, $NaSO_3$, and formaldehyde.

To make a device of the present invention commercially useful, it is necessary that the nanosensor chambers are operated in large arrays. Accordingly, the electronics are integrated into chip form as integrated circuits (IC) with sufficient input and output channels to handle the array of nanosensor chambers. These ICs can be encapsulated using high-density technologies such as HyperBGA packaging and can be mounted on a printed circuit board (PCB).

The Universal Molecular Processor System (uMPS)

The device of the present invention may further comprise one or more units or modules defined by the solid substrate and upstream of said biomolecular processor and one or more nanotubes. The one or more additional modules are configured to carry out sample preparation and processing, i.e., isolation and preparation of target nucleic acid molecules within a sample to enter the biomolecular processor and the nanotube. An exemplary device as described herein containing a plurality of biomolecular processors and nanotubes housed together in a nanosensor unit together with a plurality of task-specific units designed to prepare a biological sample for processing and detection in the biomolecular processor and nanotube is depicted in FIGS. 17A and 17B and referred to herein as a Universal Molecular Processor System (uMPS).

Figure 17A:
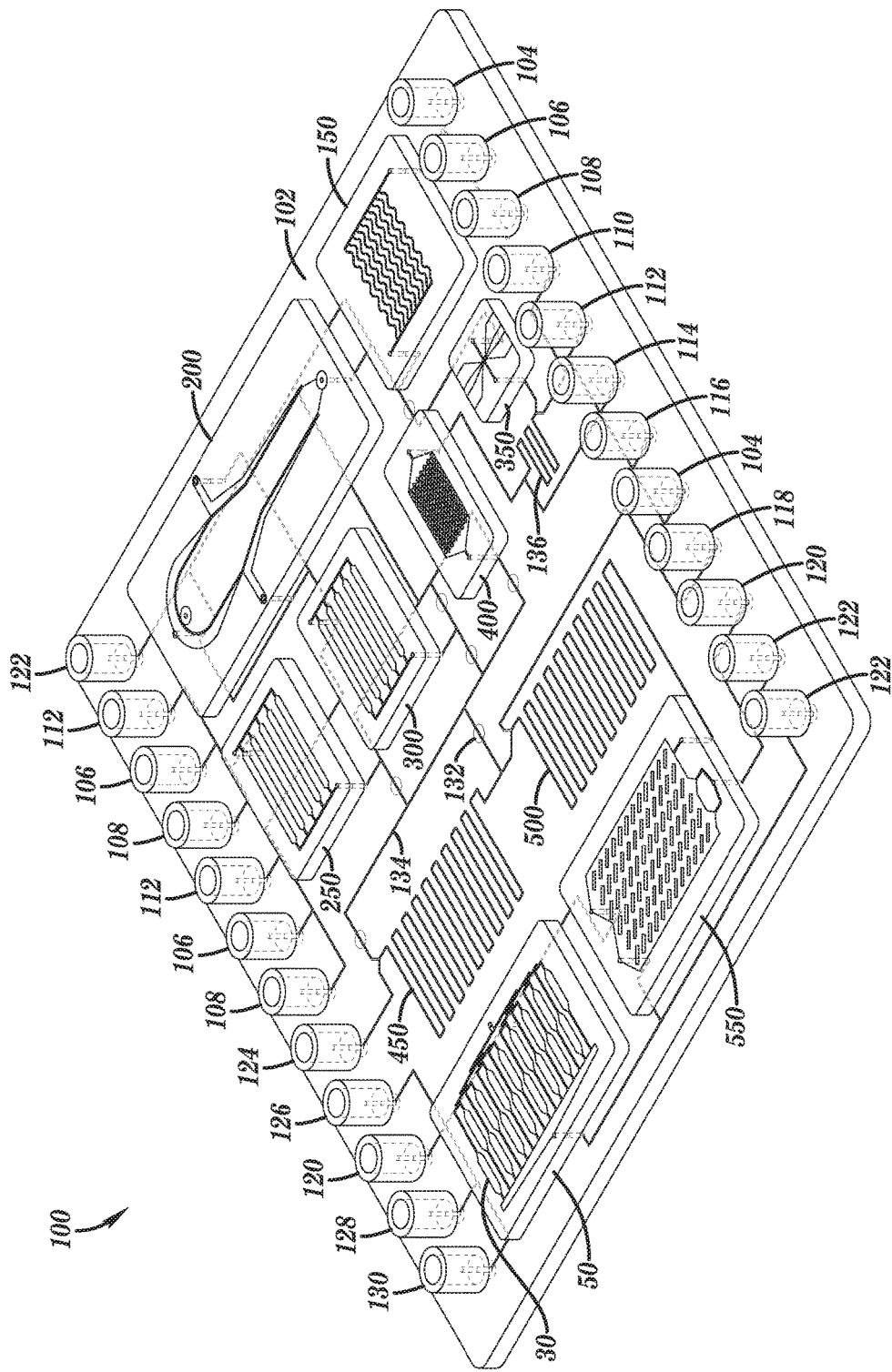
FIGS. 17A-17B are perspective and top views, respectively, of a device encompassed by the present invention. This device, which is referred to herein as a universal molecular processing system (uMPS), comprises several task specific modules that are interconnected via a fluidic motherboard.
Figure 17B:
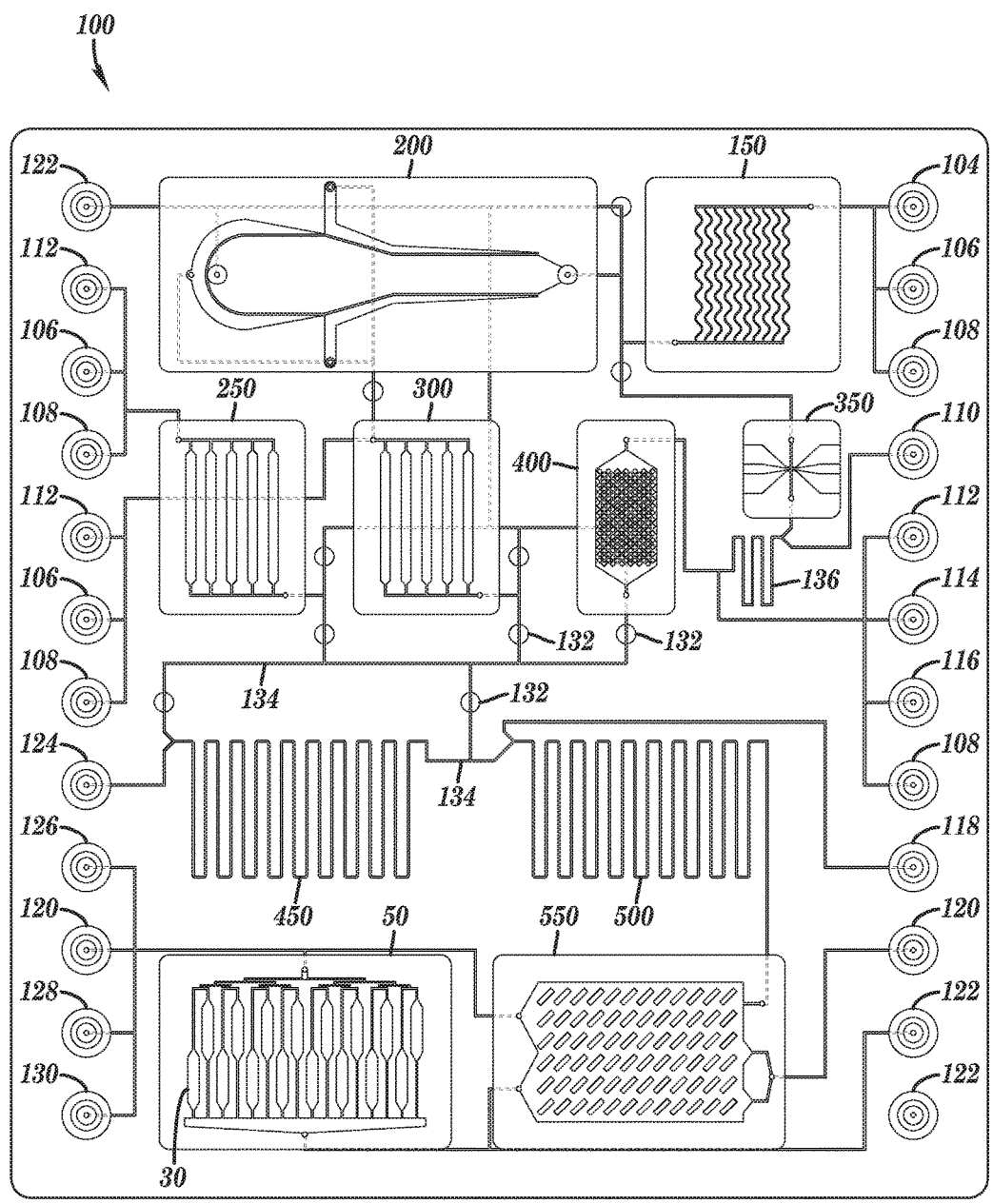

The uMPS 100 as depicted in FIGS. 17A (perspective view) and 17B (top-view) is comprised of 10 task-specific modules 150, 200, 250, 300, 350, 400, 450, 500, 550, and 50, that are connected to a fluidic motherboard 102 and organized into 3 sub-systems, which are described below. The modules are fabricated from plastics using technologies such as, but not limited to, hot embossing, injection molding, or imprinting. The particular plastic selected for each module is predicated on optimizing the task carried out on that module. These modules are connected to the fluidic motherboard using leak-free interconnects that also are engineered to minimize unswept volumes as well as degas solutions (remove air bubbles) as solutions move through the interconnects. The modules are aligned with respect to the motherboard using pins and v-grooves embossed into the substrates. The plastic surfaces are also modified using procedures to prevent non-specific adsorption artifacts.

The nanosensor module 50, depicted as the last module on the uMPS device 100 of FIG. 17A, houses the biomolecular processors and nanotubes as described supra. The nanosensor unit 50 of the uMPS houses 100-1,000,000 nanosensor chambers 30, where each nanosensor chamber houses 8 biomolecular processors and 8 nanotubes (see FIG. 1A, 30). In one embodiment, the nanosensor unit houses 2,500 nanosensor chambers, each nanosensor chamber having a dimension of ~200 µm×~410 µm.

Calculations for the footprint of 2,500 nanosensor chambers to accept 400 billion ssDNAs are shown below.
Square containing 2,500 chambers=20,000 biomolecular processors:
2,500=XY=2.05 $Y^2$; therefore Y=34.9=35
Then X=71.6
2,500 chambers fits in a 14.3×14.3 mm array=1.4×1.4 cm size=0.6×0.6 in. sq.

Square containing 25,000 chambers=200,000 biomolecular processors:
25,000=XY=2.05 $Y^2$; therefore Y=110.43
Then X=226.38
25,000 chambers fits in a 45×45 mm array, =4.5×4.5 cm size=1.8×1.8 in sq.

The calculated sizes of these numbers of nanosensor chambers poised on the nanosensor module 50 will allow this module to easily fit onto a 6" wafer comprising the uMPS 100 and provide sufficient space to accommodate the other processing modules 150, 200, 250, 300, 350, 400, 450, 500, 550 as depicted in FIGS. 17A-17B.

Depending on the application of the uMPS, it may be desirable to maximize the number of biomolecular processors per uMPS device. Thus, in one embodiment, the nanosensor chamber can be streamlined to exhibit dimensions of 175×175 μm, containing 8 biomolecular processors, each in a 25×16 μm footprint (each biomolecular processor with 288 pillars). With 5 μm spacing between 16 μm biomolecular processors×8+5 μm wall=175 μm wide. Input area 25 μm+Chevron baffles 50 μm+25 μm biomolecular processors+50 μm flight tube+20 μm space+5 μm for wall=175 μm.

A 4×4 inch wafer=101.6 mm×101.6 mm. That means 580×580=336,400 chambers×8 biomolecular processors=2,691,200 biomolecular processors. Therefore, in this embodiment, a 4×4 inch wafer contains about 336,000 chambers and 2,600,000 biomolecular processors.

A 6×6 inch wafer=152.4 mm×152.4 mm, but using only 135 mm (5.3 inches) per side=135 mm×135 mm. That means 771×771=594,441 chambers×8 biomolecular processors=4,755,528 biomolecular processors. Therefore, in this embodiment, a 6×6 inch wafer contains about 600,000 chambers and 4,700,000 biomolecular processors.

The device of the present invention may contain any one or more of the task-specific units (also referred to as modules) depicted on the uMPS device of FIGS. 17A and 17B in combination with the nanosenor unit housing the biomolecular processors and nanotubes. The particular combination of units depends on the desired function of the uMPS (i.e., the sample being analyzed (e.g., exosome vs. cfDNA vs. RNA) and the endpoint being analyzed (e.g., mutation detection, copy number enumeration, methylation detection, sequencing, etc)). In one embodiment of the present invention, the device contains all of the modules of the uMPS device as depicted in FIGS. 17A and 17B. Depending on the particular application of the device, only select modules are utilized when processing a particular sample, i.e., not all modules on the device need to be employed for sample analysis. For example, in one embodiment, 1, 2, 3, 4, 5, 6, 7, 8, or all 9 of the modules of the uMPS device can be utilized for any given application in combination with the nanosensor module 50. The flow of the sample to, through, and/or away from various modules of the device is conducted through the microfluidic network 134 of the motherboard 102, and controlled by a series of valves 132 located throughout the microfluidic network. Reagent 108-114, 118, 120, 124-130, wash 106, air 116, and waste 122 reservoirs line opposing outside edges of the motherboard facilitating the delivery and removal of reaction components to the various task-specific modules.

In reference to FIG. 17A, the first sub-system of the uMPS device is comprised of 6 modules, and is capable of manipulating a sample of blood entering the device at the sample input port 104 to isolate target biological cells (e.g., circulating tumor cells (CTCs), immune cells, etc.) or microbial pathogens, via the cell selection module 150, separate plasma from red and white blood cells via the plasma isolation unit 200, and extract cfDNA and/or select exosomes from the plasma via the solid-phase extraction modules 250 and 300, respectively. The other two modules for this sub-system consist of an impedance sensor 350 that is used to count individual cells released from the cell selection module, and a solid-phase extraction module 400 for capturing DNA/RNA released from lysed biological cells selected from whole blood.

Figure 18A:
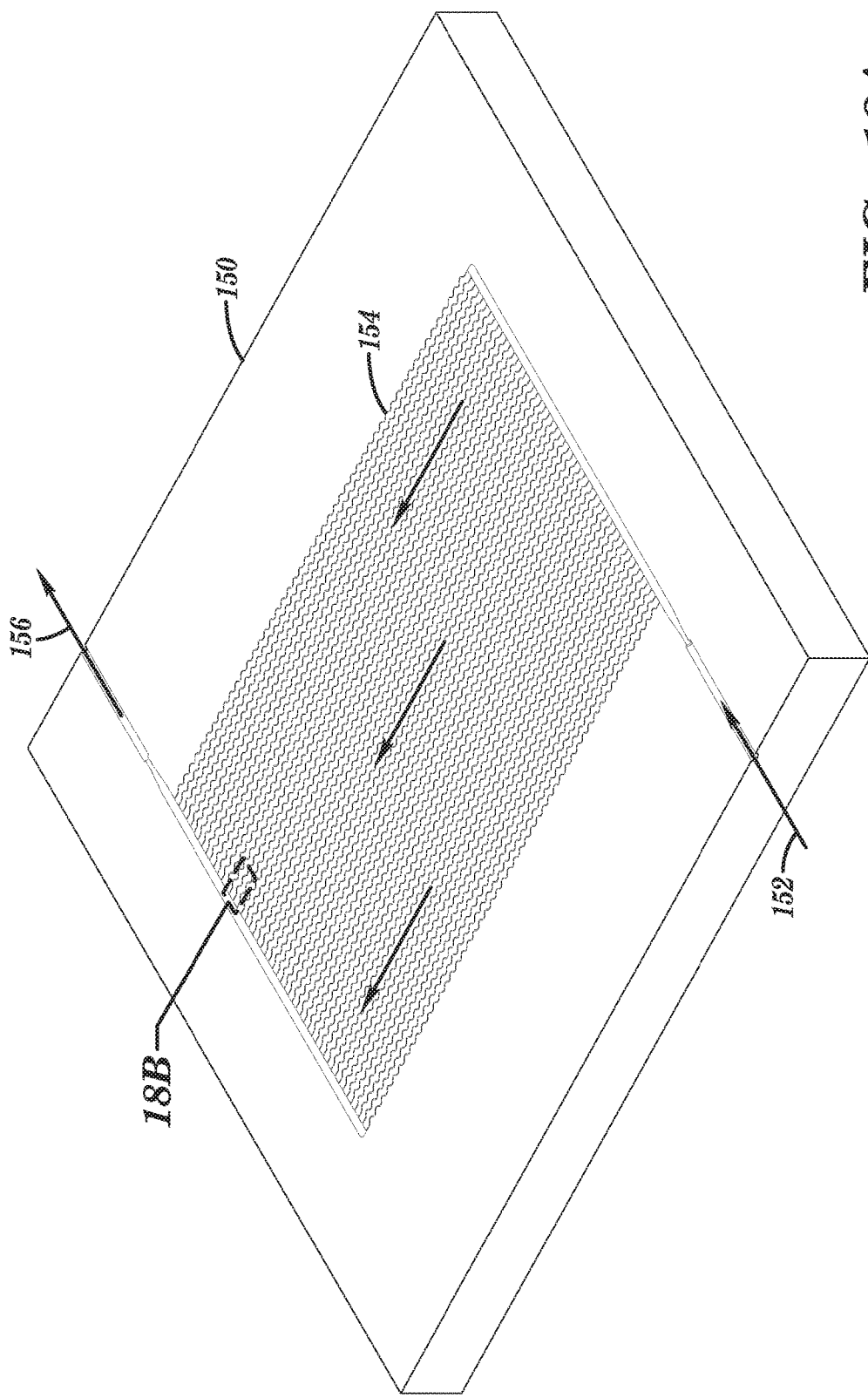

A perspective view of the cell selection module 150 is shown in FIG. 18A. The module consists of an input port 152, a capture bed 154, and an output port 156. A magnified perspective view of the capture bed 154 is shown in FIG. 18B. As shown in this figure, the capture bed comprises a multitude of parallel channels 160, where the channels have a sinusoidal, quasi-sinusoidal, or other meandering channel shape used to enhance contact between cells in the fluid sample and channel walls 162. The channels have a high aspect ratio (3:1 or more), with a width that is on the order of 1-2 times the target cell diameter. The channel walls are decorated with monoclonal antibodies, aptamers, or other binding molecules specific for a targeted cell type (Kamande et al., *Anal. Chem.* 85:9092-9100 (2013) and Pullagurla et al., *Anal. Chem.* 86:4058-4065 (2014), which are hereby incorporated by reference in their entirety). Following sample flow through, the target cells bound to the channel walls of the selection module 150 are washed via wash fluid from the wash reservoir 106 (see FIG. 17B).

Figure 19:
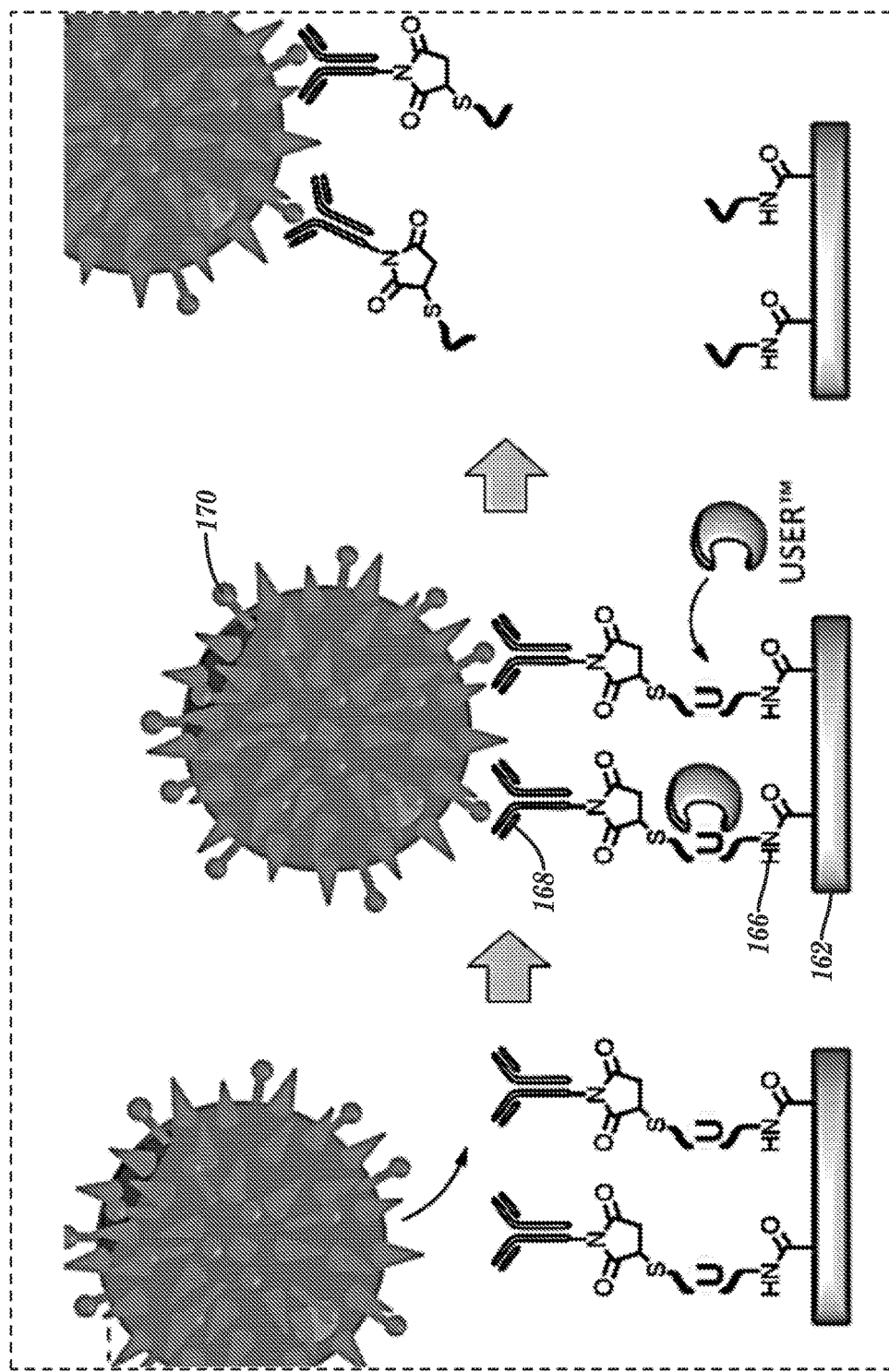
FIG. 19 is a schematic drawing of the capture antibodies immobilized to channel walls of the cell isolation module. The antibodies are immobilized using cleavable oligonucleotide linkers.

To selectively release target cells after capture and washing, the monoclonal antibody, aptamer, or other affinity agent utilized to capture the target cells is attached to the channel wall surface via an oligonucleotide with a heterobifunctional linker (SMCC) as depicted in FIG. 19. In one embodiment, oligonucleotide linkers contain a modified nucleotide, e.g., uridine or photocleavable residue, that is cleaved enzymatically to release target cells bound by the antibody or aptamer. The release buffer containing the cleaving enzyme is housed in the release reservoir 108 adjacent the cell isolation module 150 as depicted in FIGS. 17A and 17B. The use of oligonucleotide linkers is attractive because they are low-cost, release efficiency is >93%, and >90% of the released cells remain viable. In addition, due to the selective action of USER (Uracil-Specific Excision Reagent), cells that non-specifically attached to the channel wall surface are not released. The immobilization of affinity capture molecules, e.g., antibodies or aptamers, to the channel walls of the cell selection module involves UV/$O_3$ (254 nm) irradiation of a thermoplastic to produce surface-confined carboxylic acids for the covalent attachment of the oligonucleotide through a 5' amino group; the sulfhydryl on its 3' end reacts with the SMMC/affinity conjugate.

Other methods for releasing affinity-selected cell targets can alternatively be employed, for example release of CTCs from affinity agent-decorated solid surfaces can be achieved using trypsinization (Dharmasiri et al., *Anal. Chem.* 83:2301-2309 (2011); Kamande et al., *Anal. Chem.* 85:9092-9100 (2013); Adams et al., *J. Am. Chem. Soc.* 130:8633-8641 (2008); and Sheng et al., *Lab Chip.* 14:89-98 (2014)), hydrogels (Hatch et al., *Langmuir* 27:4257-4264 (2011); Yu et al., *Small* 9:3895-3901 (2013); and Shah et al., *Anal. Chem.* 84:3682-3688 (2012), which are hereby incorporated by reference in their entirety), mediated magnetic release (Yu et al., *Small* 9:3895-3901 (2013), which is hereby incorporated by reference in its entirety), exonuclease digestion of aptamers (Chen et al., *Adv. Materr* 23:4376-4380 (2011) and Shen et al., *Adv. Mater.* 25:2368-2373 (2013), which are hereby incorporated by reference in their entirety), or PGLA nanofibers with sections removed via laser-microdissection (Hou et al., *Angew Chem. Int. Ed. Engl.* 52:3379-3383 (2013), which is hereby incorporated by reference in its entirety).

The cell selection module is fabricated using a plastic and produced via micro-replication. Methods of making and using the cell selection module depicted in FIG. 18 are described further in U.S. Patent Publication No. 20120100521 to Soper et al., Dharmasiri et al., *Analytical Chem.* 83:2301-2309 (2011); and Jackson et al., *Lab Chip* 14(1): 106-107 (2014), which are hereby incorporated by reference in their entirety. Alternative nanostructured cell selection modules that are suitable for use on the uMPS device of FIG. 17 are known in the art, see e.g., (Lim et al., *Lab Chip.* 12:4388-4396 (2012); Wang et al., *Angew Chem. Int. Ed. Engl.* 50:3084-3088 (2011); Wang et al., *Angew Chem. Int. Ed. Engl.* 50:3084-3088 (2010); Stott et al., *Proc. Nat'l. Acad. Sci. U.S.A.* 107:18392-18397 (2010); Lin et al., *Clin. Cancer Res.* 16:5011-5018 (2010); Hosokawa et al., *Anal. Chem.* 82:6629-6635 (2010); Xu et al., *Anal. Chem.* 81:7436-7442 (2009); and Tan et al., *Biomed. Microdev.* 11:883-892 (2009), which are hereby incorporated by reference in their entirety).

The device of the present invention may further comprise a longitudinally-extending plasma isolation unit that is defined by the solid substrate and upstream of the biomolecular processor and one or more nanotubes. The longitudinally-extending plasma isolation unit comprises an entrance passage, a discharge passage which is wider than the entrance passage, and a transition passage connecting the entrance passage and the discharge passage. The transition passage becoming wider and shallower as the transition passage progresses from the entrance passage to the discharge passage. The plasma isolation unit also comprises primary side channels extending laterally away from the entrance passage, where a separator, positioned between the entrance passage and each primary side channel, is sized to permit plasma, but not cells, to pass from the entrance passage to the primary side channels. The plasma isolation unit also comprises secondary side channels extending laterally away from the discharge passage, where a separator, positioned between the discharge passage and each secondary side channel, is sized to permit plasma, but not cells, to pass from the entrance passage to the secondary side channels.

The plasma isolation unit 200 is located adjacent to the cell isolation unit 150 on the uMPS device of FIG. 17A. An exemplary plasma isolation unit is depicted in FIGS. 20A-20D. As shown in FIG. 20A, the plasma isolation unit comprises a primary tapered isolation channel (i.e., entrance passage) 204 that opens to a wider secondary isolation channel (i.e., discharge passage) 208. The cross-section of FIG. 20D, which is taken through line 20D-20D of FIG. 20A, shows that the primary isolation channel 204 having a depth of about 130 μm that allows for high flow rate plasma removal. A transition channel 206 which serves as size selection filter connects the deeper primary isolation channel 204 to the secondary channel 208 having a depth of only about 30 μm (see FIG. 20D). Primary side channels 210 are used to collect and transport plasma that are separated from the blood sample that enters the plasma isolation module via the input port 202. FIG. 20B, is a cross-section through line 20B-20B of FIG. 20A, showing the primary channel side port 228 (~2 μm tall), which runs the length of the primary channel 204 and transition channel 206, and opens into the primary side channel 210. In reference to FIG. 20B, the primary channel side port 228 is formed from a primary separator 212 that is positioned between the primary isolation channel 204 and the primary side channels 210. The primary separator 212 is sized to permit plasma, but not cells to exit the primary channel 204 via the primary channel side ports 228, into the primary side channels 210. The primary side channels 210 lead to the primary receiver ports 216 that collect the plasma and its constituents (e.g., exosomes, cfDNA and ions), while the cellular materials, such as erythrocytes and leukocytes, are transported along the filtration wall and toward the waste port 224. Plasma that has entered the secondary isolation channel (i.e., the discharge passage) 208, likewise exits the secondary isolation channel 208, via the secondary channel side ports 230 and flows into the secondary side channels 218 for collection in the secondary receiver port 226. The secondary channel side port 230 is formed from a secondary separator 220 that is positioned between the secondary isolation channel 208 and the secondary side channels 218. The secondary separator 220 is sized to permit plasma, but not cells to exit the secondary channel 208 via the secondary channel side ports 230, into the secondary side channels 218. The cellular material which does not pass through the secondary side channel ports 230 travels along the secondary channel wall toward the waste port 224. FIG. 20C is a cross-section through line 20C-20C of FIG. 20A showing the secondary channel 208, the secondary side channel port 230, the secondary separator 220, and the secondary side channel 218. Plasma collected in the primary and secondary receiver ports is sent onto other processing modules, e.g., the extractor units for exosome and cfDNA isolation. The removal efficiency and plasma recovery rate are affected by adjusting the flow rates at the receiver ports 216, 226.

The primary, secondary, and side channels are sealed with a cover plate 232 using thermal fusion bonding. Two syringe pumps operating in suction mode at the primary 216 and secondary 226 side receiver ports, and the waste outlet 224 fluidically controlled the system. Waste from the plasma isolation unit exits the unit and is collected in the waste reservoir 122 on the uMPS (FIG. 17A).

Figure 21A:
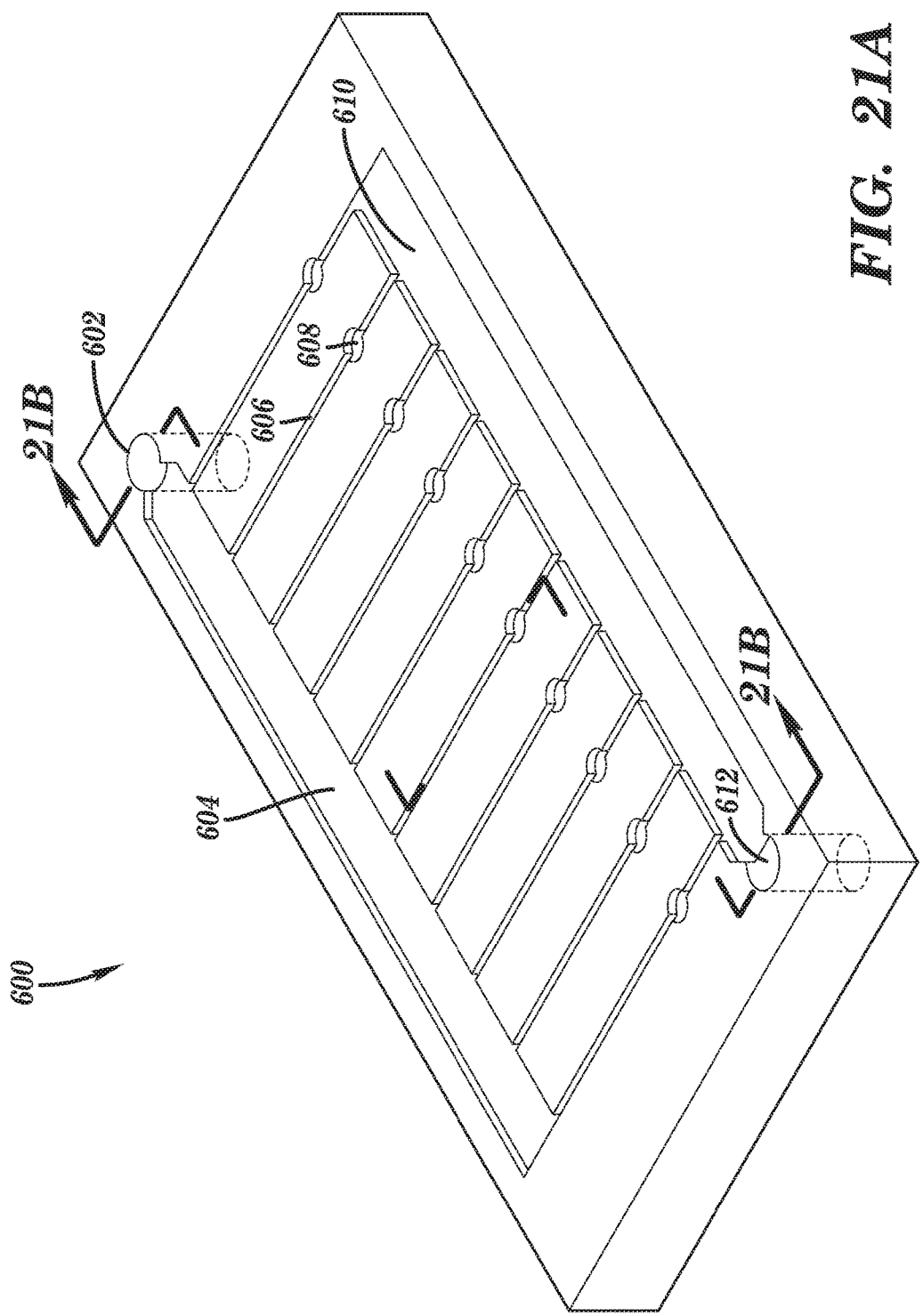
FIGS. 21A-21B depict an alternative plasma isolation module of the uMPS.
Figure 21B:
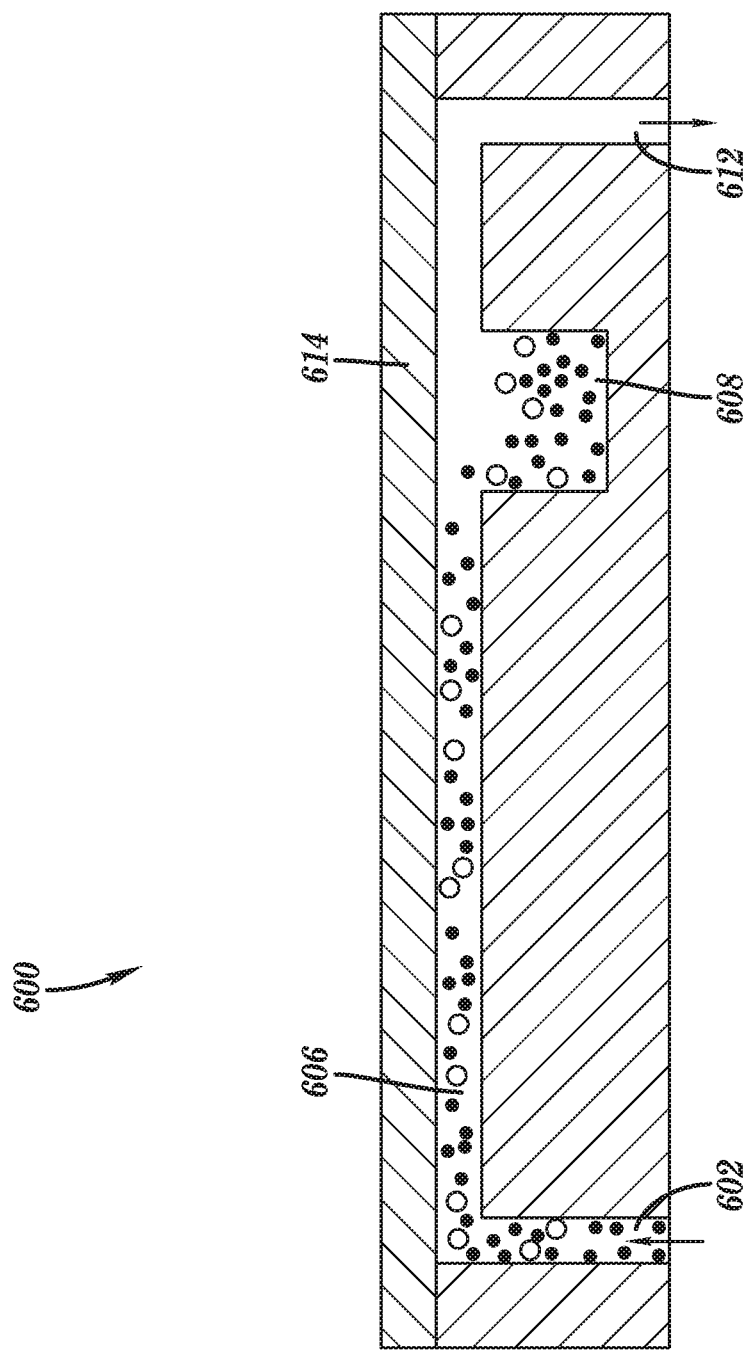

An alternative plasma isolation module is depicted in FIGS. 21A-21B. This device separates white blood cells and red blood cells from plasma containing exosomes and cell free DNA based on differences in sedimentation as previously described by Dimov et al., *Lab on a Chip,* 11: 845-850 (2011), which is hereby incorporated by reference in its entirety. The perspective view of FIG. 21A shows an exemplary alternative plasma isolation module 600 that consists of an input port 602 and feeder channel 604. The feeder channel 604 intersects with a series of parallel isolation channels 606, each isolation channel containing a blood cell trap 608. FIG. 21B, which is a cross-sectional view through from line 21B-21B of FIG. 21A, shows the input port 602, where a whole blood sample enters the module, and one of the parallel isolation channels 606 containing a trap 608. Each trap is ~1 cm in depth, has a diameter of 0.24 cm, and a total volume of ~0.045 mL. As the sample travels through the isolation channel, the blood cells are retained in the cell trap 608, while the plasma and its constituents (e.g., exosomes, cfDNA and ions) exit the isolation channel flowing into the common exit channel 610 and out of the module via the output port 612.

To increase throughput and the amount of blood cells that can be collected, ten isolation channels 606, each containing a cell trap 608 are placed in a z-configuration, parallel arrangement as shown in FIG. 21A. The feeder channel 604 has a large cross-sectional area that fills with blood before the blood enters each isolation channel 606 containing the trap 608 due to the lower fluidic resistance in these larger channels. For a device that contains 10 traps, the volume throughput is 0.25 ml/s and the total volume of blood cells that can be contained in the traps is 0.45 mL.

In one embodiment, the device of the present invention further comprises one or more extractor units. Each extractor unit is defined by the solid substrate and located upstream of the biomolecular processor and one or more nanotubes. The extractor unit comprises solid supports with passages between them, where the solid supports are provided with a material suitable to immobilize nucleic acids or exosomes or vesicles.

Figure 22:
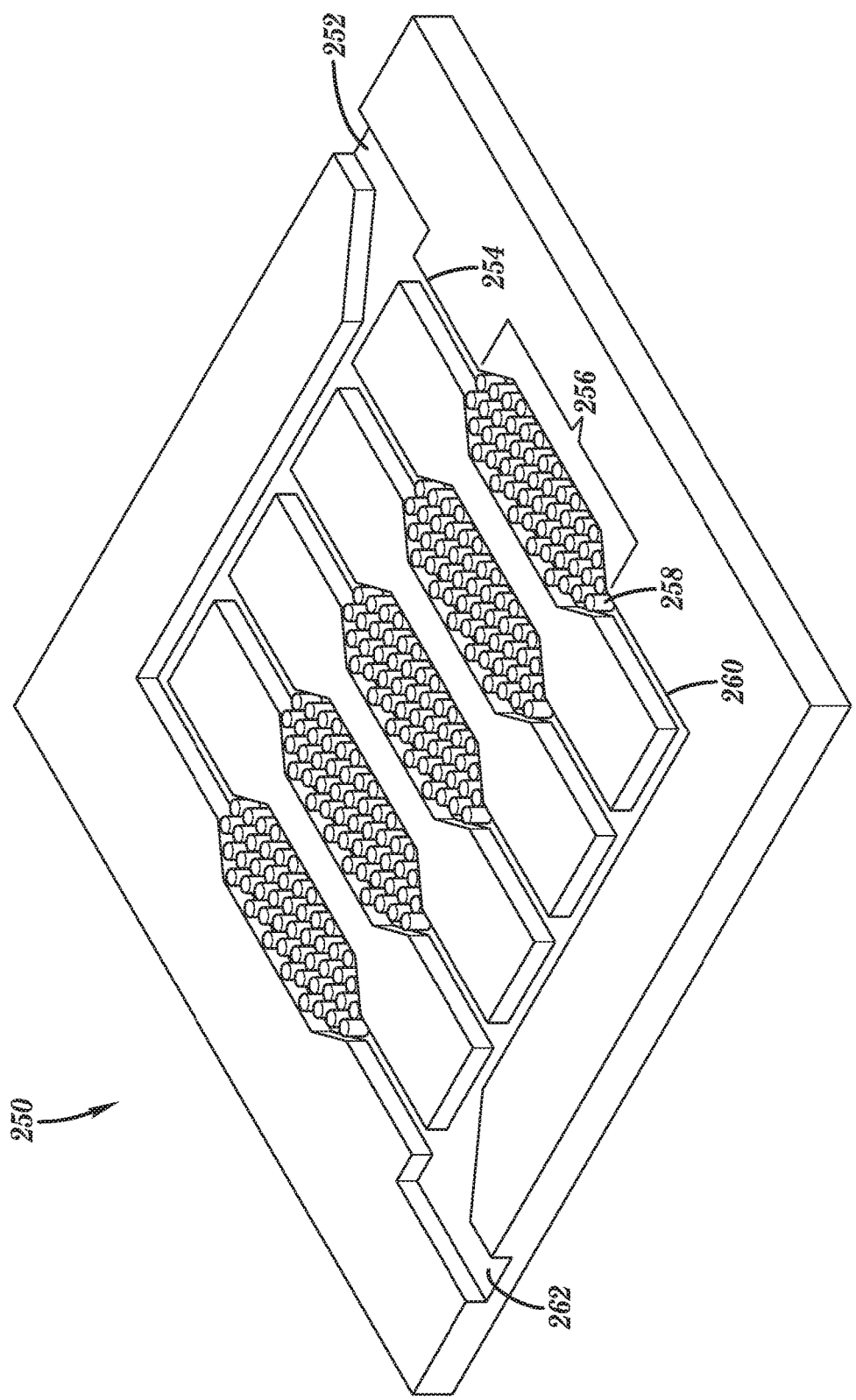
FIG. 22 is a perspective view of a solid phase extractor (SPE) module of the uMPS used for exosome or cfDNA isolation.

The extractor units are depicted as modules 250 and 300 of the uMPS shown in FIGS. 17A and 17B, where module 250 is suitable for exosome extraction and module 300 is suitable for nucleic acid extraction. Structurally, these modules are the same, and an exemplary extractor unit 250 is depicted in FIG. 22. These modules differ in the material on the solid supports that is used to immobilize the desired target (i.e., exosome or nucleic acid). With reference to the embodiment illustrated in FIG. 22, the extractor unit 250 comprises an input channel 252 that intersects with a series of parallel channels 254, each channel containing at least one extraction bed 256. While the extractor unit 250 of FIG. 22 is shown with a series of five extraction beds 256 arranged in parallel, the extractor unit 250 can readily be designed to hold more than ten extraction beds in the same parallel configuration. Arranging the extraction beds in parallel provides uniform addressing of all beds with a constant flow velocity when tapering the extractor bed feeder channel 254 and the extractor bed exit channels 260. In addition, within a single extraction bed 256, the entire circumference of the solid support 258 is uniformly accessible by the target (Battle et al., *Analyst* 139:1355-1363 (2014), which is hereby incorporated by reference in its entirety). The solid supports 258 of the extractor bed 256 can be, for example and without limitation, pillars (e.g., polycarbonate pillars), beads (e.g., silica beads) (Breadmore et al., *Anal. Chem,* 75:1880-1886 (2003), which is hereby incorporated by reference in its entirety), reactive ion etched silica pillars (Christel et al., *J. Biomech. Engin.* 121:22-27 (1999), which is hereby incorporated by reference in its entirety), or resins (Tian et al., *Anal. Biochem.* 283:175-191 (2000), which is hereby incorporated by reference in its entirety). The passages between the solid supports can have any desired configuration, e.g., a sinusoidal configuration. As sample flows through the extraction bed 256, target molecule, e.g., exosomes or cfDNA is captured on the solid support via the appropriate immobilized affinity agent. The remainder of the sample exits the extractor bed via the output channel 260, and the SPE module 250 via the common SPE module output channel 262. In reference to FIGS. 17A and 17B, the extractor units 250, 300 are fed immobilization buffer, wash, and release reagents from adjacent reservoirs 112, 106, and 108, respectively, on the motherboard of the device 100.

In one embodiment, the extractor unit is made from polycarbonate with extraction beds populated with micropillars as disclosed in U.S. Patent Application Publ. No. 20040191703 to Soper et al., which is hereby incorporated by reference in its entirety. Polycarbonate solid phase extraction (SPE) beds such as these can be fabricated using a single replication step with bed preparation requiring only UV/$O_3$ irradiation (Witek et al., *Nucl. Acids Res.* 34(10):e74 (2006), which is hereby incorporated by reference in its entirety). The pillar/bead diameters and spacing are varied to optimize target molecule recovery.

To selectively release target molecules (e.g., exosome or nucleic acids), affinity agents can be attached to support surfaces via an oligonucleotide and affinity agent modified with a hetero-bifunctional linker (SMCC) containing a cleavable nucleotides as described above with regard to the cell isolation unit and depicted in FIG. 19. As described supra, the immobilization of the affinity capture agents involves UV/$O_3$ (254 nm) irradiation of a thermoplastic to produce surface-confined carboxylic acids for the covalent attachment of the oligonucleotide through a 5' amino group; the sulfhydryl on its 3' end reacts with the SMMC/affinity conjugate.

An extractor unit suitable for extracting exosomes employs affinity selection reagents specific for circulating exosomes. In this module, the pillars are decorated with antibodies or aptamers specific for exosomes. For example, the pillars may be decorated with antibodies or aptamers specific for CD63 or RAP5 proteins that are expressed on circulating exosome population (Clayton et al., *J. Immunol. Methods* 247:163-174 (2001); Zhou et al., Methods S1046-2023(15):30130-4 (2015), which are hereby incorporated by reference in their entirety). Alternatively, the pillars may be decorated with antibodies or aptamers specific for EpCAM, Her2/neu, or separase for selecting tumor-related exosomes from a sample. In one embodiment, the exosome extractor module is made from COC because this material can be efficiently UV-activated to provide high loads of functional groups in the form of surface-confined carboxylic acids even for high aspect ratio structures (Jackson et al., "UV Activation of Polymeric High Aspect Ratio Microstructures: Ramifications in Antibody Surface Loading for Circulating Tumor Cell Selection," *Lab on a Chip* 14:106-117 (2014), which is hereby incorporated by reference in its entirety).

An exemplary extractor unit suitable for extracting cfDNA may comprise a polycarbonate SPE bed that has been UV activated to isolate short DNAs, similar in size to cfDNA. The efficiency of cfDNA isolation is dependent on the composition of the immobilization buffer. In one embodiment, a suitable immobilization buffer comprises of Polyethylene Glycol (PEG), sodium chloride (NaCl), and ethanol (EtOH).

In one embodiment, the device of the present invention further comprises a sensor unit defined by the solid substrate and upstream of the biomolecular processor and the one or more nanotubes. The sensor unit comprises an inlet and an outlet and is configured to count cells passing through the sensor unit. The sensor unit also comprises a pair of electrodes and a fluidic channel. The fluidic channel is between the pair of electrodes and fluidically coupled to said separator unit.

Figure 23B:
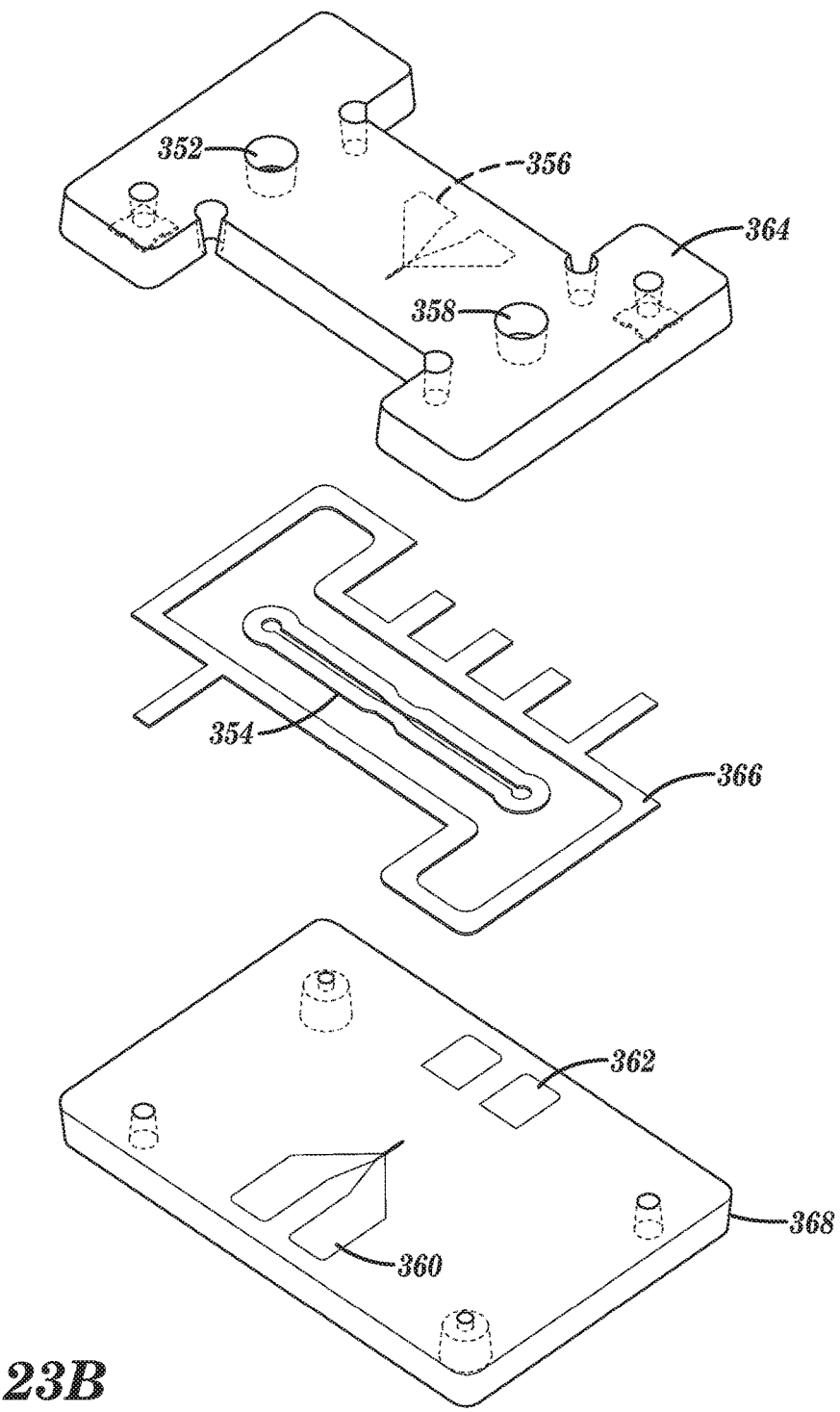

The sensor unit of the device is depicted as module 350 of the uMPS as shown in FIGS. 17A and 17B. An exemplary sensor unit, also referred to as an impedance unit, is depicted in FIGS. 23A and 23B. The impedance module is used to enumerate cells released from upstream units of the device and determine their viability.

An exemplary impedance module suitable for incorporation into the device as described herein or as a stand-alone module is a 3-layered module that consists of electrodes on the top and bottom face of a fluidic channel. A perspective view of this module is depicted in FIG. 23A, and the exploded view of FIG. 23B shows the individual layers of the device. As shown in these Figures, the first layer or top layer 364 has a top and bottom surface, where the inlet 352 and outlet 358 ports are located on the top surface of the first layer. The first layer 364 also has microelectrodes 356 on its bottom surface that intersect with the microfluidic channel 354 of the middle layer 366 in the assembled module. The second or bottom layer 368 of the impedance unit 350 also has top and bottom surface. The second layer 368 has microelectrodes 360 on its top surface that intersect with the microchannel 354 of the middle layer opposite the microelectrodes 356 located on the bottom surface of the first layer 364 in the assembled unit. The top surface of the second (bottom) layer also has contact pads 362 that contact the microelectrodes 356 on the bottom surface of the first (top) layer 364 in the assembled unit. The second layer also contains female, conical ports used for interconnecting the impedance module to the fluidic motherboard. The middle layer 366 of the module comprises a thin plastic layer containing the microfluidic channel 354. The middle layer sets the spacing between the microelectrodes 356, 360 of the first and second layers, respectively. A section of the microfluidic channel serving as the detection volume has a through-hole to allow for solution electrical contact with both the top 356 and bottom 360 electrodes.

In use, the impedance module enumerates cells released from the upstream capture surface of the cell separation module, and also determines their viability. A cell containing sample enters the impedance module 350 via the input port 352 and travels through the microchannel 354 passing between the microelectrodes 356, 360. The signal measured by the module is proportional to the resistance of the medium between the electrodes. When no cell is present between the electrodes the signal is proportional to the resistance of the buffer solution and this defines the baseline for the measurements. Every cell passing between the electrodes replaces a small volume of the buffer solution. Intact cells are considered non-conductive at the frequency of the electrical signal (40 kHz) applied between electrodes due to high cell membrane capacitance. Thus, the small volume of the solution replaced by the cell has higher resistance than the corresponding volume of the buffer alone. This leads to an increase in the overall resistance measured by impedance sensor, which presents itself as positive peaks recorded for a passing cell (see FIG. 44A). When the cells' membrane is compromised, the cell resistance can be approximated by the resistance of the cell interior, which is composed primarily by cytoplasmic components. If the resistance of cell cytoplasm is lower than that of the corresponding volume of buffer solution, the overall resistance measured by sensor drops, which results in a negative peak (see FIG. 44B).

Figure 24:
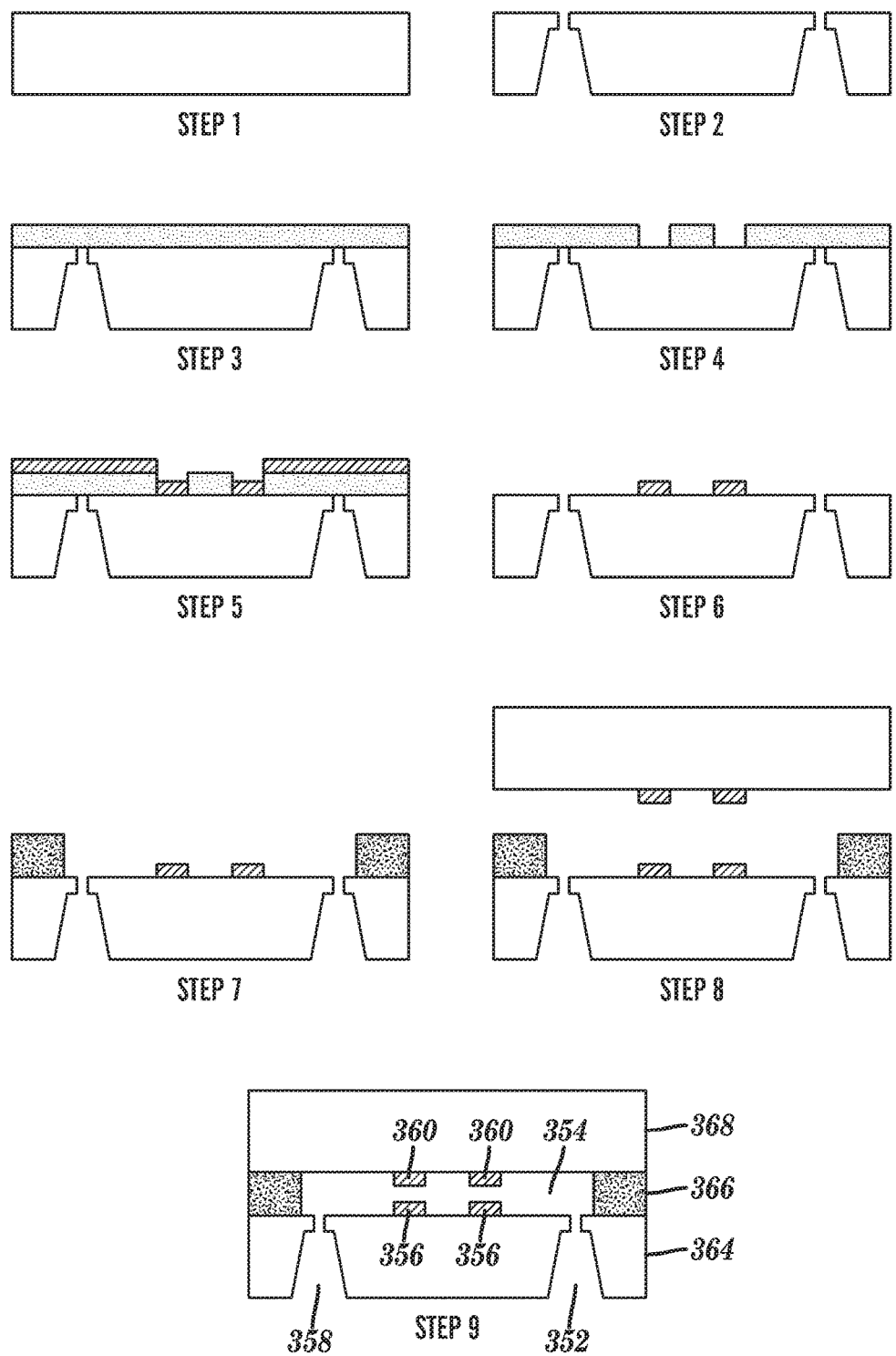
FIG. 24 shows the process of making the impedance module depicted in FIGS. 23A-23B.

FIG. 24 provides a schematic overview of an exemplary fabrication method employed to produce the impedance module depicted in FIGS. 23A and 23B. This fabrication modality does not require manual insertion of platinum wires into prefabricated channels (Adams et al., *J. Am. Chem. Soc.* 130:8633-8641 (2008) and Galloway et al., *Anal. Chem.* 74: 2407-2415 (2002), which are hereby incorporated by reference in their entirety). In steps 1 and 2, the top and bottom covers of the module comprising cyclic olefin copolymer (COC) are prepared using hot-embossing or injection molding. In steps 3 and 4, photolithography or electroless deposition is used to pattern the photoresist in preparation for thin film (200 nm) Au electrode deposition (Shadpour et al., *Anal. Chem.* 79:870-878 (2007) and Kong et al., *Electrophoresis* 27:2940-2950 (2006), which are hereby incorporated by reference in their entirety), which is carried out using e-beam evaporation (step 5) and lift-off (step 6). In step 7, lithography is employed to define a Su-8 photoresist the microchannel. The fluidic ports of the top cover are opened (step 8) and the top and bottom patterned covers are aligned for UV glue injection and cure (step 9).

Other microfluidic impedance units that are known in the art can alternatively be included on the uMPS device of the present invention as described herein. Suitable impedance modules include, without limitation, microfluidic coulter systems (see e.g., Zhang et al., *Microfluid. Nanofluid.* 7:739-749 (2009), which is hereby incorporated by reference in its entirety), microfluidic FACs systems (see e.g., Fu et al., *Nat. Biotech.* 17:1109-1111 (1999), which is hereby incorporated by reference in its entirety), and microfluidic impedance systems (see e.g., (Dharmasiri et al., *Anal. Chem.* 83:2301-2309 (2011); Adams et al., *J. Am. Chem. Soc.* 130:8633-8641 (2008); Aufforth et al., *Annals of Surg. Oncol.* 20:S129-S129 (2013); Spegel et al., *Electroanalysis* 20:680-702 (2008); and U.S. Pat. No. 8,390,304 to Patterson, which are hereby incorporated by reference in their entirety). Other impedance modules suitable for use in the device of the present invention are reviewed in Cheung et al., *Cytometry Part A* 77A:648-666 (2010), which is hereby incorporated by reference in its entirety.

In one embodiment, the alternative impedance module comprises an arrangement of a Coulter counter module that provides label-less cell enumeration and sizing. This module is composed of two fluid-filled chambers connected by a small orifice and two electrodes positioned at either side of the orifice. As a cell passes through the orifice, it displaces the conductive fluid and alters the resistance of the orifice. Each signal pulse corresponds to the movement of a single cell through the orifice, the magnitude of which is proportional to the amount of fluid displaced. The highest sensitivity of the measurement is achieved when the orifice size is similar to the measured cell size. For example an orifice size of 50×50 $\mu m^2$ would achieve sufficient sensitivity to detect cells in the size range of 6-30 $\mu m$. Measurement electrodes poised on both sides of the orifice have large dimensions (few $mm^2$) to reduce the effects of electrical double layer capacitance and can be produced by screen printing of conductive silver inks on the polymer surface negating the need for lithography (see Sun and Morgan, *Microfluid. Nanofluid.* 8: 423-443 (2010), which is hereby incorporated by reference in its entirety).

In one embodiment, the device of the present invention further comprises a separator unit defined by the solid substrate and upstream of the biomolecular processor and one or more nanotubes. The separator unit comprises a separation chamber including solid surfaces defining channels between them with cell specific capture agents attached to the solid surfaces, an inlet to the chamber, and an outlet from the chamber.

The separator unit is depicted as module 400 in the uMPS device of FIGS. 17A and 17B. As shown in these figures, separator unit 400 receives sample from sensor module 350. Once the enumerated cells exit the sensor module, they are introduced to lysis buffer coming from reservoir 110, and cell lysis occurs within the small serpentine microfluidic network 136 upstream of separator unit 400. The contents of the lysed cells enter separator unit 400 where isolation of the nucleic acid components occurs. Separator unit 400 is fed immobilization buffer, air, ethanol, and release reagents via respective reservoirs 112, 114, 116, and 108 located on the periphery of the motherboard of uMPS 100 as depicted in FIGS. 17A and 17B.

Figure 25:
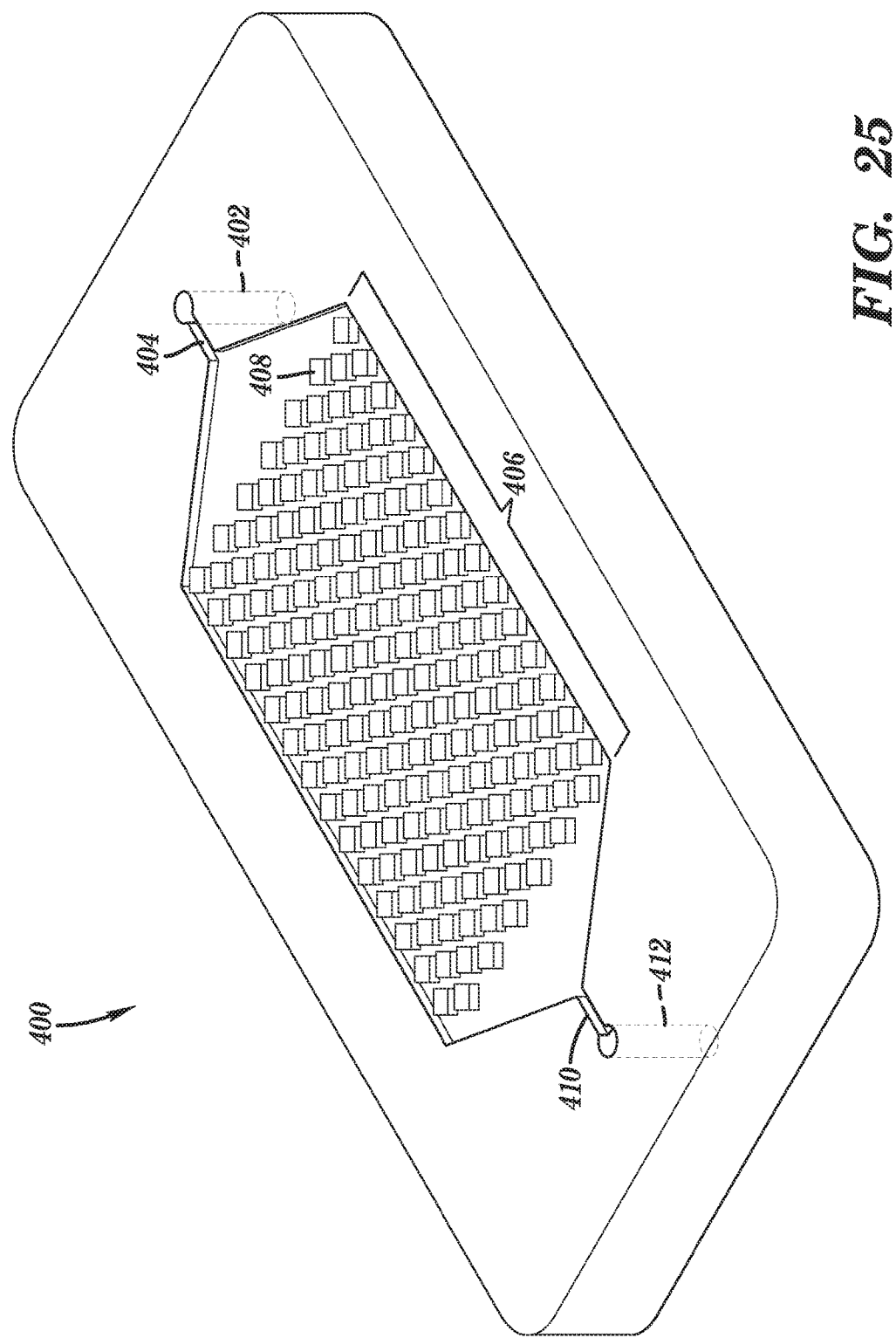
FIG. 25 is a perspective view of a SPE RNA/DNA isolation module of the uMPS.

A perspective view of the separator module is depicted in FIG. 25. As shown in this depiction, separator unit 400 is similar in structure and function to extractor units 250 and 300 described supra, differing in that it comprises single solid-phase extraction bed 406, containing a plurality of solid supports or surfaces 408. A single extraction bed is suitable, because the sample volume that requires processing is small (~10 µL) and the amount of target material to be extracted, e.g., DNA/RNA from a small number of cells isolated upstream, is low as well. The sample enters separator module 400 via input port 402 and flows through bed feeder channel 404 to enter extraction bed 406. Sample components that are not captured on solid supports 408 of extraction bed 406, move through the channels defined by solid supports 408 to extraction bed output channel 410, and exit the module via output port 412. Once the extracted sample material (e.g., the DNA/RNA) is released from solid supports 408 of extraction bed 406, it also flows out of the separation unit via output channel 410 and output port 412.

In one embodiment, the device of the present invention has one or more reactor units defined by the solid substrate and upstream of the biomolecular processor. The reactor units comprise a reaction channel with a heater. The one or more reactor units 450 and 500, which constitute the second subsystem of the uMPS device of FIGS. 17A and 17B, are continuous flow reactors used for molecular pre-processing reactions such as multiplexed reverse transcription of RNA to generate cDNA, and appending poly-dT to DNAs using terminal deoxynucleotidyl transferase (TdT). Alternative molecular pre-processing reactions that can be carried out in these units include, without limitation, enzymatic digestion reactions, e.g., digestion of input DNA with restriction endonuclease(s) for subsequent determination of methylation status, an initial reverse-transcription step, primer extension reaction, and/or appending a loop primer to miRNA, facilitating its accurate tailing, capture, and detection.

The continuous flow reactor units of the device used for the aforementioned biochemical thermal reactions are depicted as modules 450 and 500 of the uMPS device shown in FIGS. 17A and 17B. These reactors are based on a continuous flow format, in which a single meandering channel is fed the reaction reagents from adjacent reservoir 124 (e.g., RT reaction reagents), and the target material. Thermal heaters placed on the underside of the reaction zone generate the necessary temperature. This continuous flow thermal reactor consists of a serpentine channel with the linear velocity and length of the reactor channel determining the reaction time. These continuous flow thermal reactors have been used for a variety of reactions, including PCR, ligase detection reactions, and reverse transcription using thermoplastic substrates (see e.g., Hashimoto et al, *Lab on a Chip* 4:638-645 (2004); Hashimoto et al., *Analytical Chemistry* 77:3243-3255 (2005), Chen et al., *Assessment and Improvement of the Thermal Performance of a Polycarbonate Micro Continuous Flow Polymerase Chain Reactor (CFPCR)* (2007), Chen et al., *Biomedical Microdevices* 10:141-152 (2008), which are hereby incorporated by reference in their entirety). The reactor is built during the imprinting step used to produce the fluidic base plate. A thin film Kapton heater is placed underneath the reactor to generate the necessary temperature for the reaction.

In one embodiment, the device of the present invention has a flow purification unit that is upstream of the biomolecular processor and the one or more nanotubes. The flow purification unit comprises a housing defining a chamber, one or more inlets connected to the chamber, a product outlet connected to the chamber, a waste outlet connected to the chamber, and a plurality of obstacles positioned within the chamber and oriented to preferentially direct product, in the chamber, to the product outlet and to direct waste, in the chamber, to the waste outlet. Flow purification unit 550 and nanosensor unit 50 constitute the third subsystem of the uMPS device depicted in FIGS. 17A and 17B.

The flow purification unit is designed to purify the target nucleic acid molecules (e.g., cDNA) that are generated in other upstream units of the device from excess dNTPs and/or other non-target nucleic acid nucleotide components. Purification is required due to the limited number of binding sites available on the solid support structures of the bioreactor chambers of the biomolecular processor unit. While there are a variety of methods to accomplish the required removal of excess reagent(s) such as chromatographic or electrophoretic techniques, they use a "batch" operational mode in which samples are injected onto the column and the separation invoked with heart cutting used to isolate the desired material. The flow purification unit of the device described herein uses a continuous separation mode that does not require injection and heart cutting to simplify operation. It is particularly appealing to use a continuous flow format, because injection/run cycles are not required with the reaction products continuously inserted into the separation matrix with the ability to redirect the excess reagent(s) into a waste reservoir while at the same time, direct processed targets into another path.

Figure 26:
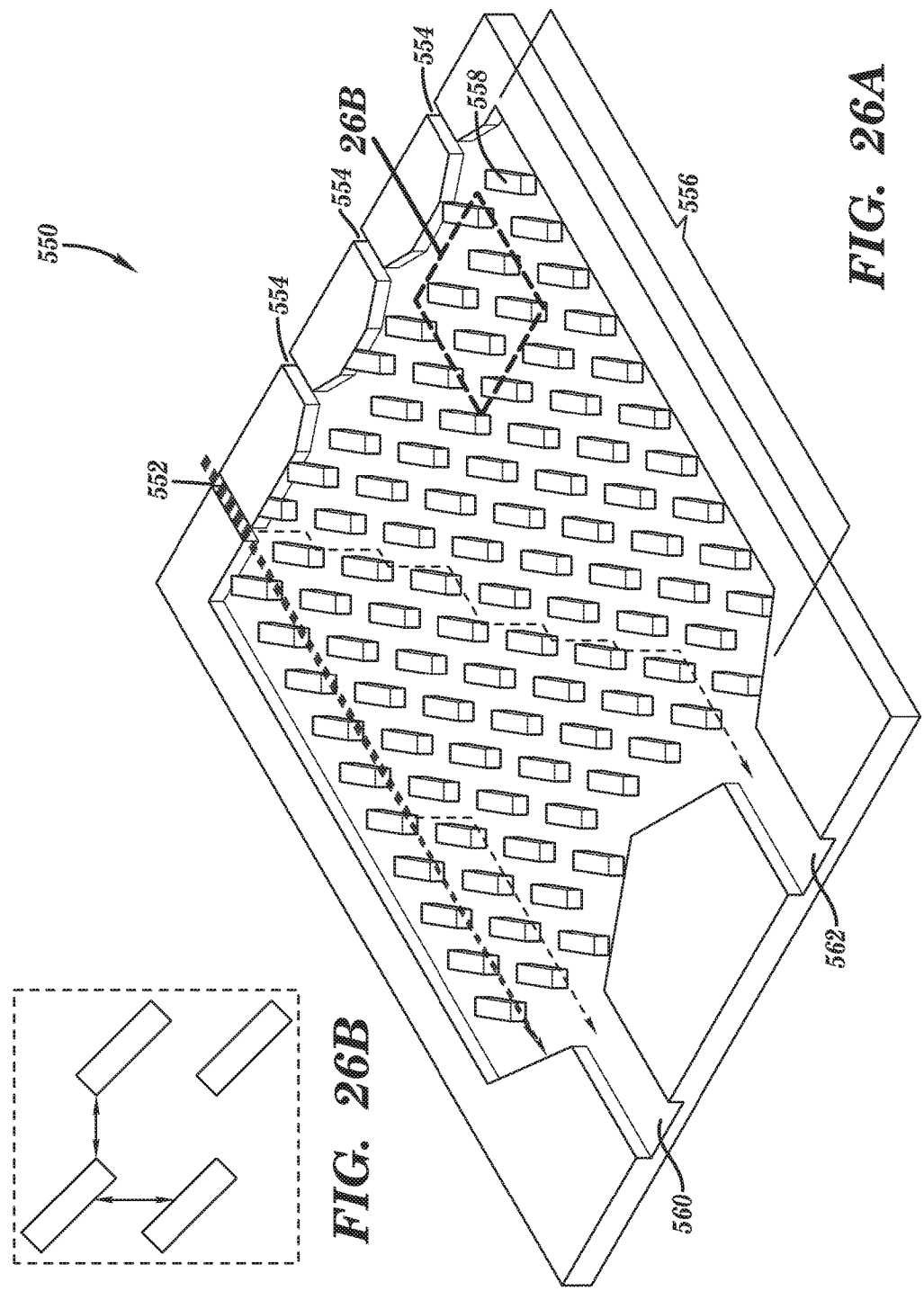
FIGS. 26A-26B show the diffusional purification module of the uMPS.

The architecture of diffusional flow purification unit 550 is shown in FIG. 26A. The module is fabricated in the appropriate substrate using micro-replication in the same step used to produce the fluidic network and thus, not requiring multi-step lithographic techniques. The basic concept is to employ the use of a regular lattice of asymmetric obstacles 558 to alter the lateral Brownian motion of the molecules so that molecules of different sizes follow different trajectories through the device. In one embodiment, obstacles 558 within flow purification bed 556 possess a length of ~5-7 µm, a width of ~0.5-2 µm, a gap spacing (G) ~4-5 µm, and are situated at ~45° angle with respect to the flow path (Chou et al., *Proc. Nat'l. Acad. Sci. U.S.A.* 96:13762-13765 (1999), which is hereby incorporated by reference in its entirety). A mixture of molecules in a sample enters module 550 via sample input channel 552, buffer enters the module via buffer input channels 554, and the mixture is sorted continuously as it moves through the device. The output is divided into two channels 560, 562, one 562 for directing reagents (e.g., dNTPs) to waste and the other 560 for sending target molecules (e.g., cDNA) to the final module on the uMPS, i.e., the nanosensor module, for final processing and detection. The performance metrics of this module includes generating short development times (<60 s), removing >95% of excess reagent(s) and minimal loss of target (<1%).

Figure 27:
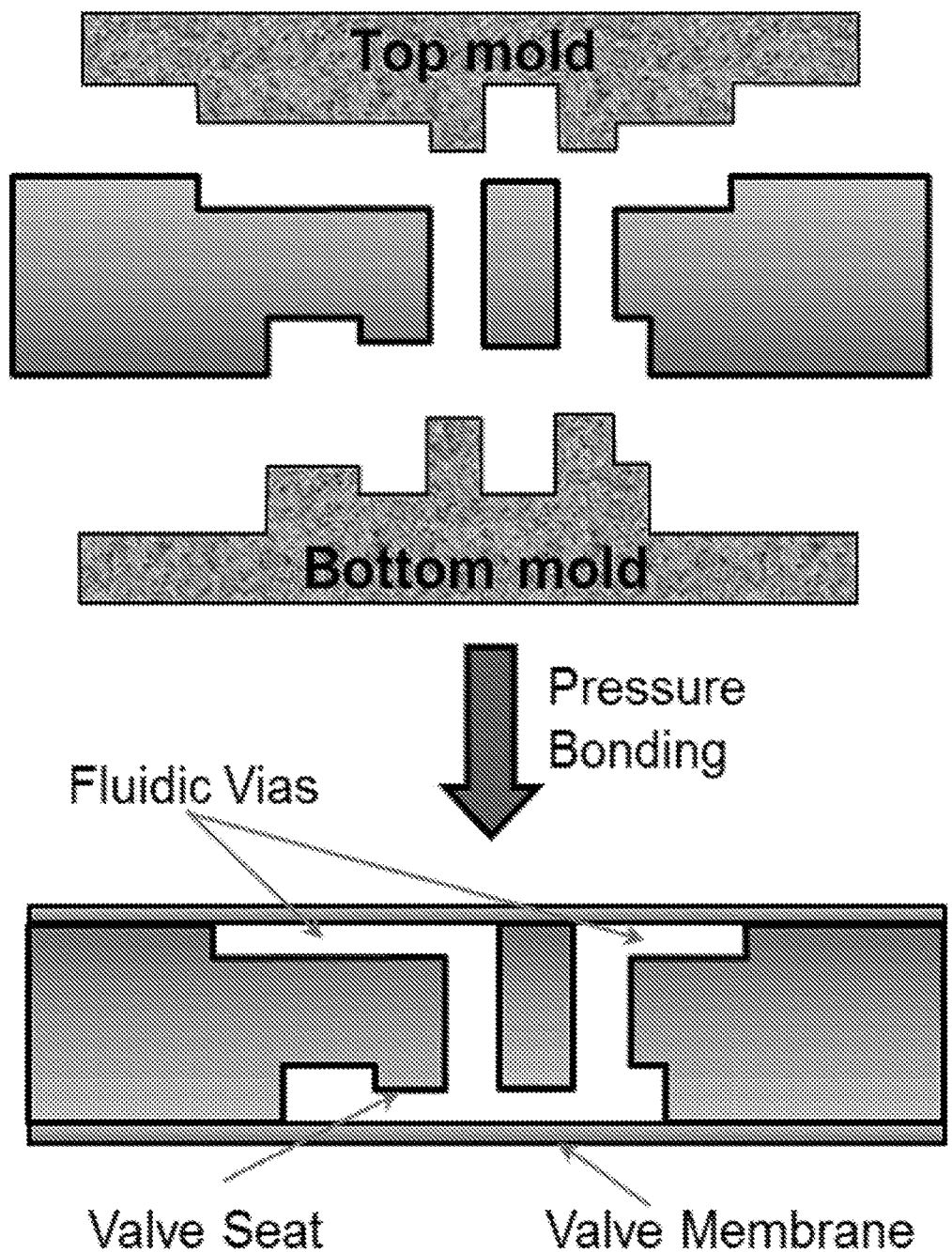
FIG. 27 illustrates the valves on a device of the present invention. The simultaneous front and backside molding of a valve and valve seat using embossing is shown.

Fluidic flow through the various units of the uMPS device of FIGS. 17A and 17B is controlled by plurality of valves 132 located throughout fluidic network 134 of device 100. The valves have a three-layer structure as depicted in FIG. 27. These three layers consist of cover plate, fluidic layer, and back cover plate. Valve seat and valve membrane are configured to be on the back side of the fluidic motherboard for the uMPS 100 along with mechanical solenoids to actuate the valves. This will allow for complete electrical connections poised on the top cover plate of the uMPS. FIG. 27 also shows simultaneous front and backside molding of the valve and valve seat using embossing. The fluidic network located on the top of the motherboard is made in the same embossing step.

Most microfluidic interconnects of the uMPS device of FIG. 17A rely on direct physical contact between the fluid port and the unit being connected. Each contact acts as a passive kinematic constraint on the assembly. If care is not taken, two or more interconnects in conjunction with other assembly features will lead to over-constrained systems and unpredictable dead volumes.

Figure 28A:
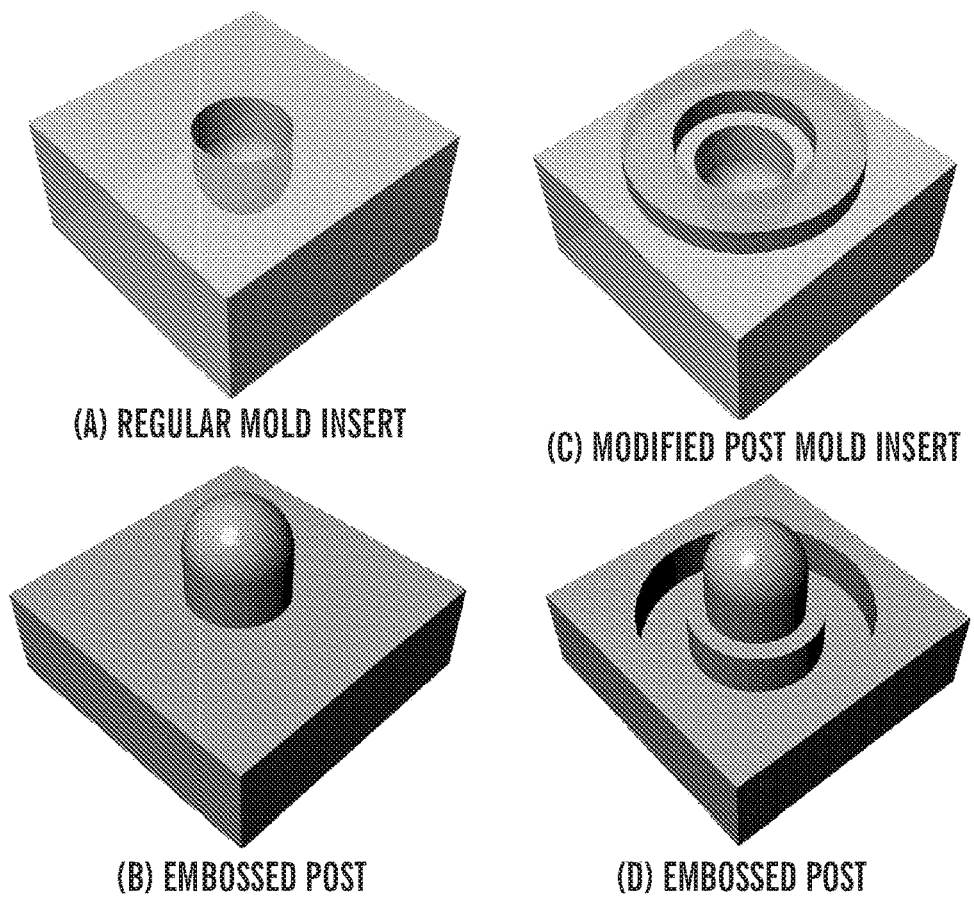
FIGS. 28A-28C show the kinematic alignment pins and grooves of the gasket-less seal. The alignment pins and grooves (FIG. 28A) can be fabricated into the fluidic substrate backside using double sided embossing with the pins and grooves poised on the two mating pieces.
Figure 28B:
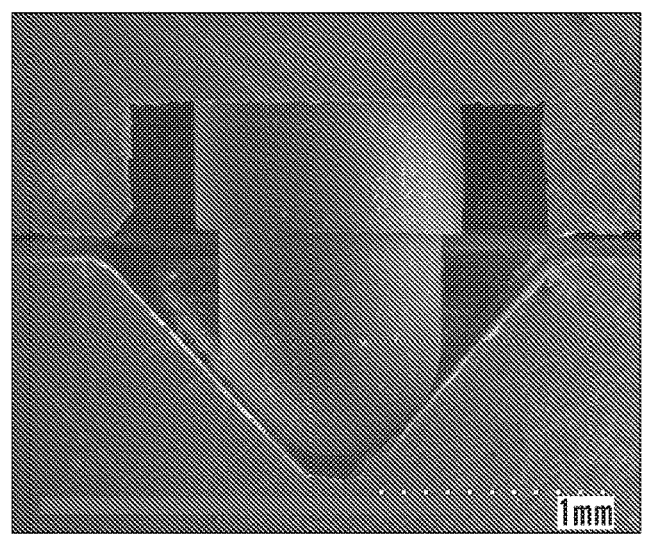
Figure 28C:
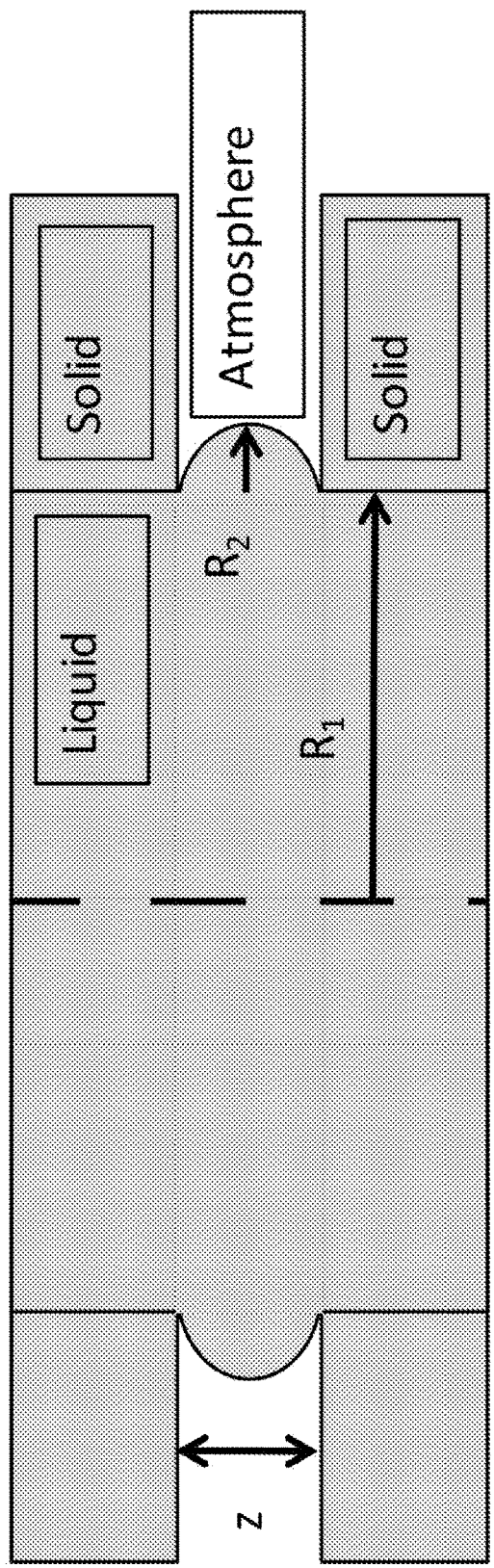

For microfluidic ports with micro-scale gaps between facing surfaces, capillary forces, as defined by the Young-Laplace equation, should resist leakage without any direct physical contact between the facing surfaces, forming a gasket-less seal as depicted FIG. 28B (Brown, et al., *IMECE* 2012, Nov. 9-15, 2012. ASME, Houston, Tex., pp. IMECE2012-89634 (2012), which is hereby incorporated by reference in its entirety). The kinematic pins and grooves of these gasket-less seals are depicted in FIG. 28A. The alignment pins and grooves can be fabricated into the fluidic substrate backside using double sided embossing with the pins and grooves poised on the two mating pieces. The alignment accuracy is ~10 µm. Superhydrophobic seals between mating pieces that can be perfectly aligned or slightly offset. The through holes on each mating piece is surrounded by a surface with a water contact angle ~150°; surface tension forces and capillary forces cause the solution to move into the opposite hole with no dead volume (see FIG. 28C).

The gasket-less seals require super-hydrophobic surfaces on the opposing surfaces around each inlet/outlet port. Different approaches can be used for obtaining the super hydrophobic surfaces including: (1) injection molding, (2) NIL, or (3) layer-by-layer deposition. Another approach involves mounting anodized aluminum oxide membranes (AAO) inside a conventional mold insert and filling the patterns with a polymer melt. These techniques supply the necessary super-hydrophobicity. The advantage of this approach is that super-hydrophobic surfaces could be molded in the same material as the device and at the same time, so there are no surface adhesion or adsorption concerns.

NIL with polymer stamps can be used to transfer a super-hydrophobic pattern into the inlet/outlet surfaces. This can be performed on injection molded or hot embossed substrates as a secondary process. Another approach is layer-by-layer (LBL) deposition, which can be used to build nanoscale thin films with high static contact angles (188). This can be performed using a mask to ensure that only the desired areas are covered. The LBL process can produce layers with much better control of the thickness. Successive dipping steps require additional time to obtain the desired layer properties, but may be comparable in duration to those necessary for moving to another machine as in the case of NIL.

Passive alignment structure: Passive alignment structures will be used to establish the height of the gap separating two modules (<20 µm) minimizing lateral offset so that dead volumes are not introduced in the inlets/outlets of modules and the relative angle between the two surfaces is minimized (see FIGS. 28A-28B). This requires selecting the type, size, and location of the alignment structures to use. These alignment structures are hemispherical pin in v-groove kinematic pairs that have been characterized (You et al., *J. Micromech. Microeng.* 19:125025 (2009) and You et al., *JMEMS* 24:634-650 (2015), which are hereby incorporated by reference in their entirety). Annular rings around the posts resulted in better pins, permitting better filling and less variation between the pins (Chen et al., *Replication of Reliable Assembly Features for Polymer Modular Microfluidic Systems* (2008), which is hereby incorporated by reference in its entirety.

Another aspect of the present invention is directed to a device comprising a longitudinally-extending plasma isolation unit as described supra and depicted in FIGS. 20A-20D. The longitudinally-extending plasma isolation unit is defined by the solid substrate and comprises an entrance passage, a discharge passage which is wider and shallower than the entrance passage, and a transition passage connecting the entrance passage and the discharge passage. The transition passage becomes wider and shallower as the transition passages progresses from the entrance passage to the discharge passage. The plasma isolation unit further comprises primary side channels extending laterally away from the entrance passage, where a separator, positioned between the entrance passage and each primary side channel, is sized to permit plasma, but not cells, to pass from the entrance passage to the primary side channels. The plasma isolation unit further comprises secondary side channels extending laterally away from the discharge passage, where a separator, positioned between the discharge passage and each secondary side channel, is sized to permit plasma, but not cells, to pass from the entrance passage to the secondary side channels.

Another aspect of the present invention is directed to a device comprising an extractor unit as described supra and depicted in FIG. 25. The extractor unit is defined by a solid substrate and comprises an inlet, an outlet, a plurality of separate chambers each extending between and sharing the inlet and said outlet. The device also comprises a plurality of solid pillars in each of the chambers, wherein the pillars have passages between them, and are provided with a material suitable to immobilize cells, nucleic acids, or exosomes from a sample.

Another aspect of the present invention is directed to a device comprising a sensor unit as described supra and depicted in FIGS. 23A-23B. The sensor unit is defined by the solid substrate and comprises: an inlet; an outlet; and a cell counter positioned to count cells passing from the inlet to the outlet of said sensor unit.

Surface Modification of Thermoplastic Surfaces on the uMPS

Surface properties are important for controlling the transport of molecules through the various microchannels, nanochannels, and other nano-structures of the modules on the uMPS, especially when the molecules bear charges and the transport is enabled by electrokinetics. The surfaces of the polymer nanostructures and microstructures are modified using a combination of an activation process to produce functional scaffolds followed by the surface modification to create new chemical species on the surface of the polymer substrates (Jackson et al., *Lab Chip.* 14:106-117 (2014) and McCarley et al., *J. Am. Chem. Soc.* 127:842-843 (2005), which are hereby incorporated by reference in their entirety). In addition, where functional groups are required on the polymer surfaces in the micro- and nano-domains for the covalent attachment of various biological agents (e.g., antibodies or oligonucleotides), techniques for producing functional groups regio-specifically are utilized. Regio-specific activation, which is required, for example, to activate only pillared regions for the covalent attachment of various molecular targets within the nanosensor module, can be accomplished using UV/$O_3$ activation through a photomask.

Many thermoplastics do not contain surface functional groups and therefore, activation protocols can be employed to create the appropriate functional scaffolds. Suitable robust, yet simple surface modification chemistries for thermoplastics within the micro-scale regime, where the surface is activated with UV/$O_3$ or an $O_2$ plasma are know in the art (Jackson et al., *Lab Chip.* 14:106-117 (2014) and Situma et al., *Anal. Biochem.* 340:123-135 (2005), which are hereby incorporated by reference in their entirety). Exposure to plasma or UV/O$_3$ renders the surface hydrophilic due to the interactions of high energy radicals on the surface. At sufficiently high energy, both UV and oxidative stress can generate radicals within the polymer, which can form carboxylic acids or other O-containing species. The presence of these functional groups provides ionizable groups that, when in contact with solutions, can either alter the electroosmotic flow or serve as scaffolds for attachment of biologics.

Fabrication of the Nanotube

Figures 29A, 29B:
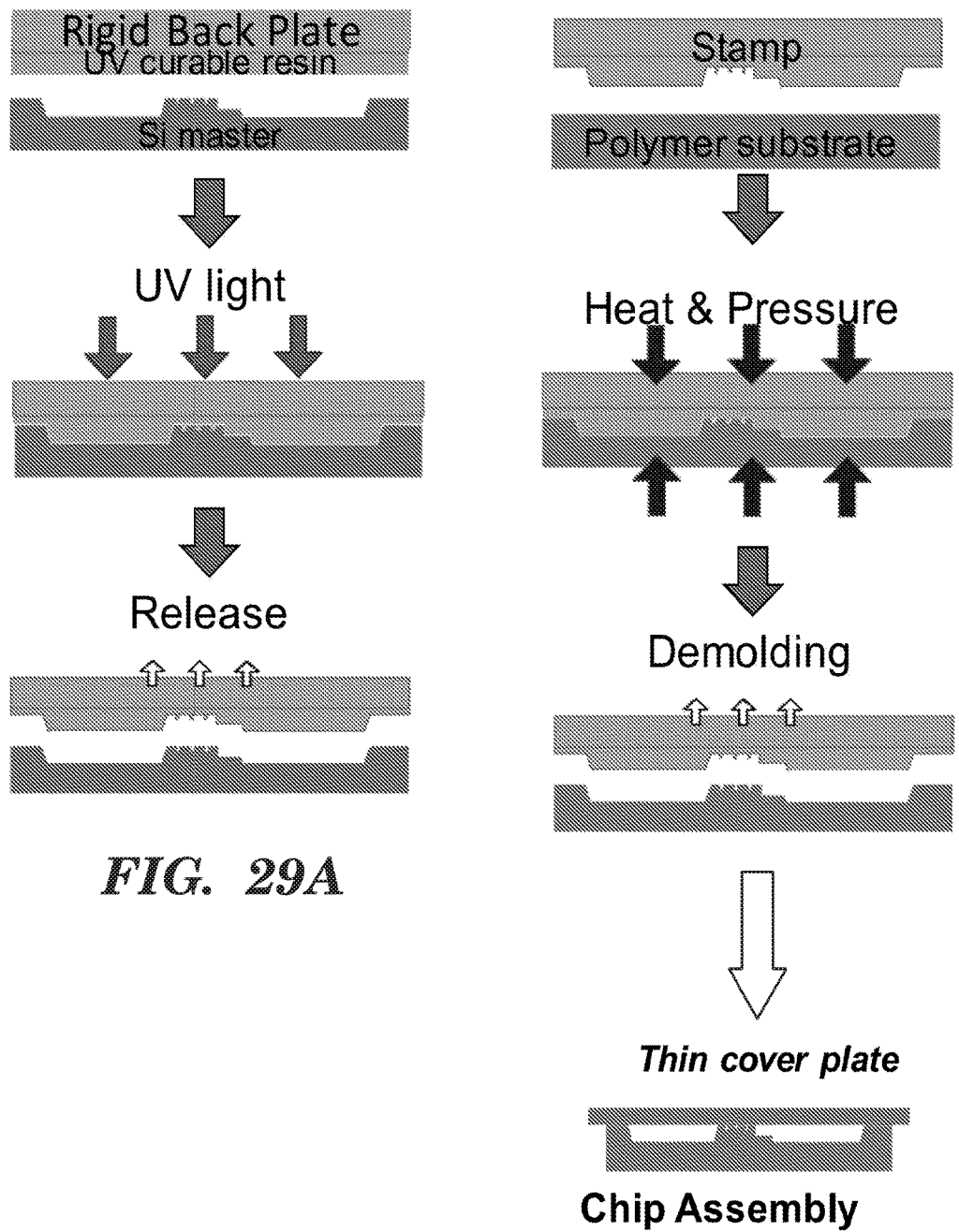
FIGS. 29A-29B illustrate the processing steps for making the nanofluidic chambers and channels of the device described herein using imprinting.
Figure 30A:
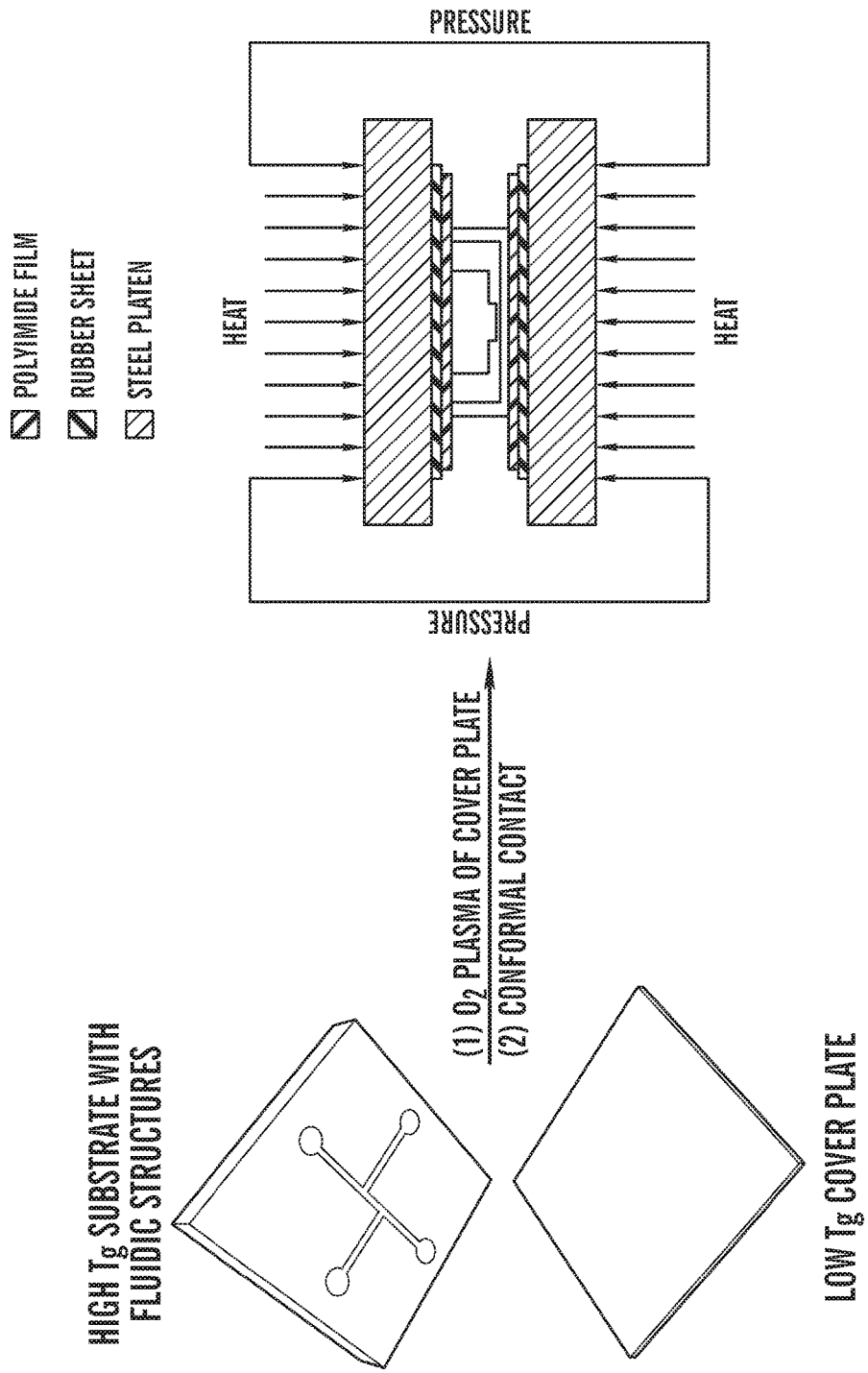
FIGS. 30A-30B show processes involved in assembling the device of the present invention.
Figure 30B:
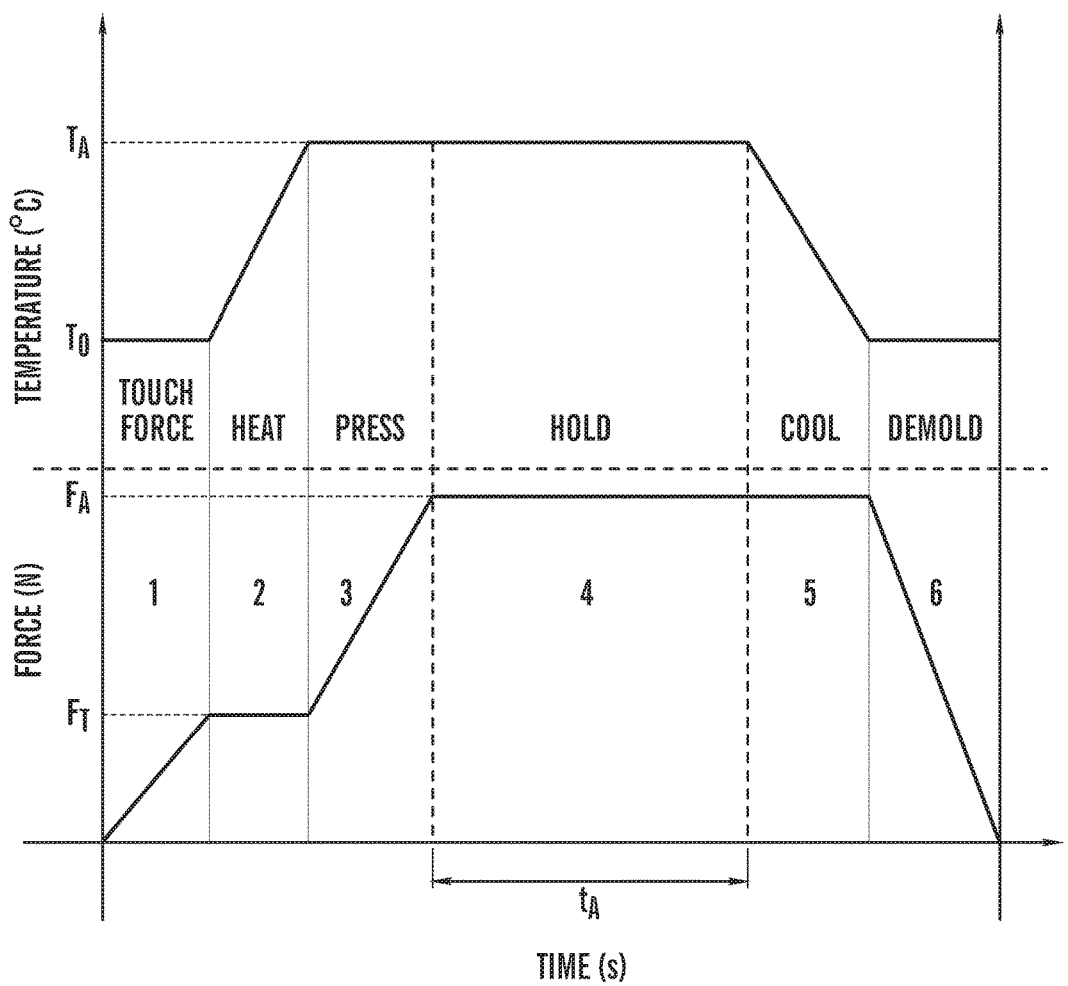

Three different strategies can be used to make the nanotubes comprising the in-plane synthetic nanopores and time-of-flight channels as described herein. A first approach involves a single step Nanoimprint lithography (NIL). A schematic of this procedure is depicted in FIGS. 29A-29B and FIG. 30. In short, because stamp structures <10 nm are required, one can use for master fabrication the Si substrate coated with a chromium layer (~300 Å) for focused ion beam (FIB) milling with varying exposure doses controlling both the width and depth for the nanochannels and in-plane synthetic nanopores (Menard & Ramsey, *Nano Letters* 11:512-517 (2010), which is hereby incorporated by reference in its entirety). As shown in FIG. 29A, the resin stamp can be fabricated via a UV-NIL process. The resin stamp is used to imprint the sensor structures into various polymer substrates as depicted in FIG. 29B. The S/N ratio of the current transients generated by the in-plane synthetic nanopores will depend on the size ratio of the nanochannel to the pores.

The second fabrication approach involves a combination of NIL and a size reduction process. It can be challenging to produce long nanochannels via single step NIL with the required in-plane synthetic nanopores, because the fabrication is affected by various factors such as a non-uniform deposition of the intermediate chromium layer, a non-uniform beam current for large area scanning in FIB and surface defects. Accordingly, in some embodiments it may be desirable to combine NIL with a size reduction process. Enlarged sensor structures can be produced in the polymer substrate with the scale ratio of 2-5, meaning that the width and depth of the nanochannels will be in the range of 100-200 nm and the size of the orifices in the range of 20-50 nm. Precise control over the polymer deformation at the nanometer scale is the key to the size reduction process to achieve sub-10 nm structures, which is difficult to achieve at a molding temperature during NIL.

Two suitable size reduction processes include (i) pressed self-perfection (PSP) process and (ii) polymer reflow process. In the PSP process, polymer nanostructures are pressed by a blank silica wafer at a temperature close to the glass transition temperature (Wang et al., *Nano Letters* 8:1986-1990 (2008), which is hereby incorporated by reference in its entirety). This process not only decreases the width and diameter of nanoscale trenches and holes, respectively, but also reduces sidewall roughness of those structures. PSP can be used in combination with NIL to generate nanopores in a freestanding polymer membrane (Choi et al., *J. Nanosci. Nanotechnol.* 13:4129-4133 (2013), which is hereby incorporated by reference in its entirety). Starting with micropores having 3 μm diameter, the pore size can be effectively reduced to ~300 nm. The second size reduction process, i.e., polymer reflow process, can generate free-standing SU-8 membranes with sub-10 nm pores. The shrinkage rate for uncured SU-8 by the polymer reflow process at 45° C. is ~3 nm/min (see FIG. 38C), which is comparable to the shrinkage rates of 6-16 nm/min and 1.2-15 nm/min used for fabricating silicon and glass-based nanopores via irradiation with a high-energy electron beam (Steinbock et al., *Nano Letters* 13:1717-1723 (2013), which is hereby incorporated by reference in its entirety). A low shrink rate makes the polymer reflow process extremely attractive to achieve nanoscale controllability for polymer nano-manufacturing.

The third fabrication approach involves integration of nanopore membranes with track-etched membranes. In this approach, the nanotubes are fabricated by vertically stacking prefabricated nanopore membranes with a track-etched membrane. In this process, free-standing nanopore membranes are produced with a well-defined pore diameter in the range of 10 nm by a single NIL step into a double resist layer. The pore size in the membrane can be further reduced by employing a post-NIL polymer reflow process to achieve sub-10 nm pores. For the nanochannels, track-etched polycarbonate membranes are used to generate low density nanopores. The pore diameter and membrane thickness is in the range of 100-200 nm and 60-100 μm, respectively. The alignment of a nanopore in the free-standing SU-8 membrane and a nanopore in the track-etched membrane is done using optical microscopy. This is feasible, because the nanopore in the SU-8 membrane has a tapered structure along the membrane thickness and the micro-scale bottom pore of the track-etched membrane has a well-defined octagon shape. The stacked membranes (SU-8 membrane/track-etched membrane/SU-8 membrane) will contain the designed structures of nanochannel with two nanopores and the tapered inlet and exit for the nanopores in the SU-8 to reduce the error caused by the entropic barrier in the determination of the flight time. Finally, the stacked membrane is sandwiched between two thermoplastic (PMMA or others) chips with a microchannel in a cross configuration to complete an enclosed fluidic device for longitudinal transient current measurements. A single pore in the stacked membrane can be registered between upper and lower microchannels by controlling the width of the microchannels. FIG. 2A-2B show an example of a vertically positioned nanopore fabricated using this approach.

Methods for Detecting a Target Nucleic Acid Molecule

Another aspect of the present invention relates to a method for detecting the presence of a target nucleic acid molecule in a sample that involves providing the device comprising the biomolecular processor and one or more nanotubes as described herein, and feeding a sample comprising a target nucleic acid molecule or complementary extension product thereof into the biomolecular processor under conditions effective for the target nucleic acid molecule to bind to the capture molecules on the spaced support structures so as to immobilize the target molecule to the spaced support structures. The method further involves subjecting the immobilized target nucleic acid molecule or immobilized complements of the target nucleic acid molecules to a reaction process to form an oligonucleotide reaction product that is released, fed into the nanotube, and detected as it passes through the one or more nanopores in the nanotube. As described in more detail below, the detector detects an identifying signature of the oligonucleotide reaction product, which is unique to the oligonucleotide product and distinguishes it from other oligonucleotide products that may be formed in the reaction process.

In one embodiment, the reaction process in a ligase detection reaction that produces ligation products hybridized to the immobilized target nucleic acid molecules or immobilized extension products thereof. The ligation products are denatured from the immobilized target nucleic acid molecules and immobilized extension products thereof, to release the ligation products from the spaced support structures. The ligation products pass through the one or more nanotubes, and the detector detects the identifying signatures of ligation products passing through the one or more nanotubes. The presence of target nucleic acid molecules in the sample differing from other nucleic acid molecules in the sample is identified based on detection of the identifying signature of the ligation product.

In accordance with this aspect of the present invention, the device comprising the biomolecular processor and one or more nanotubes may contain one or more units upstream of the biomolecular processor that are configured to prepare the sample for analysis in the biomolecular processor and one or more nanotubes. These units are described supra and include, a cell separator unit (e.g., module 150, FIGS. 17A and 17B) for separating or enriching for target biological cells (e.g., circulating tumor cells), a longitudinally-extending plasma isolation unit (e.g., module 200, FIGS. 17A and 17B) to separate plasma from red blood cells and white blood cells, a first extractor unit (e.g., module 250, FIGS. 17A and 17B) for affinity purifying exosomes, a second extractor unit (e.g., module 300, FIGS. 17A and 17B) for purification of cfDNA, a sensor unit (e.g., module 350, FIGS. 17A and 17B) for counting cells and determining viability, a second extractor unit (e.g., module 400, FIGS. 17A and 17B) for DNA and/or RNA isolation, one or more reactor modules for reverse transcriptase reactions and TdT reactions (e.g., modules 450 and 500, FIGS. 17A and 17B), and a flow purification module (e.g., module 550, FIG. 17A) to remove excess dNTPs and other non-target nucleic acid molecule components from the sample prior to entering the nanosensor chamber and biological processor.

Methods of carrying out the ligation reaction and generating the ligation products within the bioreactor chamber of the biomolecular processor are described infra. The ligation products, once formed, are denatured from their complementary immobilized target nucleic acid molecule or extension product thereof and fed through a nanotube containing one or more nanopores capable of detecting and distinguishing an identifying signature of each ligation product as it passes through it. In one embodiment, the identifying signature of a ligation product is the change in current through one or more nanopores that occurs when the ligation product passes through it. The change in current can be an increase (i.e., current augmentation) or a decrease in current (i.e., a current blockage) through the nanopore or nanopores. The magnitude and duration of current change through a nanopore is detected and measured to identify and distinguish one ligation product from another. In accordance with this embodiment, the identifying signature of a ligation product is influenced by the size (i.e., length), shape or conformation (e.g., folded vs. linear), charge, and conductivity of the ligation product.

In another embodiment, the identifying signature of a ligation product is its time of flight through one or more sections of the nanotube. In this embodiment, the ligation product is fed through at least a first and second nanopore of a nanotube, where the first and second nanopores are positioned on opposing ends of the nanotube time-of-flight channel. The time it takes for the ligation product to pass through the first nanopore, the time-of-flight channel, and the second nanopore are measured and used as the identifying signature of the ligation product. In accordance with this embodiment, the identifying signature of a ligation product is influenced by the size (i.e., length), shape or conformation (e.g., folded vs. linear), charge, and conductivity of the ligation product.

In another embodiment, the identifying signature of a ligation product is the change in current through at least two nanopores that occurs when the ligation product passes through the two nanopores in combination with the time-of-flight measurement between the two nanopores. In accordance with this embodiment, the identifying signature of a ligation product is also influenced by the size (i.e., length), shape or conformation (e.g., folded vs. linear), charge, and conductivity of the ligation product.

The identifying signature of a ligation product is an inherent property of the ligation product itself that can be further modified by the incorporation or appendage of one or more identifying signature modifiers. In one embodiment, identifying signature modifiers are water soluble, neutral or charged molecules that modify the mobility of the ligation product, e.g., drag-tags. Exemplary mobility modifiers include, without limitation, polypeptides, polynucleotides, peptide nucleotide analogue (PNA) multimers, peptoids, polyethers (polyethylene oxide and polypropylene oxide), nanospheres, nanocrystals, oligosaccharides, dendrimers, polyesters (polyglycolic acid, polylactic acid), polyurethanes, polyamides, polysulfonamides, polysulfoxides, polyphosphates, polyphosphonates, and combinations thereof. This approach is based on free solution conjugate electrophoresis (FSCE), also known as end-labeled free-solution electrophoresis (ELFSE) (Ren et al., "Separating DNA Sequencing Fragment without a Sieving Matrix," *Electrophoresis* 20(12):2501-9 (1999), which is hereby incorporated by reference in its entirety). In this embodiment, single-base differences of ligation products are distinguished by use of different length tails and/or drag-tags on one of the ligation probes used in the ligation reaction to create the ligation product (Albrecht et al., "Simultaneous Detection of 19 K-ras Mutations by Free Solution Conjugate Electrophoresis of Ligase Detection Reaction Products on Glass Microchips," *Electrophoresis* 34(4):590-7 (2013); Sinville et al., "Ligase Detection Reaction for the Analysis of Point Mutations using Free-solution Conjugate Electrophoresis in a Polymer Microfluidic Device," *Electrophoresis* 29(23):4751-60 (2008), which are hereby incorporated by reference in their entirety). The resultant ligation products differ in length and/or mass/charge ratio, and thus they migrate differently from each other and the initial probes, and may be distinguished by their influence on current through a nanopore. Free-solution electrophoretic separation of DNA-drag-tags has been demonstrated for DNA up to 265 bases in length (Albrecht et al., *Anal Chem.* 83(2):509-15 (2011), which is hereby incorporated by reference in its entirety).

In another embodiment, the identifying signature modifier is a molecular sequence barcode, i.e., a nucleotide sequence that can be distinguished through a nanopore based on sequence specific current modification through one or more nanopores (Manrao et al., "Reading DNA at Single-nucleotide Resolution with a Mutant MspA Nanopore and phi29 DNA Polymerase," *Nat Biotechnol.* 30(4):349-53 (2012), which is hereby incorporated by reference in its entirety). In this example, single-base differences at the ligation junction are distinguished by use of different sequence bar-codes on the upstream oligonucleotide ligation probes, which serve as markers for the individual base that is being interrogated. The short ligation products generated can either be distinguished by their innate sequence by passage through a nanopore or by the use of sequence bar-codes which have been designed to compensate for the high error rates of existing nanopore sequencing systems.

Alternatively, the bar-codes can be composed of non-nucleotidic polymers which enhance their detection and discrimination as they pass through a nanopore (Kumar et al. "PEG-Labeled Nucleotides and Nanopore Detection for Single Molecule DNA Sequencing by Synthesis," *Sci. Reports* 2:684 (2012), which is hereby incorporated by reference in its entirety). Since the mobility of ss DNA molecules through nanopores is too high for accurate sequence determination, it is sometimes necessary to append a molecular motor directly to the nanopore or alternatively to a sequence motif covalently appended to the ligation product to allow the controlled stepwise ratcheting of the ligation product through the nanopore (Lieberman et al., "Dynamics of the translocation step measured in individual DNA polymerase complexes," *J Am Chem Soc.* 134(45): 18816-23 (2012), which is hereby incorporated by reference in its entirety).

Another aspect of the present invention is directed to a method for identifying a nucleotide within a target nucleic acid molecule from a sample. This method involves providing the device comprising the biomolecular processor and one or more nanotubes as described herein. The sample comprising target nucleic acid molecules is fed into said biomolecular processor under conditions effective for the target nucleic acid molecules to bind to their complementary capture molecules immobilized on the spaced solid support structures, thereby immobilizing the target nucleic acid molecules to the spaced support structures. The immobilized target nucleic acid molecules or immobilized extension products that are complementary to the target nucleic acid molecule are contacted with a solution to form a nucleotide extension reaction mixture. The solution comprises one or more oligonucleotide primers complementary to a portion of the immobilized target nucleic acid molecules or the immobilized extension product thereof, a polymerase, and a collection of nucleotide triphosphates. Each type of nucleotide triphosphate in the collection has (1) a different cleavable identifying signature-generating moiety and (2) a cleavable blocking moiety that blocks further nucleotide extension reactions. The method further involves subjecting the nucleotide extension mixture to a hybridization treatment, where the one or more oligonucleotide primers of the solution hybridize in a base-specific manner to their complementary immobilized target nucleic acid molecules or immobilized extension products thereof. The hybridized oligonucleotide primers are extended by single base-specific addition of a nucleotide triphosphate from the collection of nucleotide triphosphates to the 3' end of the hybridized primers. The identifying signature-generating moiety is cleaved from each nucleotide added to the hybridized oligonucleotide primer after the extending, and the cleaved identifying signature-generating moiety is passed through the one or more nanotubes. The detector detects the identifying signature generated by the cleaved identifying signature-generating moiety when the cleaved identifying signature-generating moiety passes through the one or more nanotubes, and the nucleotide from the collection of nucleotides that was added during said extending is identified based on the detection of the identifying signature-generating moiety, thereby identifying one or more nucleotides in the target nucleic acid molecule in the sample.

In accordance with this aspect of the present invention, the target nucleotide sequence of a target nucleic acid molecule can be sequenced by repeating, the extending, cleaving, passing, detecting, and identifying steps.

In accordance with this aspect of the present invention, the device comprising the biomolecular processor and one or more nanotubes housed in a nanosensor unit may contain one or more units upstream of the nanosensor unit that are configured to prepare the sample for analysis in the biomolecular processor. These units are described supra and include, a separator unit (e.g., module 150, FIG. 17A) for separating or enriching for target biological cells (e.g., circulating tumor cells), a longitudinally-extending plasma isolation unit (e.g., module 200, FIG. 17A) to separate plasma from red blood cells and white blood cells, a first extractor unit (module 250, FIG. 17A) for affinity purifying exosomes, a second extractor unit (module 300, FIG. 17A) for purification of cfDNA, a sensor unit (module 350, FIG. 17A) for counting cells and determining viability, a second extractor unit (module 400, FIG. 17A) for DNA and/or RNA isolation, one or more reactor modules for reverse transcriptase reactions and TdT reactions (modules 450 and 500, FIG. 17A), and a flow purification module (module 550, FIG. 17A) to remove excess dNTPs and other non-target nucleic acid molecule components from the sample prior to entering the nanosensor chamber and biological processor.

The blocking moiety of the nucleotide triphosphate may directly block the addition of a subsequent nucleotide triphosphate at its 3'OH group. In this embodiment, the blocking moiety is appended to the nucleoside triphosphate at the 2'-O of a ribose, or the 3'-O of a deoxyribose. These nucleotide triphosphates are analogous to fluorescent sequencing-by-synthesis (Ju et al., "Four-color DNA sequencing by synthesis using cleavable fluorescent nucleotide reversible terminators," *Proc Natl Acad Sci USA.* 103(52):19635-40 (2006), which is hereby incorporated by reference in its entirety). In the case of 3'-O blocking groups, there are several well-demonstrated examples in the literature, including, but not limited to amino, azidomethyl, and cyanoethyl groups. The specific nature of the group should be chosen for a combination of efficiency of enzymatic incorporation and ease of removal during the deblocking step. Removal of the blocking group is specific to the chemical nature of the blocking group; however, example include the use of mild aqueous reagents (i.e., reducing agents) at temperatures that preserve the primer-template duplex and do not cause loss of signal due to melting of the primer-template duplex.

Alternatively, the blocking moiety of the nucleotide triphosphate reversibly inhibits the addition of a subsequent nucleotide triphosphate at its 3'OH group. These blocking moieties can be appended to a nucleotide triphosphate at the C5 or C7 position of the nucleoside, i.e., the pyrimidine or purine, respectively. These nucleotide triphosphates are similar to Lightning Terminators™ (LaserGen, Inc.) (see Gardner et al., "Rapid Incorporation Kinetics and Improved Fidelity of a Novel Class of 3'-OH Unblocked Reversible Terminators," *Nucleic Acids Research* doi:10.1093/nar/gks330 (May 2012) and Litosh et al., "Improved Nucleotide Selectivity and Termination of 3'-OH Unblocked Reversible Terminators by Molecular Tuning of 2 nitrobenzyl Alkylated HOMedU Triphosphates," *Nucleic Acids Research* 39(6):e39 (2011), which are hereby incorporated by reference in their entirety) and Virtual Terminator™ (Helicos BioSciences) (Bowers et al., "Virtual Terminator Nucleotides for Next-Generation DNA Sequencing," *Nat. Methods* 6:593-595 (2003), U.S. Pat. No. 8,071,755 to Efcavitch et al., U.S. Pat. No. 8,114,973 to Siddiqi et al., WO 2008/0169077 to Siddiqi et al., which are hereby incorporated by reference in their entirety). Chemical moieties which interfere with incorporation of dNTPs by a template dependent DNA polymerase that utilize steric bulk or charged inhibition or combinations of both can be used. Examples of inhibitory moieties are dipeptides of Glu-Glu or Asp-Asp.

In accordance with this aspect of the present invention, a suitable identifying signature-generating moiety is one that can be coupled to a nucleotide triphosphate and is capable of measurably modifying or modulating (i.e., augmenting or blocking) current through one or more nanopores.

Suitable identifying signature-generating moieties include water soluble, charged molecules, for example and without limitation, acidic polypeptides, basic polypeptides, dinucleotides, trinucleotides, peptide nucleotide analogues, charged polymers (e.g., polyethylene glycol polymers), nanospheres, nanocrystals, charged oligosaccharides, dendrimers, fluorescent dyes, infrared dyes, chromophores, quinolones, coumarin, porphyrins, porphyrin-metal complexes, water soluble aromatic polycyclic molecules, water soluble aromatic heterocyclic molecules, transition-metal complexes, metal chelates, metal chelate polymers, 2-nitrobenzyl derivatives, or any combination of these moieties. The cleavable identifying signature-generating moiety is appended to each nucleotide triphosphate at its nucleoside C5 position or its nucleoside C7 position.

Once the identifying signature-generating moiety is cleaved, it is fed through one or more nanotubes for detection. The identifying signature-generating moiety is detected as it passes through one or more nanopores based on a measurable change in current through each nanopore that is generated as the moiety passes through each nanopore. As noted supra, the change in current can be an increase (i.e., current augmentation) or a decrease in current (i.e., a current blockage) through the nanopore or nanopores. The magnitude, duration, and direction of current change through a nanopore is detected and measured to identify and distinguish each of the nucleotide triphosphates. The identifying signature of identifying signature-generating moiety is influenced by the size, shape, charge, and conductivity of the moiety as well as the length, diameter, and molecular properties of the nanopore as described supra (e.g., composition and/or surface coating of the nanopore).

In another embodiment, the identifying signature-generating moiety is detected and distinguished based on its time of flight in time-of-flight channel within the nanotube. In this embodiment, the cleaved electronic generating moiety is fed through at least a first and second nanopore, where the first and second nanopores are positioned on opposing ends of a time-of-flight channel of the nanotube. The time it takes for a moiety to pass through the first nanopore, the time-of-flight channel, and the second nanopore are measured and used as the identifying signature of the identifying signature-generating moiety. The identifying signature of identifying signature-generating moiety is influenced by the size, shape, charge, and conductivity of the moiety as well as the length, diameter, and molecular properties of the nanopores and the time-of-flight nanochannel (e.g., composition and/or surface coating of the nanopore and nanochannel).

In another embodiment, the identifying signature-generating moiety is detected and distinguished based on both the change in current through at least two nanopores that occurs when the identifying signature-generating moiety passes through the two nanopores in combination with the time-of-flight measurement between the two nanopores.

In accordance with this and all aspects of the present invention, the samples containing nucleic acid molecules of interest for analysis using the methods described herein include, without limitation, tissue, cells, serum, blood, plasma, amniotic fluid, sputum, urine, bodily fluids, bodily secretions, bodily excretions, cell-free circulating nucleic acids, cell-free circulating tumor nucleic acids, cell-free circulating fetal nucleic acids in pregnant woman, circulating tumor cells, tumor, tumor biopsy, and exosomes.

The target nucleic acid molecules within the sample to be detected can be double stranded deoxyribonucleic acid molecules (DNA), single stranded DNA molecules, DNA molecules comprising one or more methylated nucleotide bases, DNA molecules comprising one or more modified or damaged nucleotide bases, ribonucleic acid (RNA) molecules, i.e., long non-coding RNA (lncRNA), ribosomal RNA (rRNA), small nuclear RNA (snoRNA), microRNA (miRNA), transfer RNA (tRNA), and small interfering RNA (siRNA), RNA molecules comprising one or more modified or damaged nucleotide bases, and RNA/DNA hybrid molecules.

In accordance with this and all aspects of the present invention, the immobilized capture molecule is a binding partner to a portion of the target nucleic acid molecule or a portion appended to the target nucleic acid molecule. Suitable capture molecules and their respective binding partners present on the nucleic acid molecule include, without limitation, biotin and streptavidin, maltose and maltose binding protein, chitin and chitin binding protein, amylase and MBP, glutathione transferase and glutathione-S-transferase, histag and NTA matrix, integrin and integrin binding peptides. In another embodiment, the capture molecule is a polynucleotide sequence that is complementary to a portion of the nucleic acid sequence of the target nucleic acid molecule. For example, in one embodiment, the capture molecule is a homopolymer sequence of a mononucleotide triphosphate, e.g., a poly-dA or poly-T primer, and the target nucleic acid molecules of the sample contain the complementary homopolymer sequence of mononucleotide triphosphate, i.e., a poly-T or poly-dA tail.

In one embodiment of the present invention, the binding partner of the immobilized capture molecule is appended to the target nucleic acid molecule to facilitate immobilization. The nucleic acid molecules in the sample may be randomly fragmented and treated so as to append the adaptor portions containing a suitable binding partner, and optionally, one or more further portions, e.g., a primer binding portion, to each end of the fragmented nucleic acid molecules. For example, the ends of a DNA molecule, either blunt ended or made flush using a variety of enzymes, such as T4 polymerase or *E. coli* polymerase, can be phosphorylated using T4 Kinase. A polymerase without 3' to 5' proofreading activity (such as Klenow (exo)) is used to add an extra "A" to the 3' end, creating a single base 3'A overhang suitable for adapter ligation using linkers containing single base 3'T overhangs. Appending adaptor portions to a nucleic acid molecule and complement thereof can also be achieved using anyone of a variety of enzymatic reactions known in the art. Suitable enzymes include, without limitation, ligases (e.g., *E. coli* ligase or T4 DNA ligase), polymerases (e.g., Taq polymerase, T4 polymerase, or *E. coli* polymerase), recombinases, terminal transferases, endonucleases, DNA repair enzymes, and reverse transcriptases. Exemplary approaches for appending adapter portions to various target nucleic acid molecules (e.g., DNA, mRNA, miRNA) are well known in the art.

In one embodiment, the adapter portions are added using a terminal transferase to append a homopolymer sequence of mononucleotide triphosphate, i.e., a poly-T or poly-dA tail to the 3' end of the target nucleic acid molecule. In another embodiment, the adapter portions are appended to the target nucleic acid molecule using locus specific set of oligonucleotide primers and a polymerase. In this embodiment, a first oligonucleotide primer of the primer set comprises a 5' nucleotide adapter sequence that serves as a binding partner to the capture molecule, e.g., a poly-dA, poly-T sequence tail, and a 3' target nucleotide sequence that is complementary to a portion of the target nucleic acid molecule. The second oligonucleotide primer of the primer set comprises an optional 5' primer-specific portion and a 3' nucleotide sequence that is complementary to a portion of an extension product formed from the first primer. To enhance specificity of adapter appending polymerase reaction, one or both oligonucleotide primers of the oligonucleotide primer set have a 3' cleavable nucleotide or nucleotide analogue and a blocking group that block polymerase mediated extension of one or both primers. Suitable blocking groups include for example, without limitation, a propanol group (3' SpC3), a dideoxy ribose base (3' ddC), a phosphate (3' phosphate), or a phosphorothioate group (Nikiforow, et al., "The Use of Phosphorothioate Primers and Exonuclease Hydrolysis for the Preparation of Single-stranded PCR Products and their Detection by Solid-phase Hybridization," *PCR Methods and Applications,* 3:p. 285-291 (1994), which is hereby incorporated by reference). Cleavage of the 3' blocking group of the oligonucleotide primer to liberates a 3'OH suitable for polymerase can be achieved using RNaseH when the primer is designed to contain an internal ribonucleotide base (see Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety), using Tth Endo IV or *E. coli* Endo IV when the primer is designed to contain an internal abasic site (e.g., tetrahydrofuran), or using Tth Endo V or *E. coli* Endo V when the primer is designed to contain an internal U paired to a G on the template (cleavage will liberate the 2nd or 3rd phosphodiester bond 3' to the U-G mismatch).

Target nucleic acid molecules may optionally be enriched prior to immobilization to the solid support via binding to their respective capture molecule. Target nucleic acid molecule enrichment can be carried out using methods known in the art and as described herein.

Once the target nucleic acid molecules are immobilized to the solid support via binding to their respective immobilized capture molecules, the immobilized target nucleic acid molecules or immobilized extension products that are complementary to the target nucleic acid molecules are subject to a ligation reaction process, extension reaction process, or other enzymatic reaction.

In one embodiment, the immobilized target nucleic acid molecule is used as the template for the ligation reaction process. In this embodiment, terminal transferase appends biotinylated nucleotide triphosphates to the end of the nucleic acid molecule, and the biotinylated target nucleic acid molecule is immobilized on the solid support via binding to streptavidin coated to the surface of the solid support. Although biotin-streptavidin is not a covalent binding interaction, tailing with biotin generally allows capture of 2-3 biotins from the same molecule on the streptavidin tetramer, and immobilization in this manner can withstand denaturing conditions (high formamide, and/or heating to 90° C.) of the ligation reaction process. Such a denaturation is required to release the ligation products generated by the ligation reaction process from the immobilized target on the solid surface for the subsequent distinguishing and detection step.

In another embodiment, terminal transferase appends dCTP to a target nucleic acid end, and the labeled target nucleic acid molecule is immobilized on the solid support via binding to $dG_{50}$ oligonucleotide capture molecules on the solid support. Similar to the biotin-streptavidin binding interaction, homo-polymer dC:dG binding is strong enough to withstand the denaturing conditions described above. Such a denaturation is required to release the ligation products generated by the ligation reaction process from the immobilized target on the solid surface for the subsequent distinguishing and detection step. This allows the target nucleic acid molecule to serve as the template for the ligation reaction process.

In another embodiment, immobilized extension products that are complementary to the immobilized target nucleic acid molecule are generated on the spaced support structures of the bioreactor chamber, and used as the template for the ligation reaction process. Immobilized extension products are generated using solid phase amplification reactions known to those of skill art and/or as described herein.

In one embodiment, the capture molecule is a capture oligonucleotide that also serves as a primer to facilitate linear solid phase amplification of bound target nucleic acid molecules. In accordance with this embodiment, a capture oligonucleotide, e.g., a poly-dA capture primer, hybridized to a complementary portion of the target nucleic acid molecule, e.g., an adapter portion of the target nucleic acid molecule containing poly-T tail, is extended using polymerase and pool of dNTPs to make a full-length copy of the immobilized target nucleic acid molecule. Using a polymerase having strand-displacement activity, such as Bst polymerase, allows for linear amplification of the target nucleic acid molecule. Following primer extension to form an immobilized extension product that is complementary to the target nucleic acid molecule, the temperature is increased such that the poly-T portions of target nucleic acid molecule and its extension product denature, allowing for an adjacent, non-hybridized capture oligonucleotide to bind to the target nucleic acid molecule and be extended. This linear amplification faithfully produces copies the original template strand of the nucleic acid molecule as it is "handed-off" to the next primer. This process continues until non-hybridized capture oligonucleotide primers on the solid support are exhausted.

In another embodiment, the target nucleic acid molecule with appended adapter portions is circularized, and solid phase amplification is achieved via a rolling circle amplification reaction (Lizardi et al., "Mutation Detection and Single-molecule Counting Using Isothermal Rolling-circle Amplification," *Nat Genet* 19:225-232 (1998), which is hereby incorporated by reference in its entirety). In accordance with this embodiment, the immobilized capture oligonucleotide serves as a primer to prime the solid phase rolling circle amplification. The circularized nucleic acid molecule hybridizes to the immobilized capture oligonucleotide via its complementary adapter portion (e.g., the poly-T sequence of the circularized nucleic acid molecule hybridizes to the immobilized poly-dA capture oligonucleotide). In the presence of polymerase having strand displacing activity and a pool of dNTPs, the immobilized primer is continually extended around the circularized nucleic acid molecule to generate immobilized extension products that comprise multimeric tandem linear repeating sequences that are complementary to the sequence of the circularized adapter appended target nucleic acid molecule.

To further enhance solid phase amplification and immobilization of extension products that are complementary to the target nucleic acid molecule, the adapter portion of the target nucleic acid molecule is designed to contain one or more universal primer-specific portions. In accordance with this embodiment, one or more primers having a 3' portion having the same sequence of the universal primer-specific portion of the adapter portion of the target nucleic acid molecule is provided to hybridize to its complementary universal primer specific portion of the immobilized extension products. Extension of the hybridized primer on the immobilized extension products forms a secondary extension product. The secondary extension product is denatured and captured at an adjacent or nearby capture oligonucleotide primer on the solid support, which primer subsequently extends to form additional immobilized extension products that are complementary to the target nucleic acid molecule. This process continues until non-hybridized capture oligonucleotide primers on the solid support are exhausted.

Another suitable approach for carrying out solid phase amplification in accordance with the methods of the present invention is described in WO2013/012440 to Barany et al., which is hereby incorporated by reference in its entirety. Isothermal approaches for carrying our solid phase amplification in accordance with the methods of the present invention are described in Ma et al., *Proc Natl Acad Sci USA* 110(35):14320-3 (2013), which is hereby incorporated by reference in its entirety.

In accordance with this aspect of the present invention, the immobilized target nucleic acid molecules or immobilized extension products thereof are subjected to a ligation reaction to produce ligation products. In one embodiment of the present invention, the ligation reaction is a ligation detection reaction. The ligation detection reaction mixture comprises a ligase and one or more oligonucleotide probe sets, each probe set having a first oligonucleotide probe having a target nucleotide sequence-specific portion, and a second oligonucleotide probe having a target nucleotide sequence-specific portion. The first and second oligonucleotide probes of a probe set are configured to hybridize, in a base specific manner, on a complementary region of the immobilized target nucleic acid molecules or immobilized extension products thereof. In one embodiment, the first and second oligonucleotide probes of a probe set hybridize immediately adjacent to each other, with a junction between them, on their complementary region of the immobilized target nucleic acid or extension product thereof and are ligated together to form a ligation product. In another embodiment, the first and second oligonucleotide probes of a probe set hybridize to their complementary regions on the target nucleic acid molecule or extension product thereof with a space or gap between them. In this embodiment, a polymerase is utilized to extend the 3' end of the first oligonucleotide probe to create a junction with the second oligonucleotide probe, and then ligase ligates the two probes together to form a ligation product.

Several variations of the above described ligation reaction can be employed to enhance the specificity of ligation product generation, and therefore, target nucleic acid detection. In one embodiment, the first oligonucleotide probe bears a ligation competent 3' OH group while the second oligonucleotide probe bears a ligation incompetent 5' end (i.e., an oligonucleotide probe without a 5' phosphate). In accordance with the method of the present invention the oligonucleotide probes of a probe set are designed such that the 3'-most base of the first oligonucleotide probe is overlapped by the immediately flanking 5'-most base of the second oligonucleotide probe that is complementary to the target nucleic acid molecule. The overlapping nucleotide is referred to as a "flap". When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity. That specific FEN activity produces a novel ligation competent 5' phosphate end on the second oligonucleotide probe that is precisely positioned alongside the adjacent 3' OH of the first oligonucleotide probe. This method and variations thereof that are suitable for use in accordance with this aspect of the present invention are described in U.S. Patent Application Publication No. 2015/0038336 to Barany et al., which is hereby incorporated by reference in its entirety.

Ligase discrimination can be further enhanced by employing various probe design features. For example, an intentional mismatch or nucleotide analogue (e.g., inosine, nitroindole, or nitropyrrole) can be incorporated into the first oligonucleotide probe at the $2^{nd}$ or $3^{rd}$ base from the 3' junction end to slightly destabilize hybridization of the 3' end if it is perfectly matched at the 3' end, but significantly destabilize hybridization of the 3' end if it is mis-matched at the 3' end. This design reduces inappropriate misligations when mutant probes hybridize to wild-type target. Alternatively, RNA bases that can be cleaved by RNAses can be incorporated into the oligonucleotide probes to ensure template-dependent product formation. For example, Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety, describes using an RNA-base close to the 3' end of an oligonucleotide probe with 3'-blocked end, and cutting it with RNAse $H_2$ generating a PCR-extendable and ligatable 3'-OH. This approach can be used to generate either ligation-competent 3'OH or 5'-P, or both, provided a ligase that can ligate 5'-RNA base is utilized.

For insertions or deletions, incorporation of a matched base or nucleotide analogues (e.g., -amino-dA or 5-propynyl-dC) in the first oligonucleotide probe at the $2^{nd}$ or $3^{rd}$ position from the junction improves stability and may improve discrimination of such frameshift mutations from wild-type sequences. For insertions, use of one or more thiophosphate-modified nucleotides downstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target. Likewise, for deletions, use of one or more thiophosphate-modified nucleotides upstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target.

Other possible modifications include abasic sites, e.g., dSpacer (aka, THF tetrahydrofuran) or oxo-G. These abnormal "bases" have specific enzymes that remove abnormal base and generate ligation-competent 3'-OH or 5'P sites. Endonuclease IV, Tth EndoIV (NEB) will remove abasic residues after the ligation oligonucleotides anneal to the target nucleic acid, but not from a single-stranded DNA. Similarly, one can use oxo-G with Fpg or inosine/uracil with EndoV or Thimine glycol with EndoVIII.

In another embodiment, a probe set for the ligation reaction can further comprise a third oligonucleotide probe also having a target-specific portion that is complementary to a region of the immobilized target nucleic acid molecule or extension product thereof. In this embodiment, the second and third oligonucleotide probes of a probe set are configured to hybridize adjacent to one another on the target nucleotide sequence with a junction between them. The target specific portion of the third oligonucleotide probe has an overlapping identical nucleotide flap at the junction with the second oligonucleotide probe in a probe set that is removed by an enzyme having FEN activity when it is complementary to the target nucleotide sequence and is the same sequence as the terminating 3' nucleotide of the second oligonucleotide probe. Cleavage of the flap liberates a ligation competent 5' phosphate on the third oligonucleotide probe that allows ligation between the second and third oligonucleotide probes at the junction to form a ligated product sequence The utilization of three probes in a primer set allows for detection of longer target regions with increased specificity Flap endonucleases or 5' nucleases that are suitable for cleaving the 5' flap of the second oligonucleotide probe prior to ligation include, without limitation, polymerases the bear 5' nuclease activity such as *E. coli* DNA polymerase and polymerases from Taq and *T. thermophilus*, as well as T4 RNase H and TaqExo.

The ligation reaction utilized in the method of the present invention is well known in the art. Ligases suitable for ligating oligonucleotide probes of a probe set together following cleavage of the 5' flap on the second oligonucleotide probe include, without limitation *Thermus aquaticus* ligase, *Thermus* sp. AK16D ligase, *E. coli* ligase, T4 DNA ligase, T4 RNA ligase, Taq ligase, 9 No ligase, and *Pyrococcus* ligase, or any other thermostable ligase known in the art. In accordance with the present invention, the nuclease-ligation process of the present invention can be carried out by employing an oligonucleotide ligation assay (OLA) reaction (see Landegren, et al., "A Ligase-Mediated Gene Detection Technique," *Science* 241:1077-80 (1988); Landegren, et al., "DNA Diagnostics—Molecular Techniques and Automation," *Science* 242:229-37 (1988); and U.S. Pat. No. 4,988,617 to Landegren, et al., which are hereby incorporated by reference in their entirety), a ligation detection reaction (LDR) that utilizes one set of complementary oligonucleotide probes (see e.g., WO 90/17239 to Barany et al, which is hereby incorporated by reference in their entirety), or a ligation chain reaction (LCR) that utilizes two sets of complementary oligonucleotide probes see e.g., WO 90/17239 to Barany et al, which is hereby incorporated by reference in their entirety).

The oligonucleotide probes of a probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

As described herein the device and methods of the present invention are designed to detect, identify, quantify (i.e., copy number), and distinguish low-abundance nucleic acid molecules comprising one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases. The low-abundance nucleic acid molecules with one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases are identified and distinguished using the methods of the present invention from a high-abundance of nucleic acid molecules in the sample having a similar nucleotide sequence as the low-abundance nucleic acid molecules but without the one or more nucleotide base mutations, insertions, deletions, translocations, splice variants, miRNA variant, alternative transcript, alternative start site, alternative coding sequence, alternative non-coding sequence, alternative splicing, exon insertion, exon deletion, intron insertion, translocation, mutation, or other rearrangement at the genome level, and/or methylated nucleotide bases.

The ability to detect, identify, quantify (i.e., copy number), and distinguish low-abundance nucleic acid molecules in a sample allows for early diagnosis and prognosis of a disease state. In another embodiment, the ability to detect, identify, quantify and distinguish low-abundance nucleic acid molecules in a sample allows for the determination of a genotypes or disease predisposition.

The target nucleic acid molecules that are detected, identified and distinguished can be isolated from any suitable sample, including without limitation, tissue, cells, serum, blood, plasma, amniotic fluid, sputum, urine, bodily fluids, bodily secretions, bodily excretions, cell-free circulating nucleic acids, cell-free circulating tumor nucleic acids, cell-free circulating fetal nucleic acids in pregnant woman, circulating tumor cells, tumor, tumor biopsy, and exosomes.

EXAMPLES

The following examples are provided to illustrate embodiments of the present invention but are by no means intended to limit its scope.

Example 1—Detecting and Distinguishing Single Molecules in the Nanosensor Chambers of the uMPS Simulation Data:

Preliminary simulations generated using COMSOL® simulation software have been performed on a nanosensor chamber comprised of 8 biomolecular processors each processor measuring 20×20 µm and containing 288 pillars (1 µm×5 µm with a 250 nm spacing). For these simulations, three operational questions were addressed: (1) can all biomolecular processors of a single chamber be uniformly addressed from a common input (reduces chamber footprint) hydrodynamically with no fluid moving into the nanotube; (2) what is the capture efficiency of the TdT-tailed DNA products to the surface immobilized $dA_{30}$ primers; and (3) following thermal denaturation, could the products be efficiently directed into the nanotube sensors electrokinetically.

Figure 31:
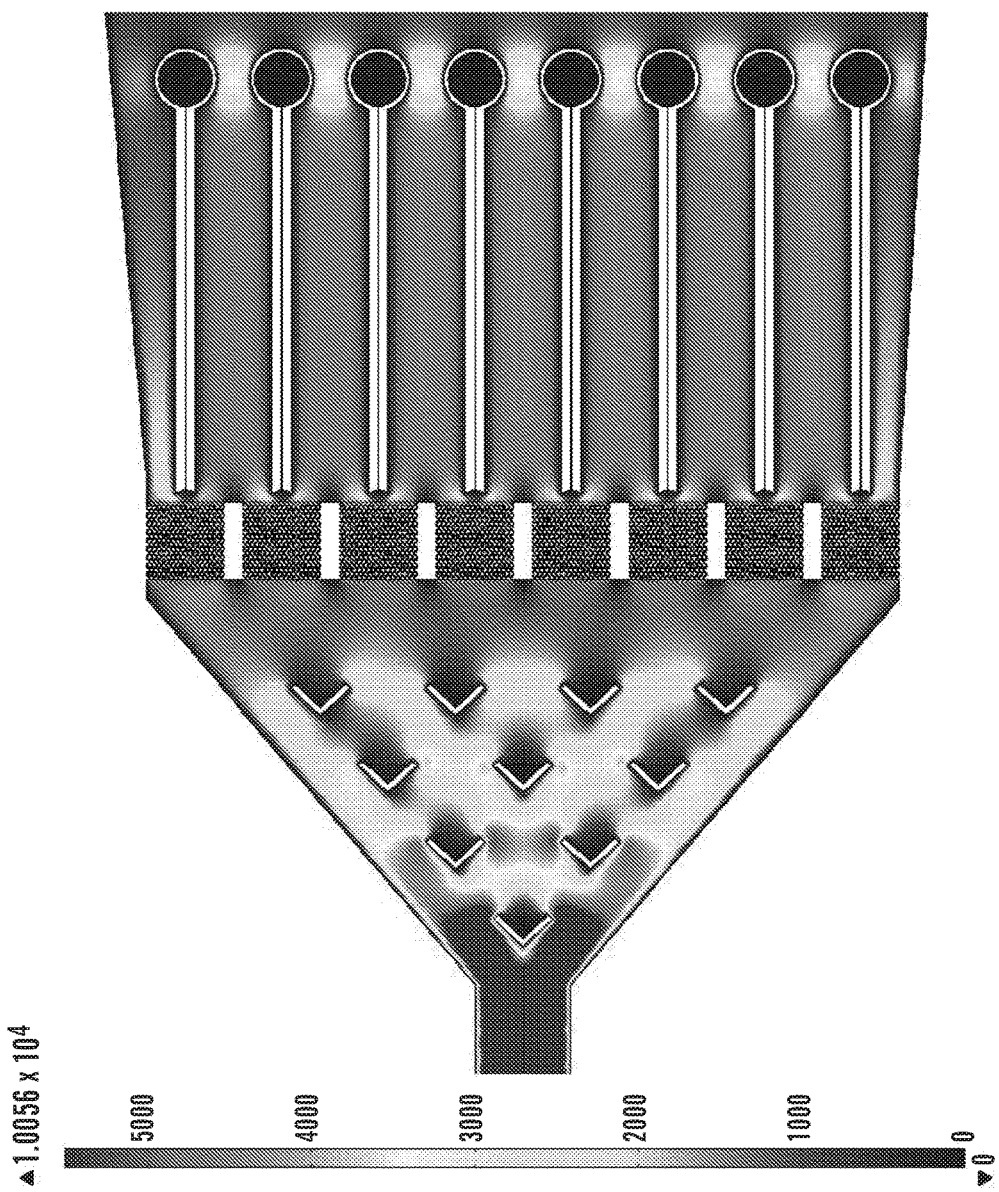
FIG. 31 shows a simulation of the fluid path through a nanosensor chamber containing eight biomolecular processors and eight nanotubes when flow is actuated via hydrodynamic pumping. The simulation shows uniform addressing of all biomolecular processors within a nanosensor chamber of a device.

For pressure driven flow (see FIG. 31), inclusion of Chevron baffles into the pre-biomolecular processor area of the chamber distributes input fluid across the entire biomolecular processor array in a substantially less amount of time then longitudinal diffusion only. In addition, due to the high fluidic resistance in the nanotube during hydrodynamic operation, arising from its small cross-section (less than 50×50 nm, with a length greater than 100 µm length), very little if any fluid enters the nanotubes due to the extraordinarily high fluidic resistance. This is convenient because during the loading and reaction phases of the assay, which will use pressure driven flow to pump in sample/reagents, all material will travel around the flight tubes as shown in FIG. 31.

Figure 32A:
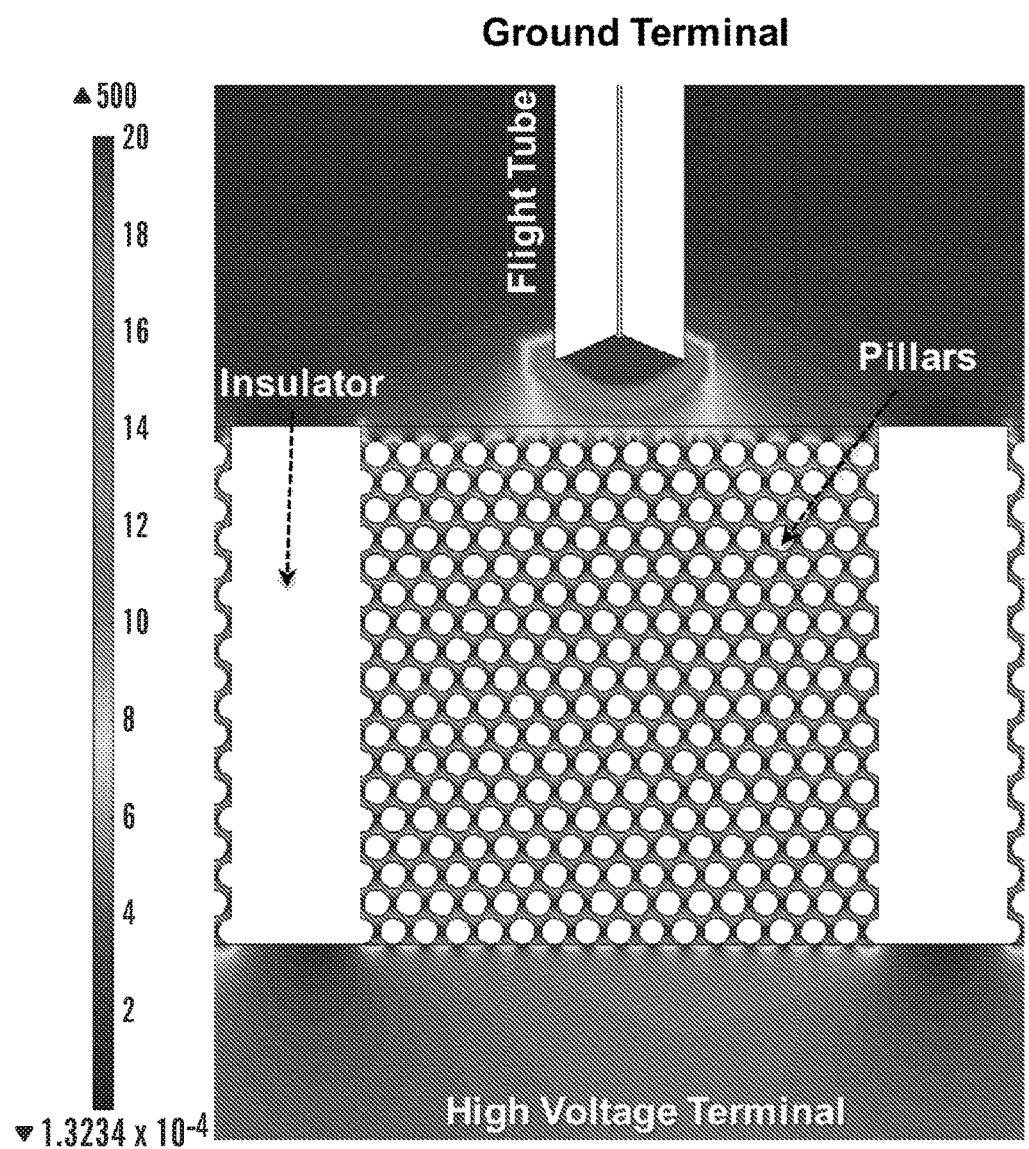
FIG. 32A shows a simulation of the fluid path through the plurality of spaced solid support structures within the bioreactor chamber of a biomolecular processor when flow is actuated via electrokinetic pumping.
Figure 32B:
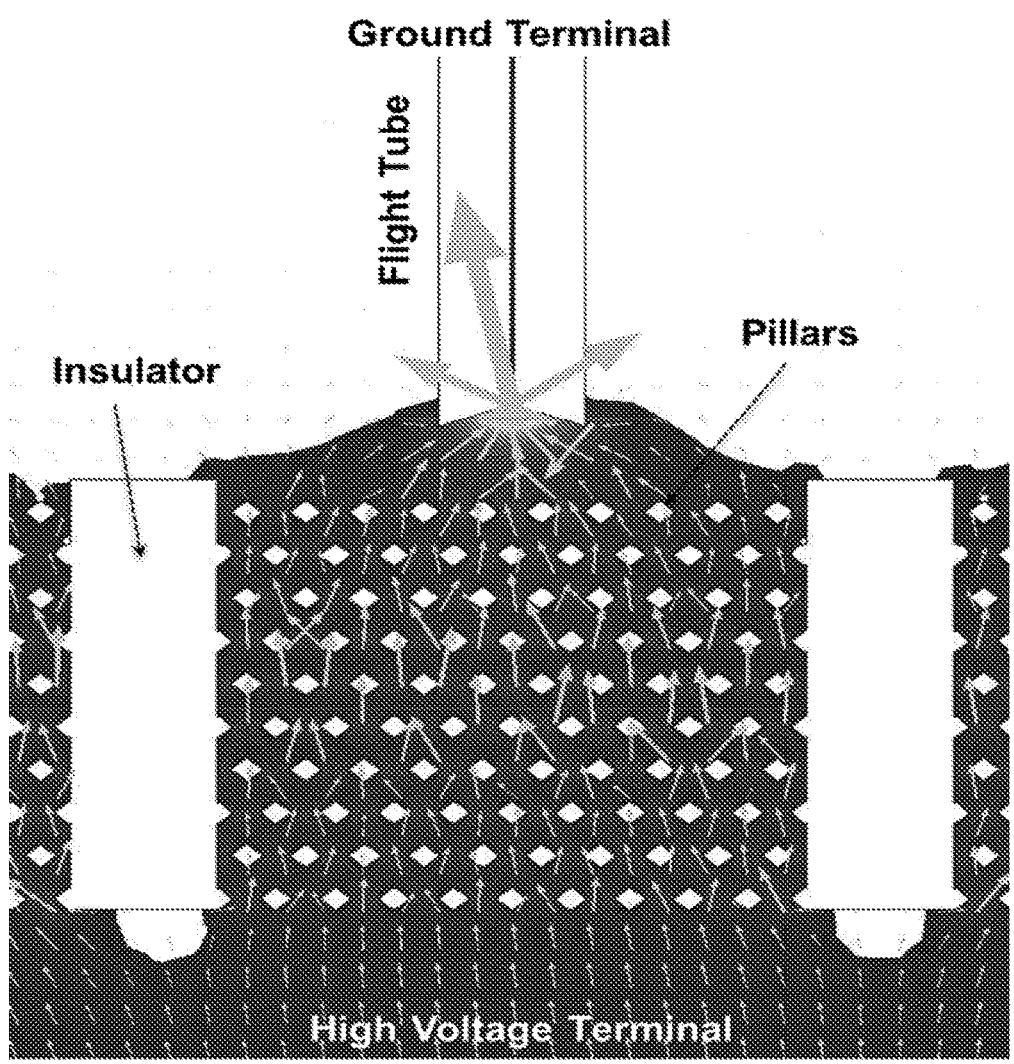
FIG. 32B shows the corresponding electric field lines through the bioreactor chamber of the biomolecular processor depicted in FIG. 32A.

However, when the chamber is actuated electrokinetically, which occurs after the solid-phase products are thermally melted from the immobilized target that are attached to the pillars of the bioreactor chamber, the thermally melted products are preferentially directed into the flight tube (FIG. 32A). As can be seen from FIG. 32A, the negatively charged products (oligonucleotides which may carry a drag tag label, but are polyanionic) are drawn preferentially into the flight tube because the majority of the electric potential drop (>95%) occurs within the nanometer flight tube. This allows for using virtual boundaries generated by the application of the electric field and the strong field lines that funnel the desired products into the flight tube (FIG. 32B). Thus, there is no need to fabricate via imprinting solid walls that would require valving operations to direct the flow of fluid in the proper direction.

Figure 33:
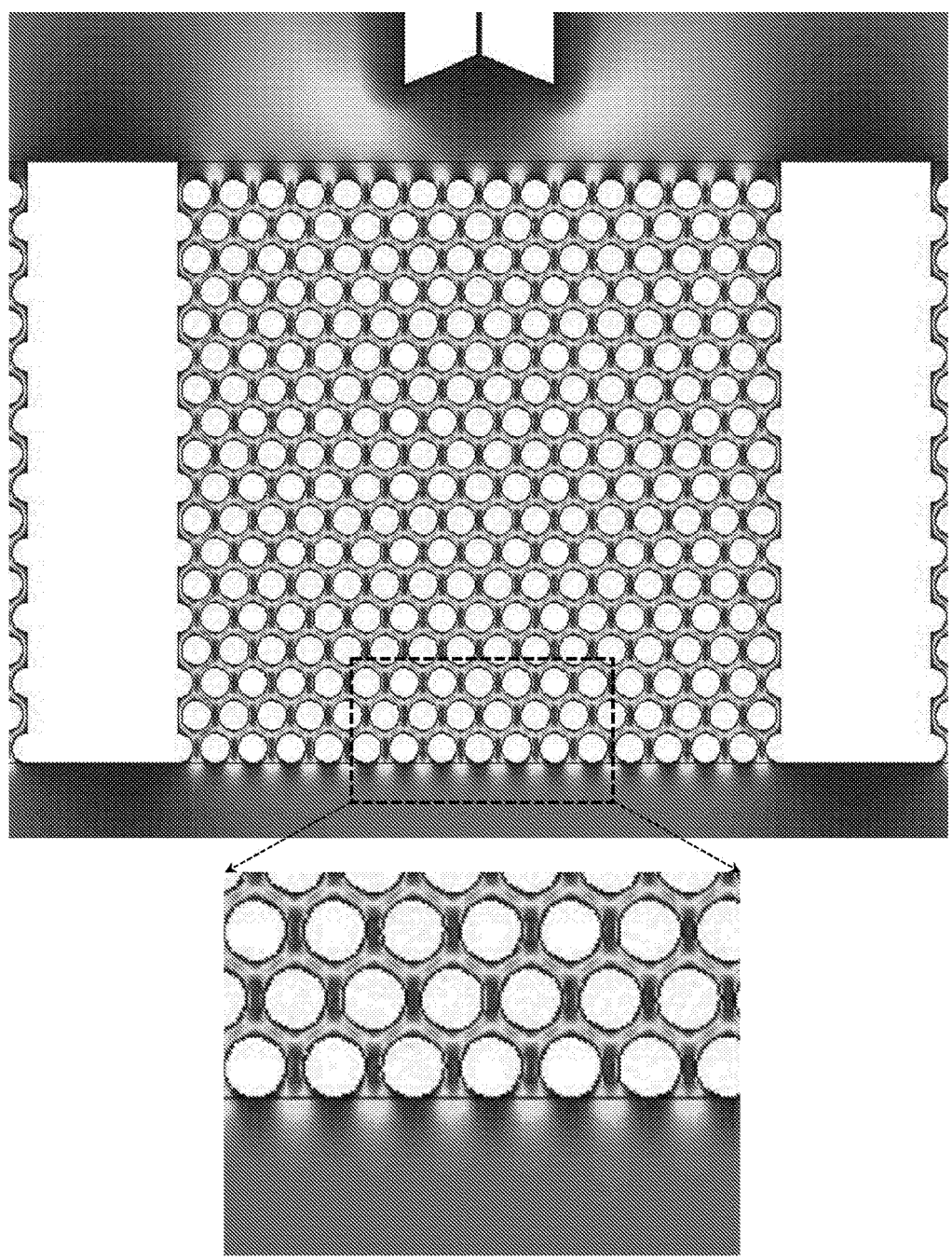
FIG. 33 shows a simulation to determine the capture efficiency of nucleic acid molecules as they move through the plurality of support structures in a single bioreactor chamber of a biomolecular processor.

Finally, using the pillar-based diffusional mode developed for predicting the recovery of pillared extraction beds and the pillar size and spacing that will be employed, the capture efficiency of the tailed DNA is >80% with equal loading onto all of the pillars (FIG. 33). This recovery is calculated for the input pillars of the single chamber component when the flow is driven hydrodynamically. Due to the use of the Chevron baffles and the uniform addressing of all biomolecular processors of a single chamber, i.e., eight biomolecule processors per nanosensor chamber (FIG. 31), there is an equal probability of capture by each pillar in the chamber. The pillars here can be of any size and shape to accommodate the given application to accommodate the load of target material required for the measurement. The pillars can be round, as shown in FIG. 31, or they can be square, diamond, rectangular shaped, etc., as described supra.

Unique to this application is a strategy that allows for the detection of single molecules traveling though nanotubes that consist of a long nanochannel and two or more in-plane synthetic nanopores. The nanopores have openings ranging from 5-50 nm and are located near the entrance and exit ends of the nanochannel, which serves as the flight tube (see FIG. 1B). When a molecule passes a nanopore, a current signature is generated depending on the ionic salt concentration and the size of the molecule, similar to what is seen in vertical nanopores, which consist of small openings in pores that are suspended on silicon nitride membranes. The nanopores can be naturally occurring pores, such as alpha-hemolysin or nanopores made via focused ion beam milling or electron beam milling in the silicon nitride membranes. Unique to this application is that the pores are in-plane with respect to the nanometer flight tube and fabricated in the same imprinting step used to create the nanofluidic network. In addition, a number of pores can be placed in series along the same path and those molecules entering/exiting the first pore and traveling into subsequent pores are sampled with 100% efficiency.

The two nanopores formed in a nanochannel will generate two current signatures, where the separation in time between the two peaks corresponds to the flight time of the thermally melted solid-phase product released from the pillars of the bioreactor chamber.

Figure 34:
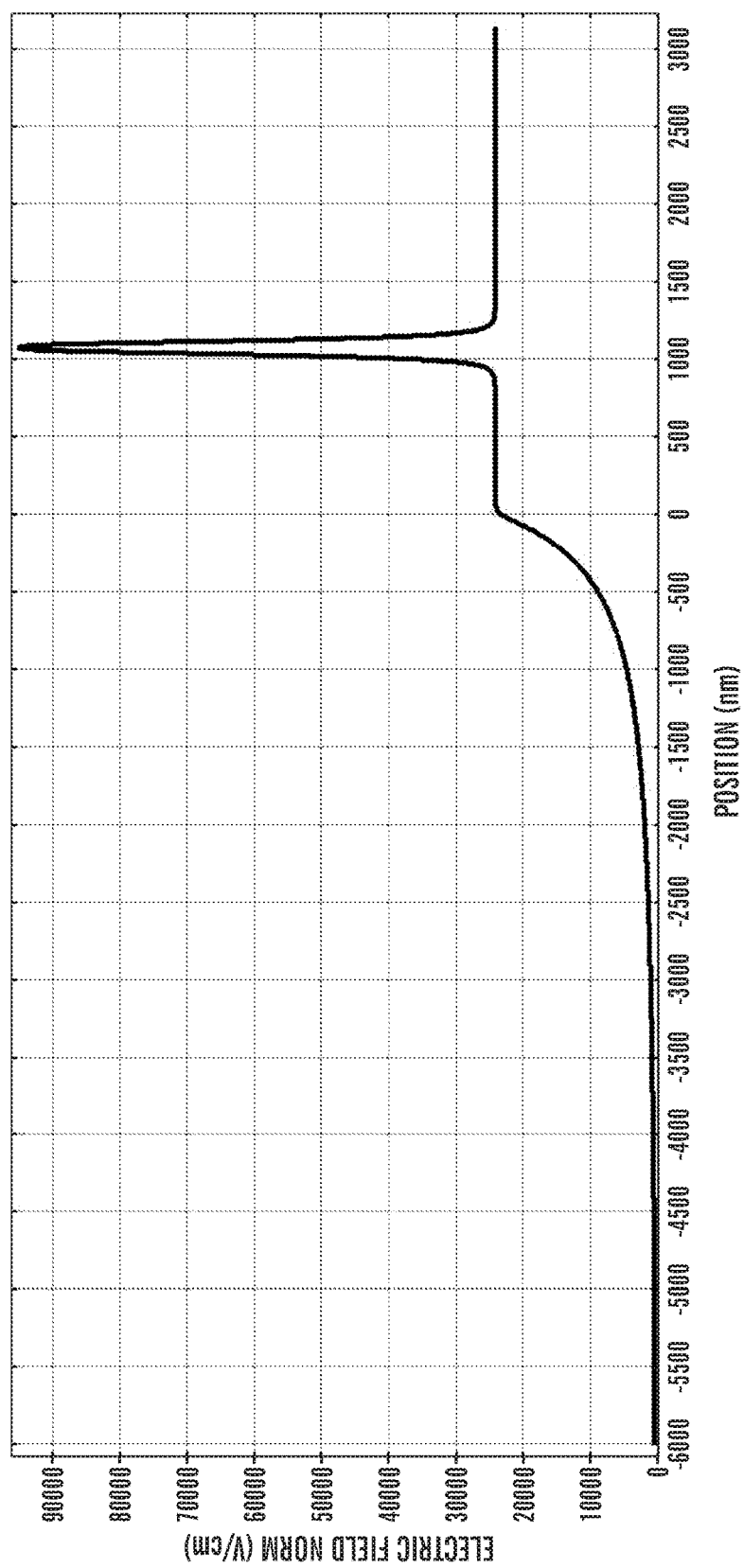
FIG. 34 is a graph showing simulated electric field distribution in a nanotube of the nanosensor module of the device of the present invention.

Extensive simulations have been carried out to demonstrate the feasibility of the in-plane synthetic nanopore strategy for detecting single molecules. FIG. 34 is a graph showing the simulated electric field distribution as a function of position within a nanotube containing a nanopore. In this example, the flight tube is 100×100 nm (w×d) and 100 µm in length with the pore being 50×50×50 nm, and the applied voltage across the tube is 10 V. However, the length of the flight tube can be 10's of microns in length to accommodate the given application. Longer flight tubes provide better electrophoretic resolution improving the identification efficiency of the single molecules. As shown in the graph of FIG. 34, when a longitudinal electric field is applied down the length of the nanometer flight tube, there is a large enhancement in the electric field across the in-plane pore due to its reduced size with respect to the flight tube. This indicates that the single molecule will speed up when traveling in this region of the flight tube.

Figure 35A:
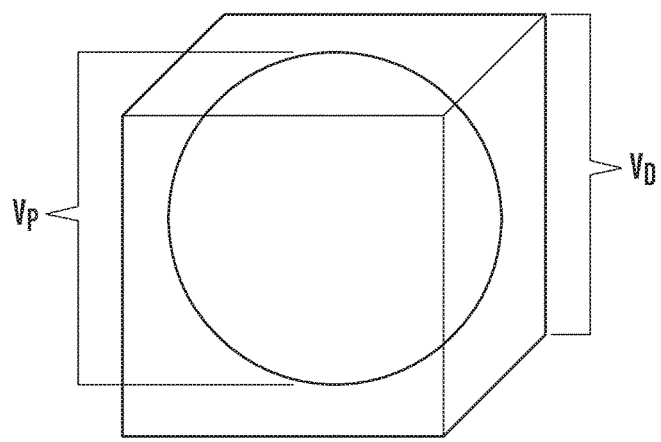
FIG. 35A is a schematic showing a spherical analyte in a nanopore, where Vp=volume of particle (analyte) and Vd=detection volume.
Figure 35B:
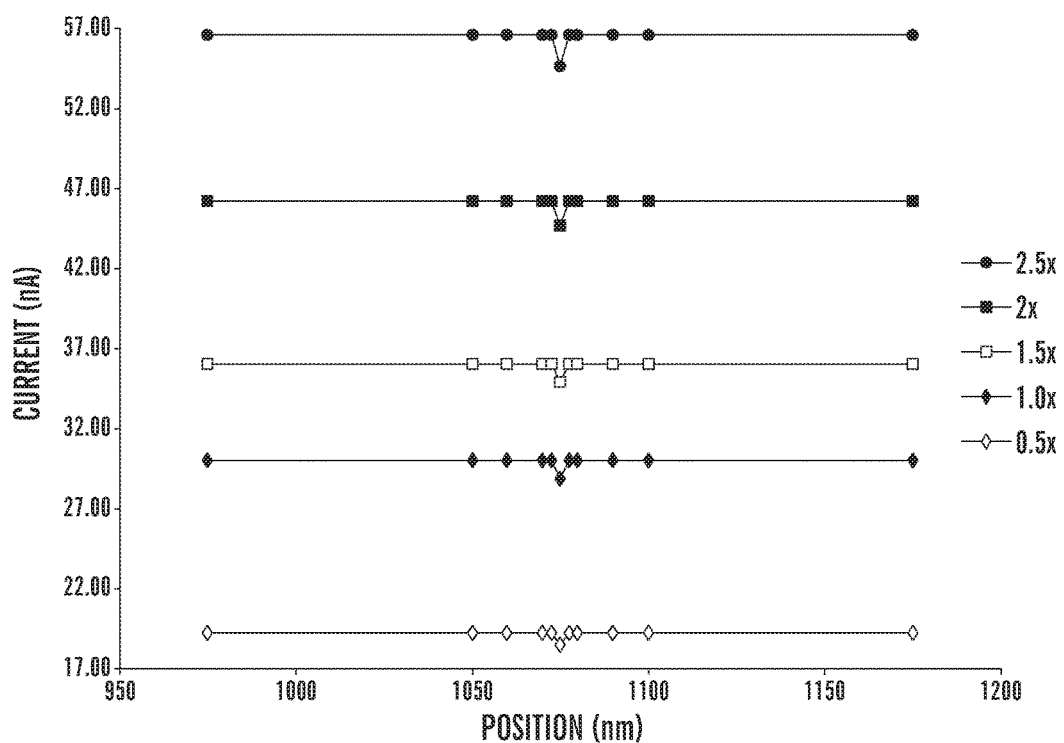
FIG. 35B is a graph showing the simulation results for a charged particle moving through a synthetic nanopore as a function of buffer electrolyte concentration. The magnitude of the blockage current depends on the carrier electrolyte concentration (TRIS/borate/EDTA buffer for 0.5×, 1.0×, 1.5×, 2× and 2.5×).

FIG. 35A shows a model of a spherically shaped particle residing within the in-plane synthetic nanopore. In this example, the spherical particle possesses a diameter of ~40 nm and the pore is 50×50 nm with a thickness of 50 nm. The current response that is generated ($\Delta I_B$) when the spherical particle is resident within the pore is predicted by $\Delta I_B \approx I(V_P/V_D)$. In this case, $\Delta I_B$ is equal to the unblocked current (I) multiplied by the ratio of the volume of the particle ($V_P$) to the interstitial volume between the pores ($V_D$). As can be seen in FIG. 35B, distinct current blockage events are generated when the particle is resident with the pore volume, $V_D$, irrespective of the ionic strength of the carrier electrolyte.

Figure 36A:
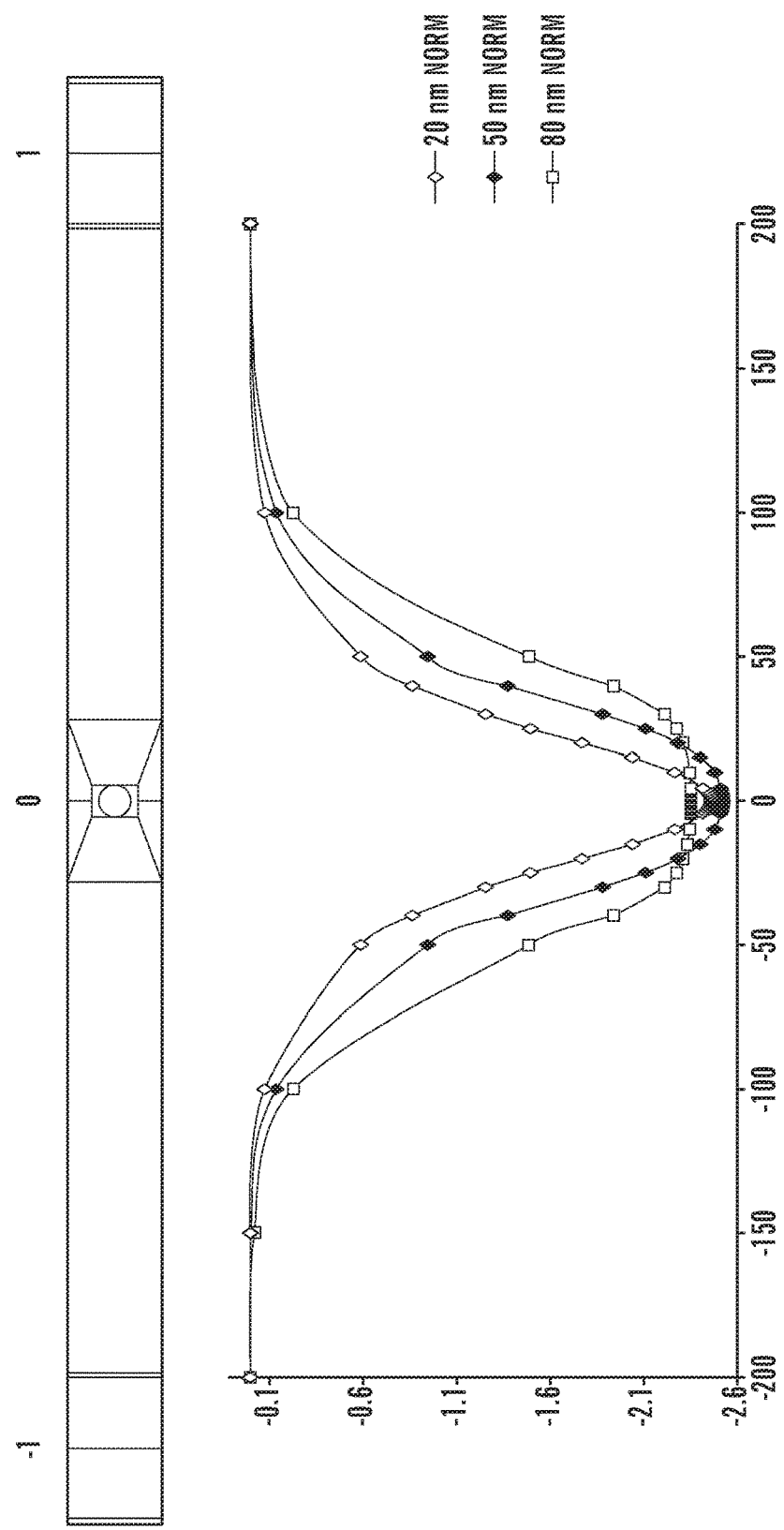
FIG. 36A is a simulation of the current blockage produced by a single DNA molecule moving through a nanopore of various lengths.
Figure 36B:
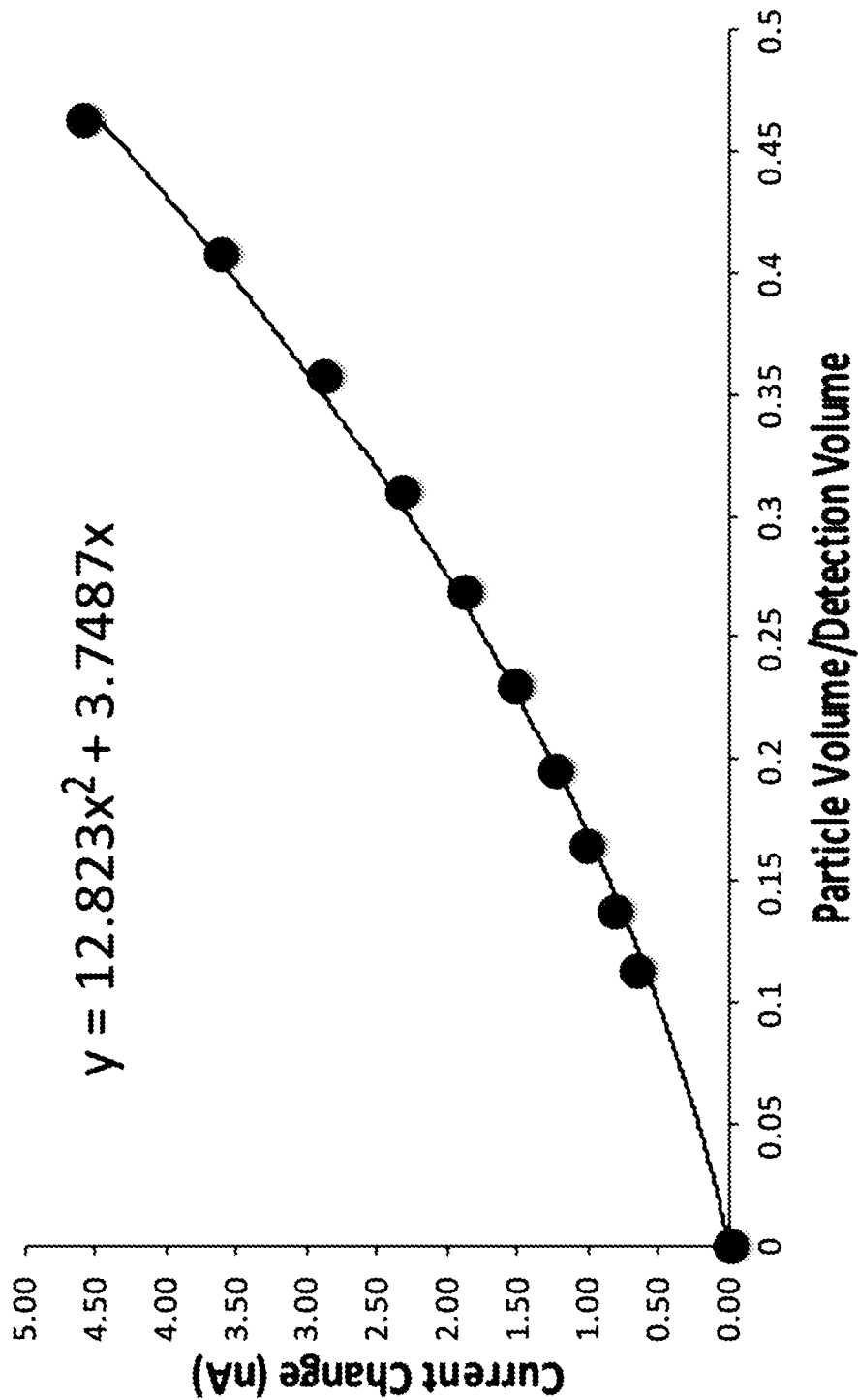
FIG. 36B is a graph depicting the magnitude of the current blockage event (nA) as a function of the spherical object/detection volume. The detection volume represents the pore volume.

FIGS. 36A and 36B show the results of a simulated current blockage produced by a single spherical DNA molecule having a 40 nM diameter moving through an in-plane synthetic nanopore of various lengths, but a constant cross section (50×50 nm). In this case, the pore length was altered at the following steps, 20 nm, 50 nm and 80 nm. As can be seen from the graph of FIG. 36A, the width of the current transient ($\Delta I_B$) peak was altered as a function of the pore length with longer pores producing wider signals. FIG. 36B shows a plot of the ratio of $V_P/V_D$ as a function of the amplitude of $\Delta I_B$. The plot was non-linear with the functional relationship shown in the accompanying graph.

These simulations demonstrate that a molecule's identifying signature, which in this case is a blockage current event, can be shaped by the pore length, i.e., larger pore length generates a broader current transient. As such, identifying signatures from different pores in the nanotube can be discerned by adjusting the length of the pore as these simulations show. Another way to change the shape of the identifying signature, i.e., current blockage event, is to change the pore diameter. Larger pores produce smaller current blockage events in terms of their amplitude.

Experimental Data:

A simple, high yield process for producing free-standing polymer membranes in SU-8 with perforated nanopores has been developed. The key feature of the process is to use a double resist layer for NIL, which is spin-coated sequentially. First, a lift-off resist (LOR) is used as a sacrificial layer, and then a negative photoresist SU-8 is used as the active layer. The micro/nanostructures are defined using NIL with Si stamps produced via lithography and wet chemical etching or deep reactive ion etching. The smallest pore achieved via a single step NIL process was ~10 nm diameter. The pore size was further reduced to ~6 nm by employing a polymer reflow process where the nanopores were placed between two plates and the polymer was heated above its respective glass transition temperature to 45° C. for 1 min. FIGS. 38A and 38B are SEM images of these SU-8 membrane conical nanopores having a diameter of 10 nm (FIG. 38A) or 6 nm (FIG. 38B). FIG. 38C is graph plotting the reduction of pore size as a function of reflow time. The size reduction rate was estimated to be 3 nm/min.

Figure 39B:
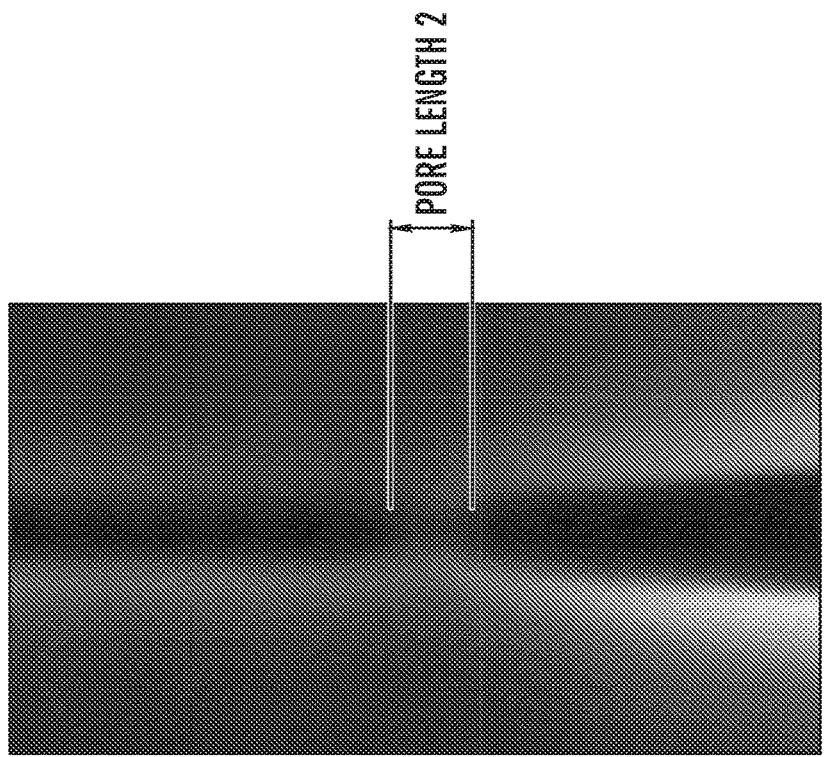
FIGS. 39A-39B are SEM images of nanopores having different pore lengths.
Figure 39A:
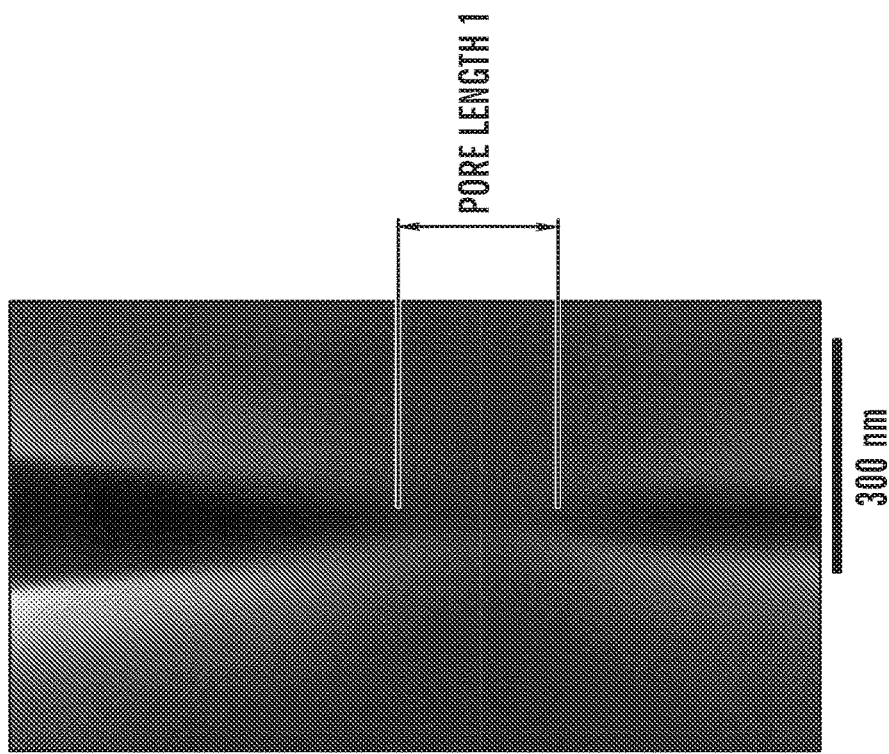

FIGS. 39A and 39B show fabricated nanotubes having nanopores of differing length.

Figure 37A:
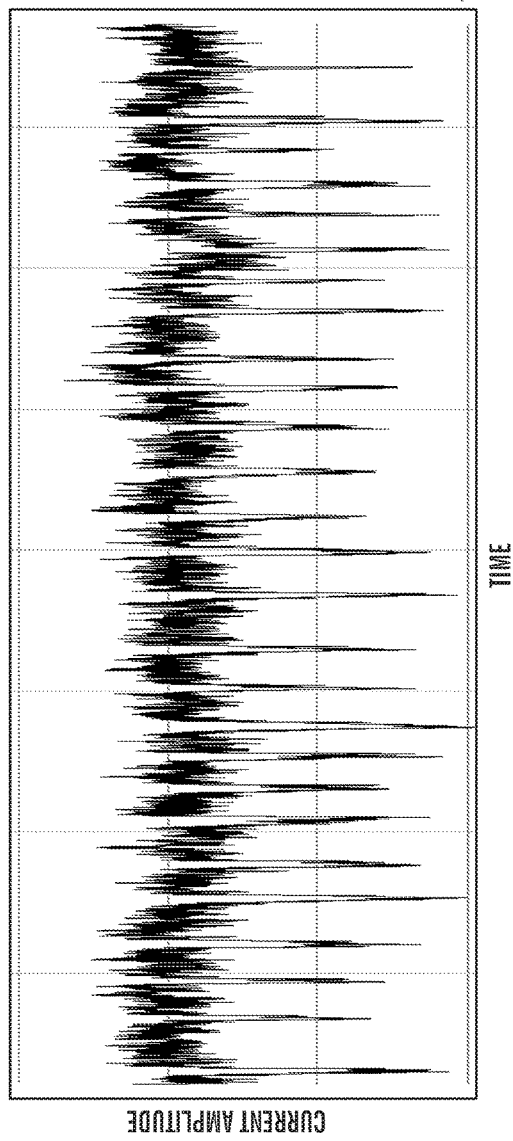
FIGS. 37A-37B show current blockage events for 500 base pair single DNA molecules electrokinetically travelling through polymer-based nanopores of two different sizes.
Figure 37B:
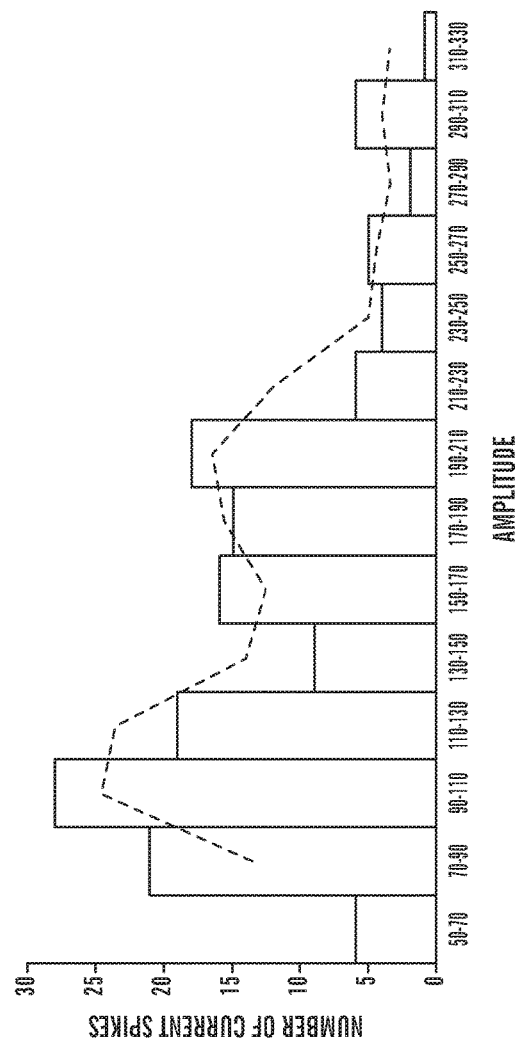

Preliminary experimental studies with the fabricated nanotubes have confirmed the simulation data. FIG. 37A shows an exemplary graph of the transient current versus time in a fabricated nanotube containing with two different size nanopores (50 nm×50 nm for the first pore and 80 nm×80 nm for the second pore). In this experiment, the nanotube was first filled with a buffer electrolyte. Then, a λ-DNA solution of the same ionic strength as the buffer electrolyte was added to the reservoir. A driving voltage was applied to electrophoretically drive the DNA molecules through the nanotube. The transient current was measured during the DNA translocation. The resulting graph of FIG. 37A shows multiple current peaks with different amplitudes. FIG. 37B shows the statistics for the amplitude of the current peaks obtained from 156 translocation events. The diagram shows a bimodal distribution with two amplitude peaks centered at 110 pA and 200 pA resulting from the two different nanopores. The result confirms that the amplitude and width of the current peak can be used as complementary molecular signatures.

Example 2—Electrophoresis for Multiplexing

The identification of the solid phase LDR (spLDR) products and other oligonucleotide products produced as a result of the solid-phase reactions being carried out on the pillars of the bioreactor chamber is based on their length (bp), which will be accomplished using electrophoretic mobility matching. This allows for mobility multiplexing with the multiplexing power determined by the peak capacity (P) of the system (multiplexing here is defined as the number of mutations that can be identified in a single analysis cycle by using different LDR primer pairs).

To test the sensitivity of the darkfield microscope to visualize single silver nanoparticles (AgNPs) in a nannochannel, a stationary AgNP (60 nm) was imaged and its localized surface plasmon resonance (LSPR) was monitored. FIG. 40A shows a three-dimensional image of the resulting signal demonstrating high sensitivity. The intensity profile was constant over time, indicating a lack of bleaching. Time-lapse images of the single AgNP (60 nm) moving through a PMMA nanochannel flight tube at an external field strength of 200 V/cm were obtained. FIG. 40B shows still LSPR images of the single AgNP moving electrophoretically through a PMMA nanochannel flight tube. The particle movement was in the direction from anode to cathode (same direction as EOF) with a transport time for this event of 1.3 s. Dimensions of the nanoslits were 100 μm in length and 150 nm in deep/width. In this case, the particle moved with a constant velocity with the absence of any intermittent motion due to stick/slip behavior.

FIG. 40C shows the electrophoretic mobility and variance in the mobilities of the single AgNPs as indicated by the plate number, N, as a function of the electric field strength. The electrophoretic mobility was found to be relatively constant irrespective of the electric field strength except at the lower field strengths (<200 V/cm) due to stick/slip motion. However, at high electric fields (>200 V/cm), the plate numbers dramatically increased.

Figure 40D:
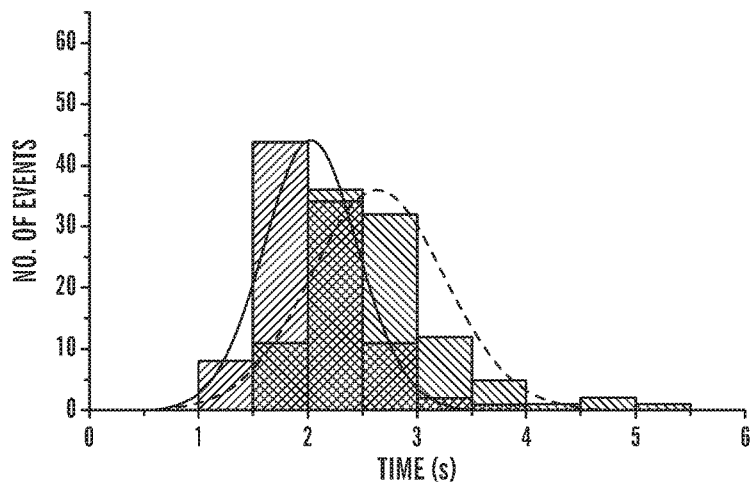
Figure 40E:
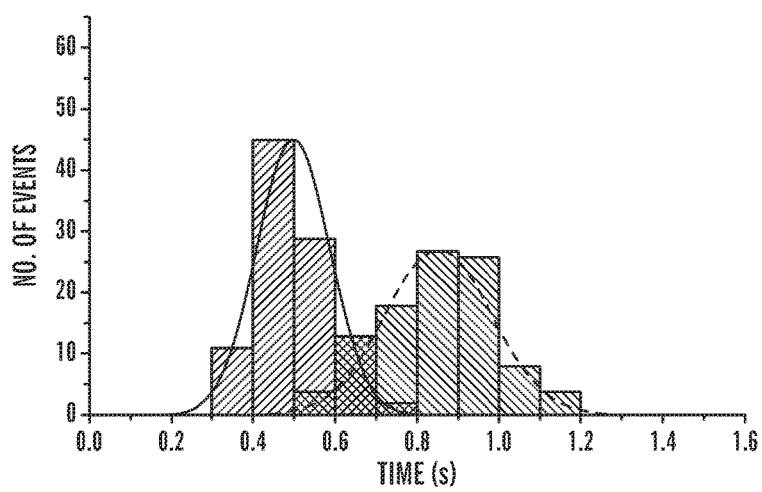
Figure 40F:
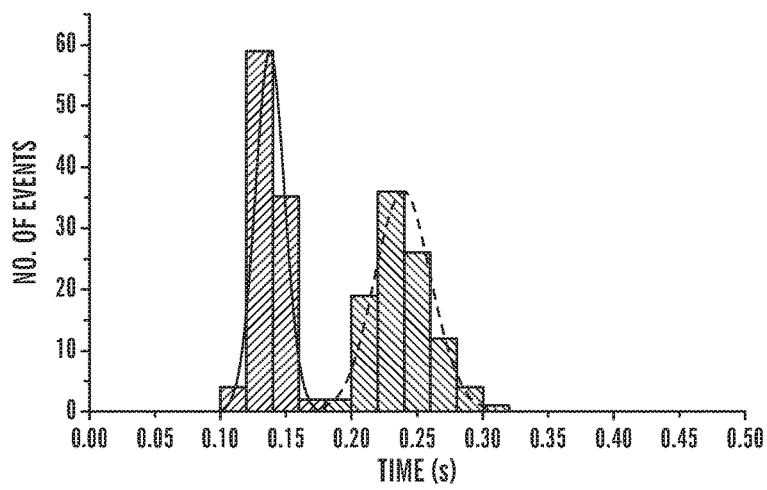

FIG. 40D-F shows histograms (100 events) of the electrophoretic flight times for 60 nm (▨) and 100 nm (▩) AgNPs transported electrokinetically through a 150 nm flight tube in 0.05 mM citrate buffer using applied electric fields of 100 V/cm (FIG. 40D), 500 V/cm (FIG. 40E), 1500 V/cm (FIG. 40F). "Stick/slip" motion of the AgNPs was observed at electric field strengths of 100 V/cm, which resulted in the broad nature of the single particle flight times. At the higher electric fields (500 and 1500 V/cm), this effect was not observed, which resulted in much narrower peak widths improving the separation of the Gaussian distributions.

Figure 41:
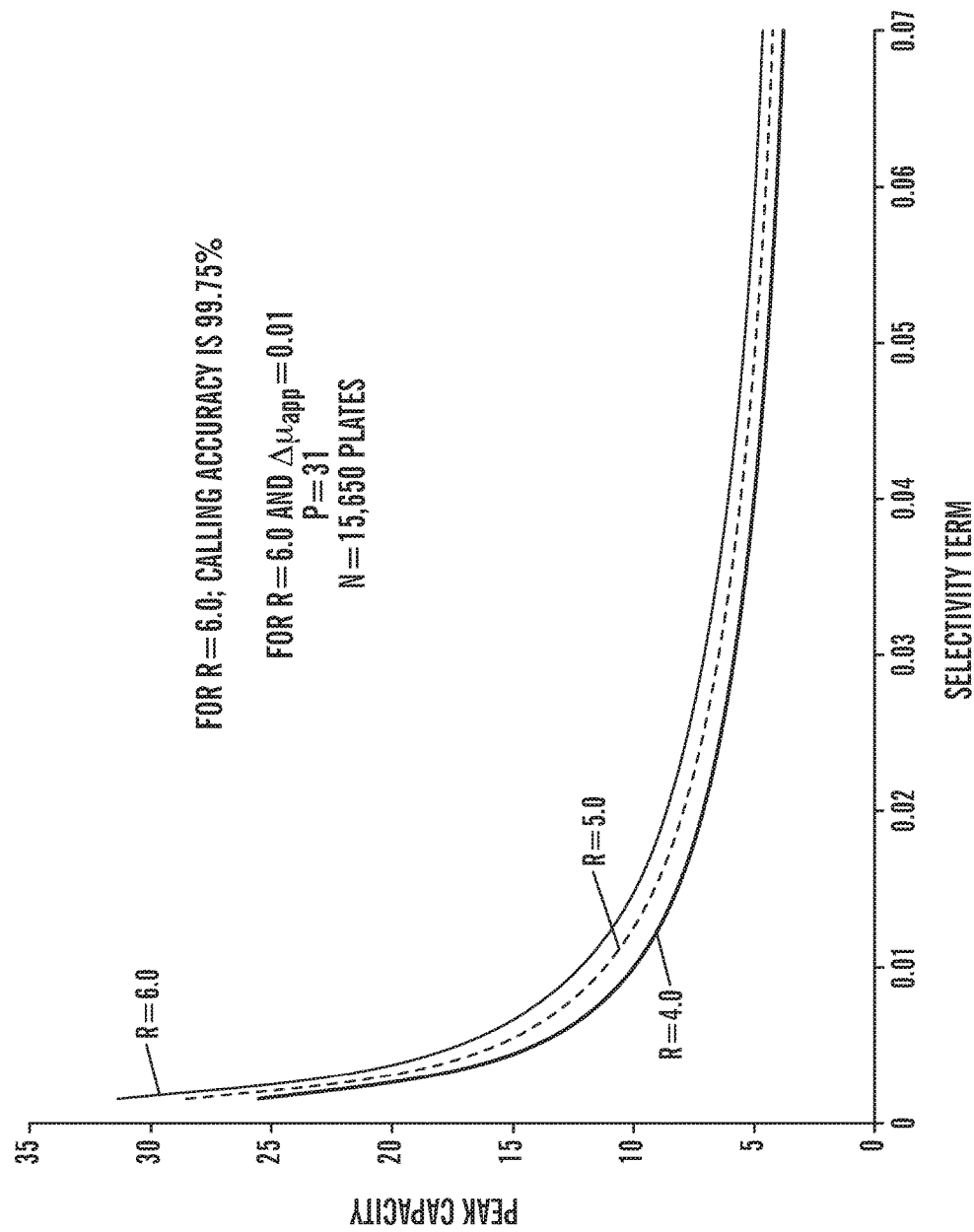
FIG. 41 is a graph showing the peak capacity as a function of the selectivity term, which is determined by the difference in the electrophoretic mobility of two components divided by the average electrophoretic mobility. For R=6.0 and 15,650 plates with a mobility difference of 0.01 the peak capacity is 31, which represents the number of biomolecules the nanotube can distinguish.

Multiplexing power is improved by using higher electric fields and/or lengthening the column. For example, increasing the field strength to 4000 V/cm and the nano-column length to 200 μm resulted in P 31 (FIG. 41). This was calculated by assuming an electrophoretic resolution of 6, which describes a classification accuracy (i.e., molecule identification accuracy based on time-of-flight) of 99.75%. The data generated in FIG. 41 were collected assuming an electrophoretic mobility difference of 0.01 ($\Delta\mu_{app}$) between two analytes with an electrophoretic plate number (N) of 15,650. The results indicate that 31 different molecular species can be identified with an accuracy of 99.75%. The peak capacity and identification accuracy are enhanced by improving the selectivity by increasing differences in the electrophoretic mobility of the spLDR products. This is accomplished, for example, by using molecular drag tags to enhance the free solution mobility differences of the oligonucleotides (Albrecht et al., *Anal. Chem.* 83:509-515 (2011); Chubynsky & Slater, *Electrophoresis* 35:596-604 (2014); Forster et al., *Electrophoresis* 30:2014-2024 (2009); McCormick & Slater, *Electrophoresis* 27:1693-1701 (2006); Meagher et al., *Anal. Chem.* 80:2842-2848 (2008); Sinville et al., *Electrophoresis* 29:4751-4760 (2008); and Albrecht et al., *Electrophoresis* 34:590-597 (2013), which are hereby incorporated by reference in their entirety). As noted in FIG. 41, when the electrophoretic resolution is 6.0 between two molecules with different flight times, the calling accuracy is 99.75%. Changing the resolution will have an effect on $N_c$, for a certain selectivity term and different plate numbers generated for the separation.

Understanding the effects of concentration polarization that can occur at polymer microchannel/nanochannel interfaces is critical, which can prevent the ssDNA products from entering the nano-scale electrophoresis flight tubes. Concentration polarization is not only determined by $d/\lambda_D$, but more importantly by the inverse Dukhin number given by $G_{bulk}/G_\sigma=(Fdzc_o/\sigma)$, where $G_{bulk}$ is the bulk conductance, $G_\sigma$ is the surface conductance, F is the Faraday constant, d is the channel critical dimension (width and depth in our case, aspect ratio=1), z is the charge, $c_o$ is the ion concentration outside of the EDL and σ is the surface charge.

For conventional capillary electrophoresis, operational characteristics are optimized to provide maximum component resolution in short times with high peak capacity. To maximize resolution, zonal dispersion is minimized and selectivity is maximized (i.e., differences in electrophoretic mobility). For zonal dispersion, there are several parameters that affect the dispersion including diffusion, injection and detection lengths, Joule heating, sample/buffer conductivity differences, and solute wall interactions. The resolution (Res) for two components (i,j) can be determined from the expression;

$$Res_{ij} = \frac{1}{4} \frac{\Delta\mu_{app}}{\mu_{app,avg}} N^{1/2} \qquad (1)$$

where N is the plate number and $\Delta\mu_{app}$ is the difference in the apparent mobility (cm$^2$V$^{-1}$s$^{-1}$) for the two components for which Res$_{ij}$ is being determined and $\Delta\mu_{app,avg}$ is the average mobility of the two components. For a well-designed system, longitudinal diffusion is the predominate dispersion effect and N can be calculated from;

$$N = \frac{\mu_{avg}V}{2D} \quad (2)$$

where D is the molecular diffusion coefficient and V is the applied voltage; therefore, Res$_{ij}$ is proportional to V$^{1/2}$. The relation shown in equation (2) is similar to the formalism provided by Xuan in which ion separations in nanochannels were evaluated (Xuan, X. *Electrophoresis* 29:3737-3743 (2008), which is hereby incorporated by reference in its entirety).

The reduced plate height (h$_i$=H$_i$/d; where H$_i$=L/N) is given by;

$$h_i = 2D_i'/dv_i \quad (3)$$

where v$_i$ is the average ion velocity for ion i, d is the channel critical dimension, and D$_i$' is the effective diffusion coefficient, which includes hydrodynamic dispersion and molecular diffusion.

As evident from equations (2) and (3), increasing the applied voltage can increase plate numbers or decrease the value of h$_i$ due to increasing the average molecular velocity. As noted from FIG. 40D-40F, extremely high electric field strengths can be used without deleterious effects on N when using nano-columns.

Theory and experimental studies for electrokinetic separations in nanochannels has appeared in recent reviews (Baldessari & Santiago, *J. Nanobiotechnol.* 4:12 (2006) and Yuan et al., *Electrophoresis* 28:595-610 (2007), which are hereby incorporated by reference in their entirety). For ion transport with d/$\Delta_d$ ratios ranging from 1-10, anomalous transport behavior has been observed, such as charge-dependent ion speeds due to transverse electromigration (TEM) resulting from wall/solute electrostatic effects (Pennathur & Santiago, *Anal. Chem.* 77:6782-6789 (2005); Pennathur & Santiago, *Anal. Chem.*, 77:6772-6781 (2005); and Xuan & Li, *Electrophoresis* 27:5020-5031 (2006), which are hereby incorporated by reference in their entirety); ion maximum resolution occurs when the column diameter is 1-10 times $\Delta_D$ (Xuan, X. *Electrophoresis* 29:3737-3743 (2008), which is hereby incorporate by reference in its entirety). Pennathur and Santiago determined that electrokinetic separations in nanochannels were dependent on ion valence, ζ (zeta potential), ion mobility and λ$_D$ (Pennathur & Santiago, *Anal. Chem.* 77:6782-6789 (2005) and Pennathur & Santiago, *Anal. Chem.*, 77:6772-6781 (2005), which are hereby incorporated by reference in their entirety). For example, Garcia et al. illustrated the electrokinetic separation of the fluorescent dyes Alexa 488 (negatively charged) and rhodamine B (neutral) in nanochannels of various widths ranging from 35 to 200 nm (Garcia et al., *Lab Chip.* 5:1271-1276 (2005), which is hereby incorporated by reference in its entirety). The mobility of the fluorescent dyes was based on their charge and interaction(s) with channel walls. Therefore, unique effects produced from nanoscale electrophoresis can be used to affect electrophoretic separations that are not possible using conventional microscale separations.

One can also use drag tags to enhance the mobility differences between the oligonucleotide products using nano-scale electrophoresis (175,176). In this case, the mobility of DNA in free solution has a constant value irrespective of the length of the DNA molecule. However, when the drag tag is attached to the DNA molecule, it relieves its free draining behavior and causes the DNA to migrate in free solution at a rate that depends on its size (longer DNAs move faster than shorter DNAs). A variety of different drag tags, such as peptides and/or proteins consisting of repeating amino acid units of unique sequence (Albrecht et al., *Electrophoresis* 34:590-597 (2013), which is hereby incorporated by reference in its entirety) or even streptavidin (Heller et al., *J. Chromatog. A* 806:113-121 (1998), which is hereby incorporated by reference in its entirety) can be used. The drag tag can be covalently anchored to one of the LDR primers. To enhance resolution by increasing mobility differences, drag tags can also be attached to the end of each primer (Meagher et al., *Electrophoresis* 27:1702-1712 (2006), which is hereby incorporated by reference in its entirety).

Figure 42:
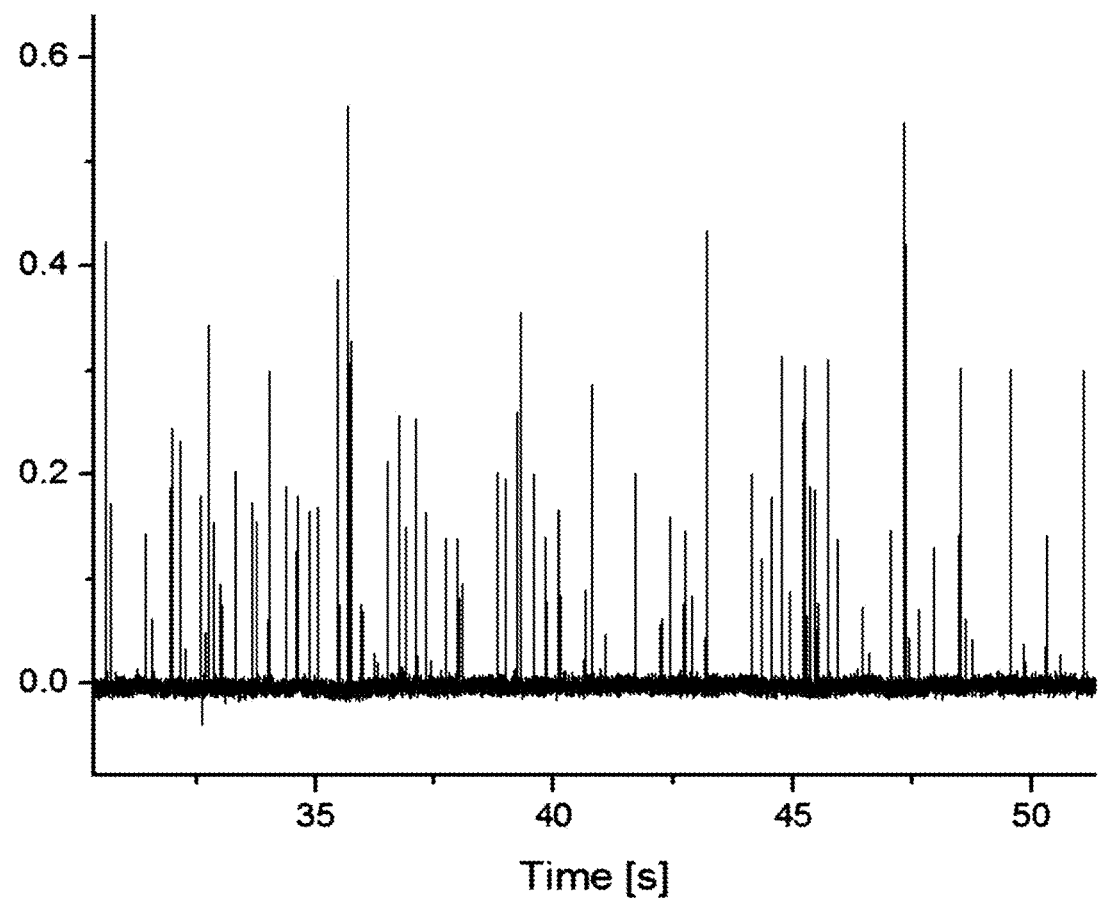
FIG. 42 shows single cell impedance measurements of breast cancer cells (MCF-7) using the sensor module of the device as described here.

Example 3—Single Cell Enumeration and Viability Assessment Using the Impedance Module As described supra, the impedance module (also referred to as the sensor module) is used to count single cells, as well as determine cell viability and cell size. FIG. 42 shows single cell impedance measurements of breast cancer cells (MCF-7) using the three-layered impedance module as described herein (shown in FIGS. 23A-23B). MCF-7 cells were introduced to the microchannel of the impedance module via the input port and were measured as they individually passed through the pair of electrodes that intersect with opposing sides of the microchannel. Each peak in the graph of FIG. 42 represents a signature from a single cell with the amplitude related to the size of the cell. The impedance measurement was made at a frequency of 40 KHz.

Figure 43:
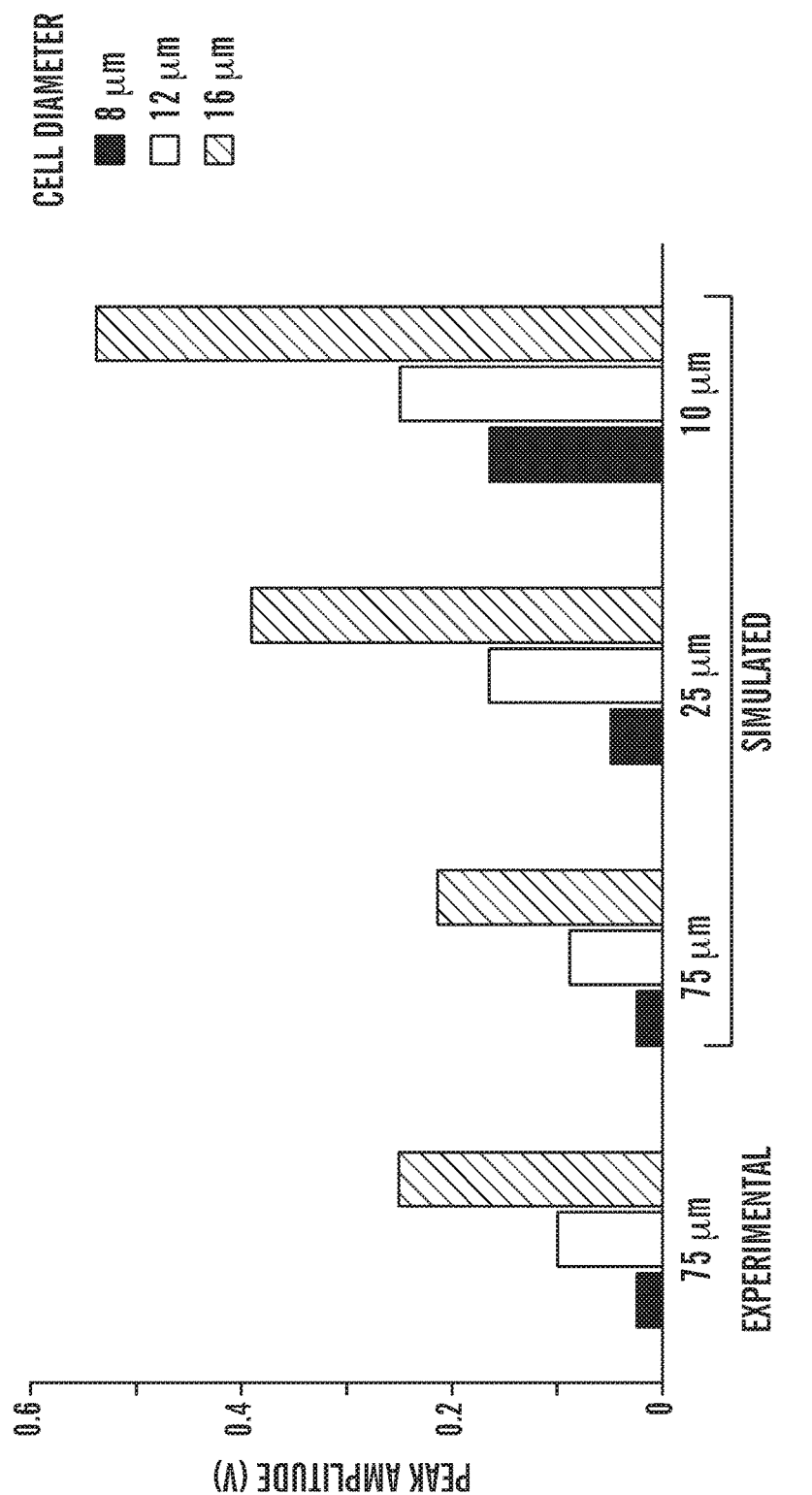
FIG. 43 is a graph of simulations showing the impedance response of different diameter cells for electrodes of different sizes (i.e., 20, 25 and 75 µm). Also shown is experimental data for the impedance peak amplitude for cells of 3 different average sizes for an electrode pair that is 75 µm wide.

Simulations, generated using COMSOL® software, were used to determine the effects of electrode size in the impedance module as a function of particle diameter to show that the relative difference in signal amplitude with particle size was not terribly affected by electrode size, but the signal-to-noise ratio was. Smaller electrodes provided better signal-to-noise ratio compared to larger electrodes. FIG. 43 is a graph of the simulation data showing the impedance response of different diameter cells for electrodes of different sizes (i.e., 20, 25 and 75 μm). Also shown is experimental data for the impedance peak amplitude for cells of three different average sizes (i.e., 8, 12 and 16 μm) for an electrode pair that is 75 μm wide.

Figures 44A, 44B:
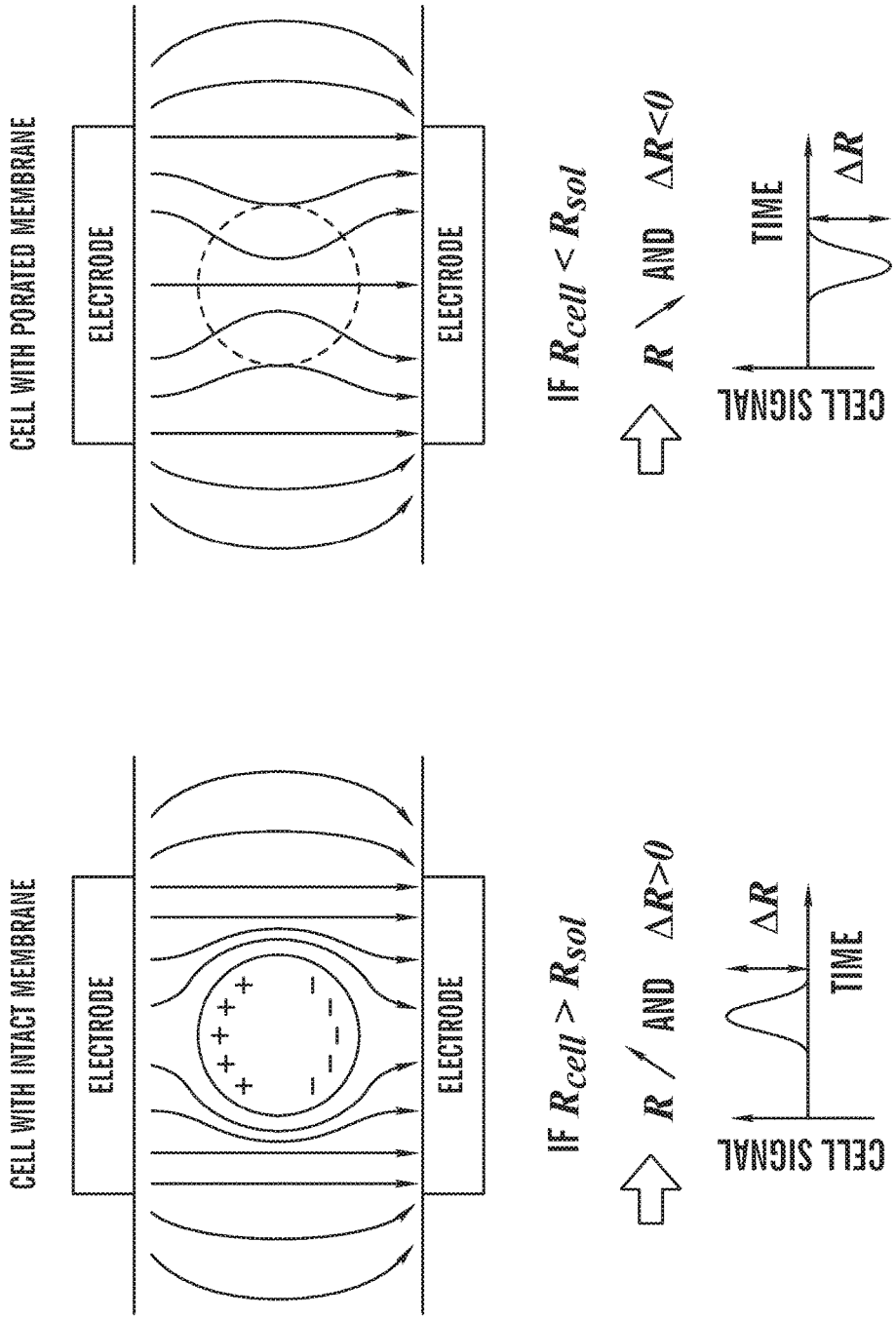
FIGS. 44A and 44B are diagrams illustrating the origin of higher than buffer-only resistance registered for intact cells (FIG. 44A) and drop in resistance for cells containing membranes that are compromised (FIG. 44B). $R_{cell}$ is the resistance of cell, and $R_{sol}$ is the resistance of volume of solution equal to volume of cell.

Unique to the three-layered impedance module described herein is its ability to determine cell viability. The signal measured by the impedance sensor is proportional to the resistance of the medium between the electrodes and can be used to determine cell viability. When no cell is present between the electrodes the signal is proportional to the resistance of the buffer solution and this defines the baseline for the measurements. Every cell passing between the electrodes replaces a small volume of the buffer solution. Intact cells are considered non-conductive at the frequency of the electrical signal (40 kHz) applied between electrodes due to high cell membrane capacitance. Thus, the small volume of the solution replaced by the cell has higher resistance than the corresponding volume of the buffer alone. This leads to an increase in the overall resistance measured by impedance sensor, which presents itself as positive peaks recorded for a passing cell as demonstrated in FIG. 44A. When the cells' membrane is compromised, the cell resistance can be approximated by the resistance of the cell interior, which is composed primarily by cytoplasmic components. If the resistance of cell cytoplasm is lower than that of the corresponding volume of buffer solution, the overall resistance measured by sensor drops, which results in a negative peak (FIG. 44B).

Figure 44C:
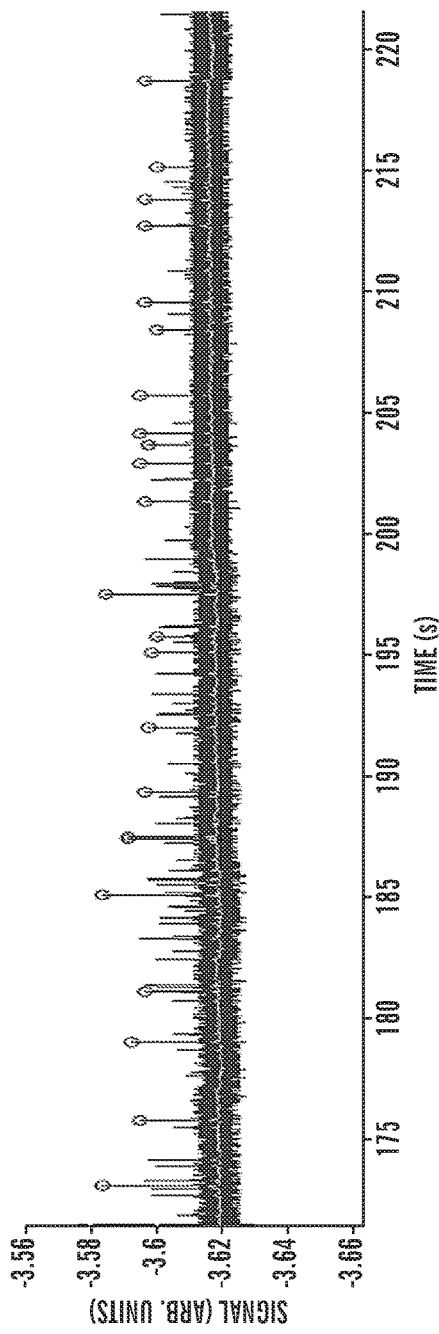
FIGS. 44C and 44D are impedance traces for Hs578T live cells in 1×TG buffer (FIG. 44C), and paraformaldehyde and Triton X-100 treated cells in 1×TG buffer (FIG. 44D).
Figure 44D:
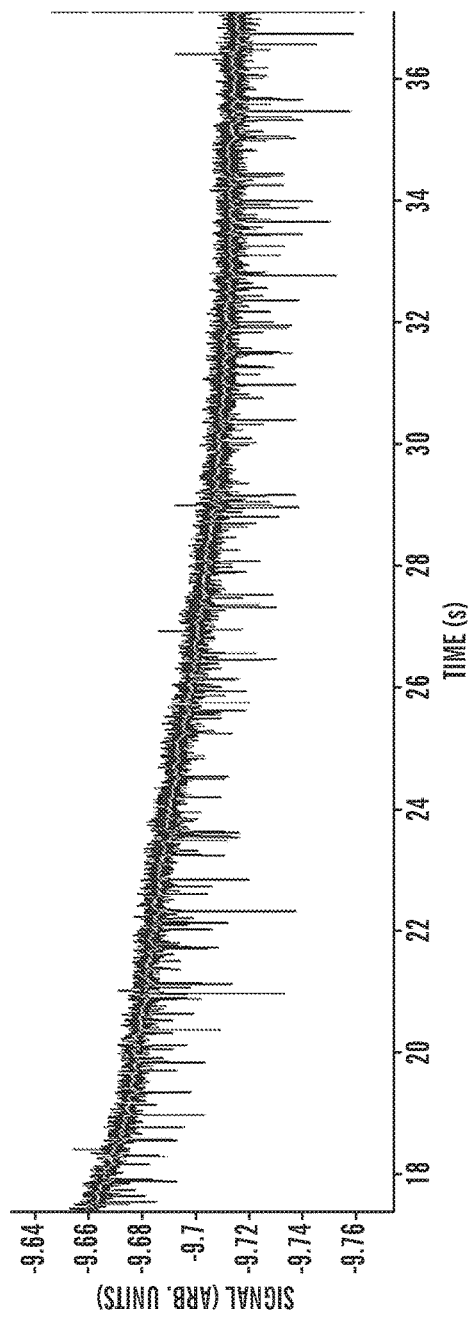

To demonstrate the functionality of the impedance module to distinguish viable and non-viable cells, live and fixed Hs578T cells that were gentle permeabilized were re-suspended in 1× TG buffer introduced into the impedance sensor. FIGS. 44C and 44D show traces for live cells and fixed cells, respectively. For live cell suspensions, only positive peaks consistent with intact membranes were observed. For fixed and slightly permeabilized cells, positive and negative peaks were observed. Clearly, cells having compromised membranes (i.e., permeabilized) provide electrical sensing of the cell interior thus generating a resistance or impedance lower than in the absence of the cell for the solution volume between the electrode pair creating negative polarity peaks in the trace with respect to the carrier electrolyte. These conclusions are also supported by other experiments showing that cells treated with formaldehyde only produced predominantly positive peaks (cross-linking of the cell membrane), while cells exposed to prolonged incubation with Triton X-100 after fixation showed only negative peaks (compromised cell membrane).

Example 4—Exosome Extraction on the uMPS

Computational fluid dynamic simulation experiments have been carried out to investigate plasma flow through a solid-phase extraction bed for exosomes isolation. The SPE bed in these simulations is comprised of diamond micropillars with 15 μm side length and 5 μm spacing (see FIG. 45A). Besides regions near the corners of the micropillars, the flow dynamics in the SPE bed can be approximated using a simplified parabolic velocity profile that is typical of Poiseuille flow, which greatly reduces the computational cost for simulating exosome dynamics in the moving fluid. Here, the effective microchannel width is given by the micropillar spacing and the length of the channel by the SPE bed's end-to-end length that is then amplified by a path correction factor, which adjusts for the distance spanned around the pillar. The physical properties of the exosome used for the Monte Carlo simulations are summarized in Table 1 below.

Both convective and diffusive transfer of exosomes is then simulated via Monte Carlo methods. The position of an exosome is propagated over incremental time steps (Δt). The exosome's position is first convectively moved using the Poiseuille flow profile with the exosome's axial and longitudinal position perturbed by diffusive dynamics, which are approximated with a pseudo-random number generator that is normally distributed about the exosome's position with a given by $\sqrt{2D\Delta t}$, where D is the exosome's diffusion coefficient (see FIG. 45B).

Each encounter with a micropillar surface may or may not lead to successful SPE of the exosome to the surface that is decorated with an antibody associated with an antigen found in the membrane of the exosome, and these reaction dynamics are assessed by comparing the probability of antibody/antigen association according to Chang-Hammer dynamics with a pseudo-random number generator with uniform distribution. Note that the simulations are repeated until the resultant recovery converges with respect to the number of exosome trajectories simulated and the time discretization.

Additionally, for every simulation, the recoveries from 41 different axial starting positions were averaged to represent an initially homogenous exosome solution.

TABLE 1

Physical Properties of the Exosome Used for the Monte Carlo Simulations.

| Exosome Property | Value |
|---|---|
| Size | 50-150 nm |
| Diffusion Coefficient | 5-15 μm²/s |
| Exosome Antigen | CD63 |

Figure 46:
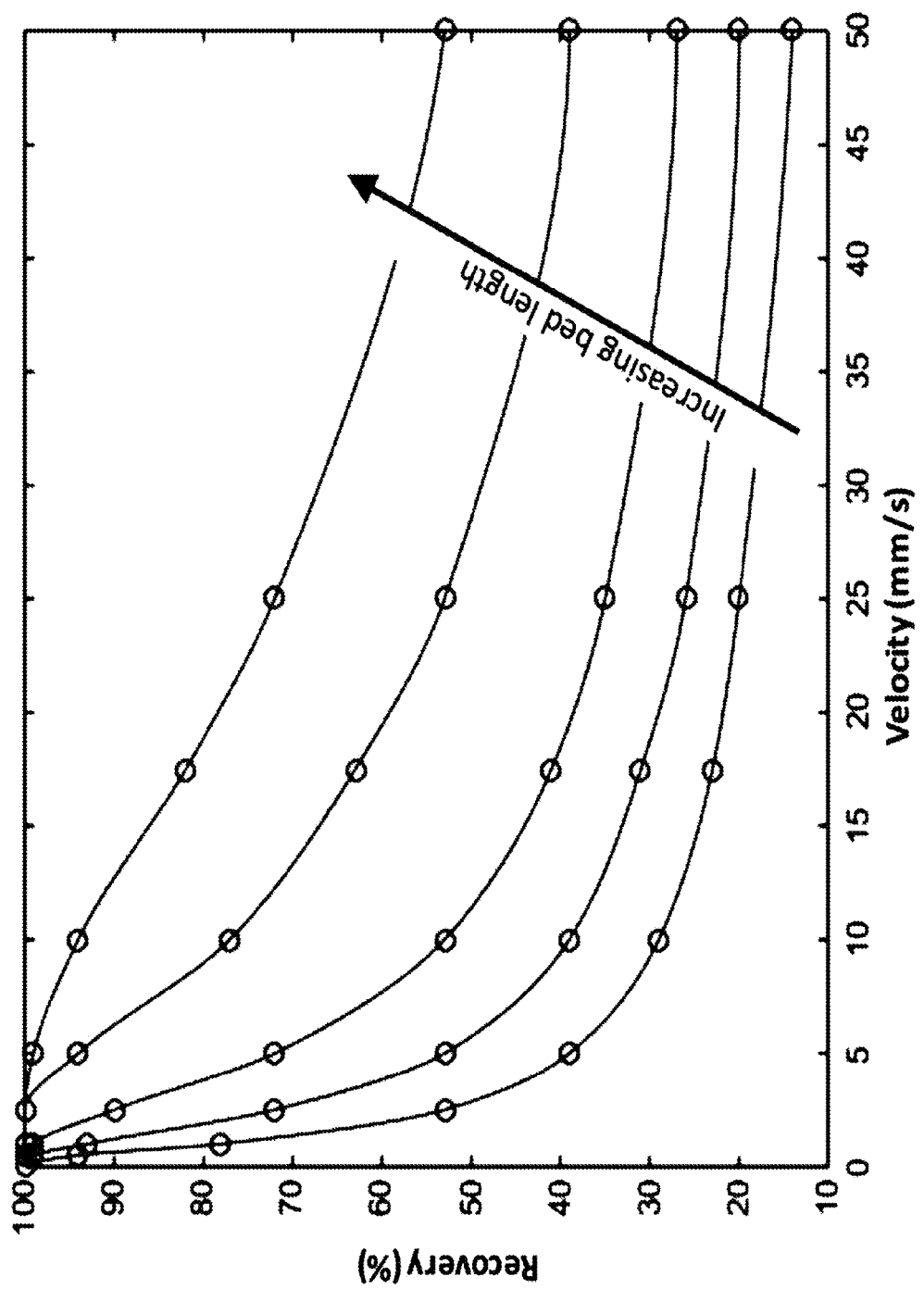
FIG. 46 is a graph showing the effects of velocity and SPE bed length on exosome recovery using the simulation depicted in FIG. 45A.

FIG. 46 is a graph showing the effect of velocity and extraction bed length on exosome recovery in the simulation experiments. For each pillar spacing and bed length, velocity was varied and recovery was assessed. The bed lengths used here were 2.5 mm, 5 mm, 10 mm, 25 mm, and 50 mm. The pillars were 15 μm in size with a spacing of 5 μm. As shown in FIG. 46, exosome recovery is maximized at lower velocities through longer extraction beds.

Figure 47:
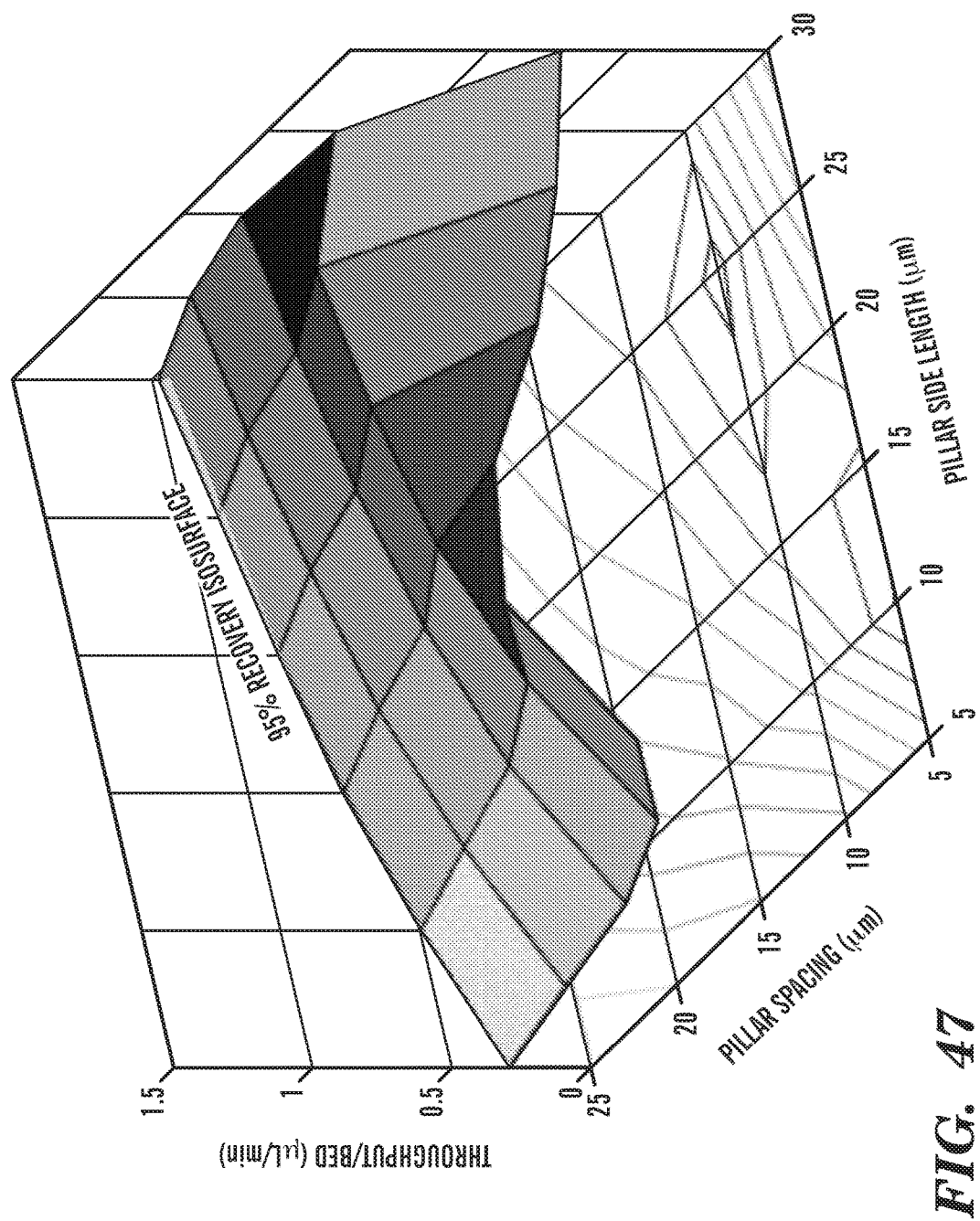
FIG. 47 is a 3D isosurface and underlying contour plot for conditions which exosome recovery is predicted to be 95% by the Monte Carlo/Chang-Hammer simulations of FIG. 45B.

FIG. 47 is a 3D isosurface and underlying contour plot for conditions at which exosome recovery is predicted to be 95% by the Monte Carlo/Chang-Hammer simulations. Note that SPE bed length is kept constant at 50 mm for this graph. Throughput is derived from the velocities output by the simulations. Bed width was constrained to 2 mm to provide longitudinal pressures that reduce the probability of air bubbles in the SPE device, which affected the number of pillar and open conduits between pillars that affect throughput. Two conditions are noted which provide both high recovery and a maximal throughput of 1.4 μL/min per SPE bed: Pillar dimensions of 10 μm×5 μm×20 μm and of 25 μm×10 μm×100 μm (side length×spacing×height). Also noted is that the large pillar dimensions require over an order of magnitude lower pressure for plasma infusion, which lends to simpler incorporation of multiple SPE beds in serial connection (for extracting exosomes with orthogonal markers) and incorporation of the SPE system into more complex, integrated microfluidic networks that can perform further assays on the same blood sample.

Figure 48:
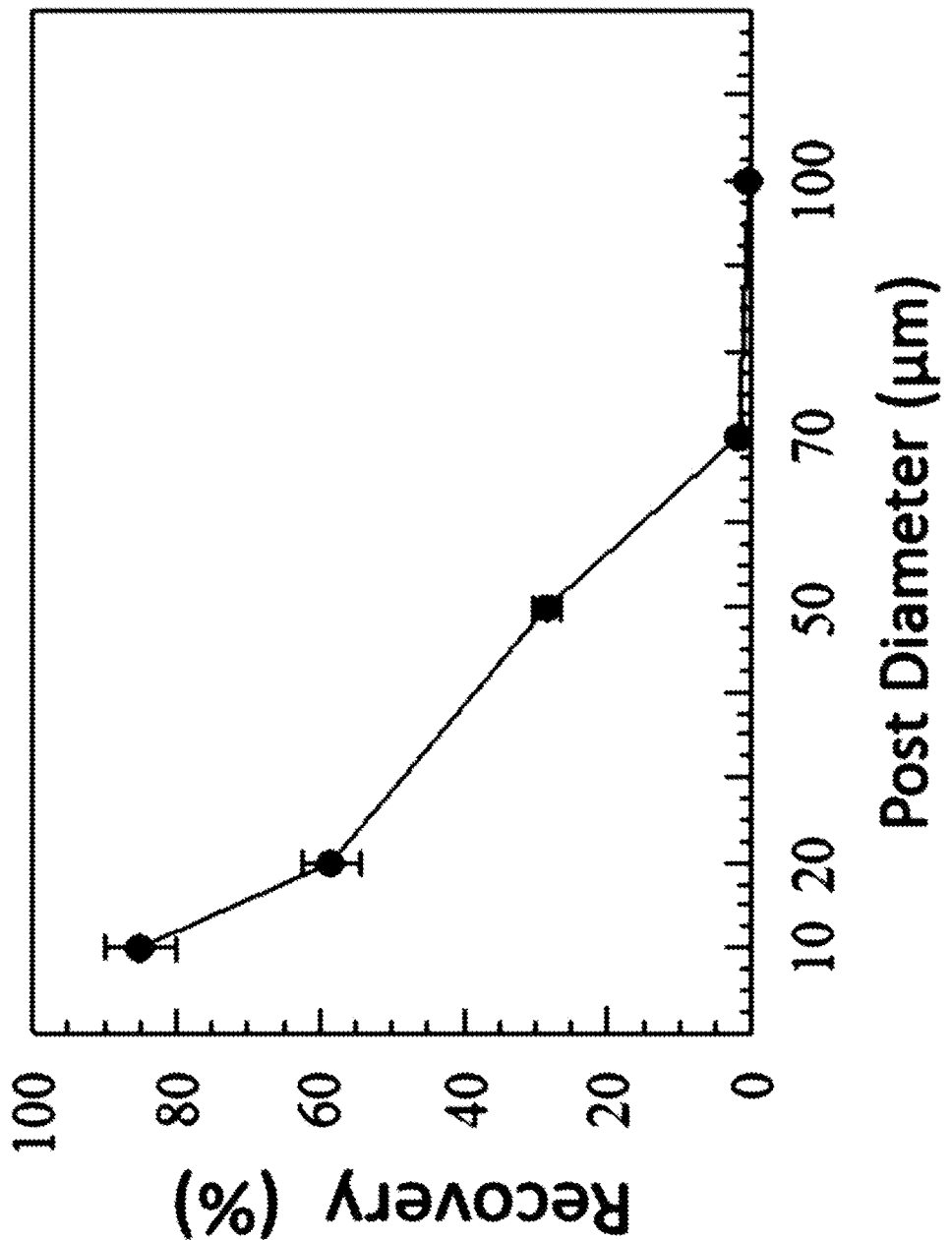
FIG. 48 is a graph showing the recovery of DNA molecules from plasma in the SPE DNA/RNA isolation module of the uMPS device as a function of the pillar diameter. The recovery increases when the pillar diameter is <70 µm in diameter.

Example 5—Nucleic Acid Extraction Via the Solid Phase Extractor Module of the uMPS A solid phase extractor (SPE) unit was fabricated using injection molding of a plastic. The unit consists of a bed of micropillars having a gradient of sizes from input to output that allows some filtering of particulates from entering the SPE bed. The graph of FIG. 48 shows that the recovery of DNA/RNA is highly dependent on the pillar diameter with a similar spacing. For example, using 10 μm pillars that are spaced by 10 μm can provide a DNA recovery that is >80%. Table 2 below shows the effect of pillar size and spacing on the bed volume and genomic DNA load. For a 10 μm pillar size and 10 μm spacing, a single SPE bed can accommodate 190 ng of genomic DNA with a volume of 120 nL.

TABLE 2

Effect of Pillar Size and Spacing on SPE Bed Volume and Genomic DNA Load

| Post Diameter (μm) | Post Spacing (μm) | Bed Volume (nL) | gDNA load (ng) |
|---|---|---|---|
| 10 | 10 | 120 | 190 |
| 50 | 40 | 230 | 94 |
| 70 | 100 | 390 | 5.6 |
| 100 | 150 | 590 | 1.3 |

Figure 49:
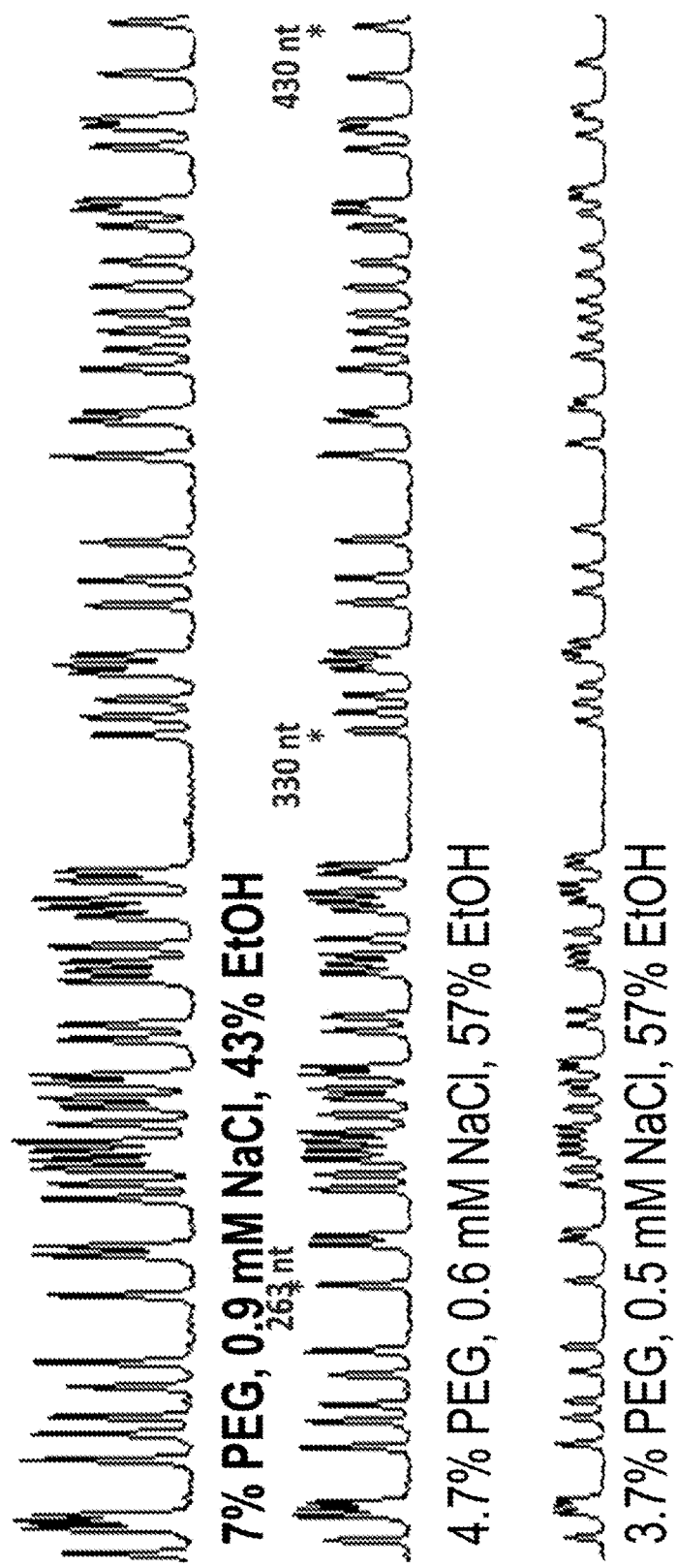
FIG. 49 shows capillary gel electrophoresis of DNA fragments recovered using the SPE module of the uMPS. Recovery was as a function of the PEG/NaCl/EtOH content, with maximum recovery observed at 7% PEG, 0.9 mM NaCl and 43% EtOH.

The polycarbonate SPE bed that has been UV activated can be used to isolate short DNAs, similar in size to cfDNA and the efficiency of isolation is dependent on the composition of the immobilization buffer, which is comprised of polyethylene glycol (PEG), sodium chloride (NaCl) and ethanol (EtOH). As seen in FIG. 49, the maximum recovery of the DNA occurs for an immobilization buffer composition of 7% PEG, 0.9 mM NaCl and 43% EtOH. The SPE module can also be used to pre-concentrate the cfDNA as well. The DNA can be enriched from an initial starting volume of 1 mL plasma to a final volume of 10 μL ($10^2$ enrichment factor).

Figure 50:
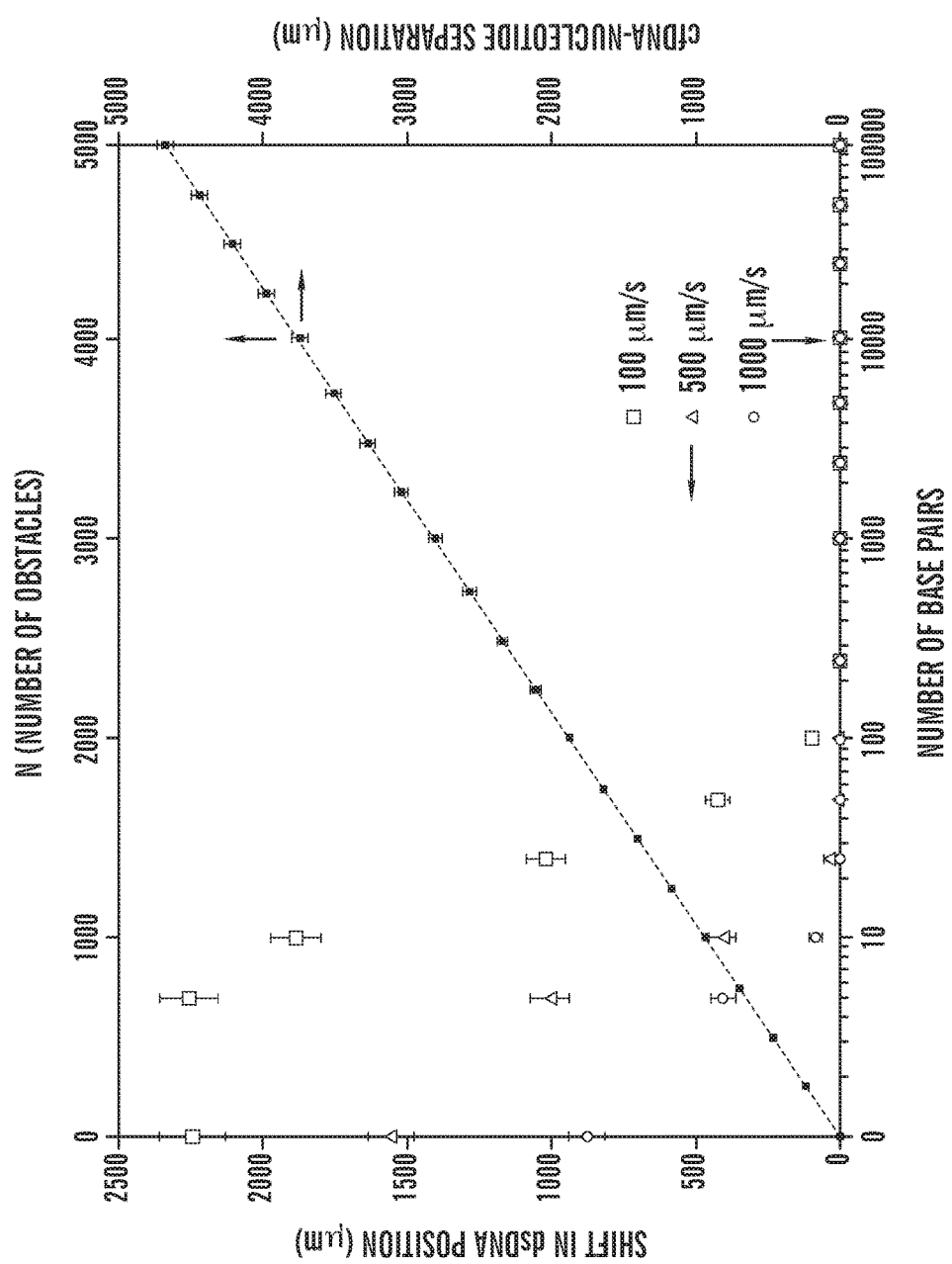
FIG. 50 is a graph showing the diffusional displacement of DNAs with different base numbers in the diffusional purification module. Also shown in the cfDNA to dNTP displacement as a function of the number of obstacles.

Example 6—Purification of Target Nucleic Acid Molecule Via the Diffusional Purification Module The diffusional flow purification module of the uMPS device is designed to purify the target nucleic acid molecules that are generated in other upstream units of the device from excess dNTPs and/or other non-target nucleic acid nucleotide components. FIG. 50 displays the simulated displacement of DNAs with different base numbers associated with the cfDNA. The data for this graph is based on calculations using double stranded DNA and dNTP diffusion coefficients. The length of the array necessary to remove the majority of dNTPs from the cfDNA (resolution is proportional to $N^{1/2}$, where N is the number of obstacles; the lateral displacement is proportional to N) can be determined by taking into account the differences in diffusional coefficient between the dNTP and the double stranded cell free DNA molecule length. As can be seen in FIG. 50, as the number of obstacles increases, the separation distance between a cell free DNA molecule and the dNTP increases in a linear fashion. For example, an array comprising 4000 obstacles produces a separation distance of ~3,750 μm between the dNTP and cfDNA after traveling through the array. Also shown in FIG. 50 is that the shift in cell free DNA travel due to the obstacles is less when the flow rate is higher. Finally, FIG. 50 shows the shift distance for a cell free DNA molecule gets significantly smaller as the length the DNA molecule gets larger primarily due to the fact that the diffusion coefficient gets smaller for the larger DNA molecules. For DNA molecules containing >100 bases, no shift in the motion is observed irrespective of flow rate.

Example 7—Assembly of Modules to Fluidic Motherboards to Build the uMPS

Figure 51:
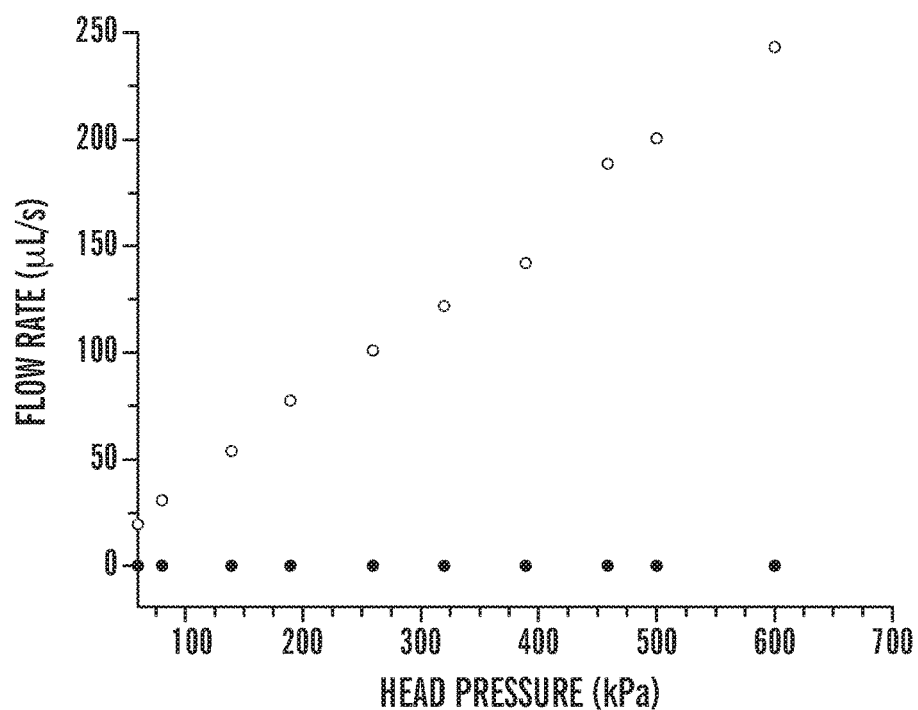
FIG. 51 is a graph showing the volume flow rate versus valve head pressure in a valve of the uMPS.

The valves on the uMPS require a three-layer structure, the cover plate, the fluidic layer and the back cover plate. The valve seats and membrane valves are configured to be on the back side of the fluidic motherboard for the uMPS along with the mechanical solenoids to actuate the valves. Therefore, a unique strategy for producing these thermoplastic valves was employed, which did not only provide higher rates of producing successful valves, but did not require thermal processing for assembly (Jackson et al., *Lab Chip.* 14:106-117 (2014), which is hereby incorporated by reference in its entirety). Laminates coated with a pressure sensitive adhesive are used as the membrane so that no thermal bonding is required. A polyolefin laminate possessing a favorable tensile strength (25-40 mPa), high elongation at break (150-300%), ~100 μm thick, and coated with a silicone acrylate pressure sensitive adhesive (50 μm thick) was utilized. A test device was built by pressure sealing the aforementioned laminate to a thermoplastic microchannel. It was found that one can "deactivate" the adhesive by $UV/O_3$ treatment; the laminate poised directly above the valve seat can be deactivated to prevent the membrane from sticking to the valve seat. This laminate can withstand pressures >600 kPa without failure (FIG. 51), sufficient for the processing steps carried out by the uMPS.

Gasket-less seals: Most microfluidic interconnects rely on direct physical contact between the fluid port and the device being connected. Each contact acts as a passive kinematic constraint on the assembly. If care is not taken, two or more interconnects in conjunction with other assembly features will lead to over-constrained systems and unpredictable dead volumes.

Figure 52:
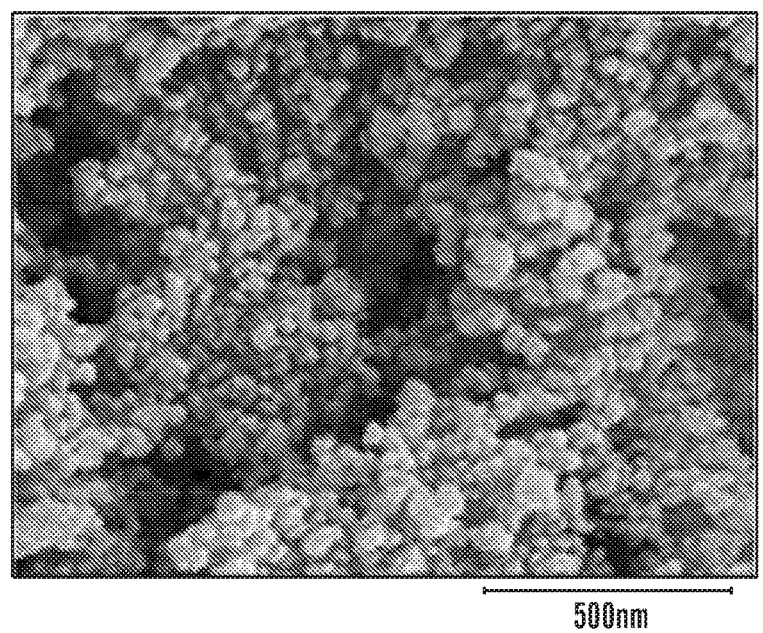
FIG. 52 is a SEM of the super-hydrophobic surface spin coated around the microfluidic through-hole for each gasket-less seal assembly to create the seal.
Figure 53:
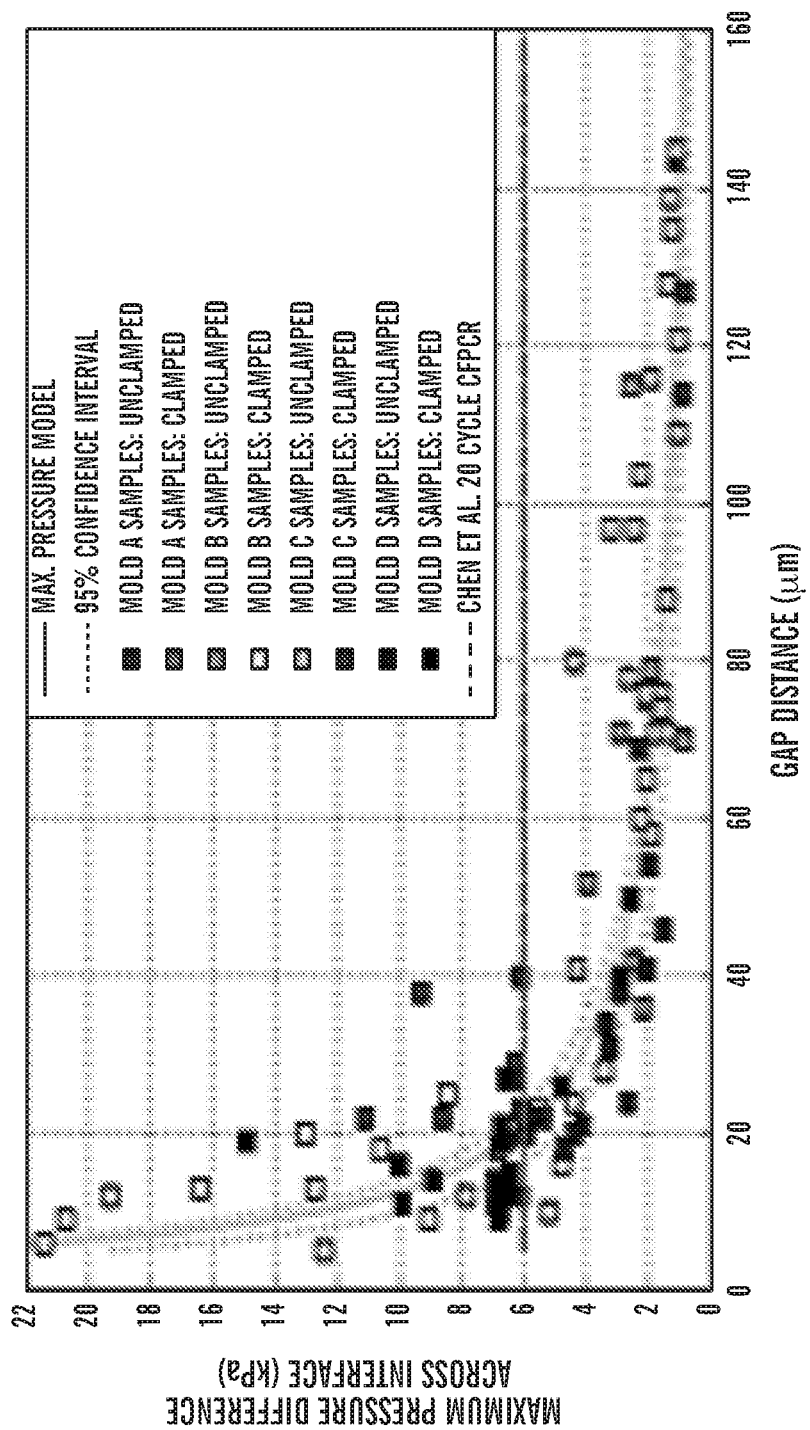
FIG. 53 is a graph showing that the measured maximum pressures the gasket-less seals could withstand were consistent with those estimated using the Young-Laplace equation.

For microfluidic ports with micro-scale gaps between facing surfaces, capillary forces, as defined by the Young-Laplace equation, should resist leakage without any direct physical contact between the facing surfaces, forming a gasket-less seal, see FIG. 33B (Brown, et al., *IMECE* 2012, Nov. 9-15, 2012. ASME, Houston, Tex., pp. IMECE2012-89634 (2012), which is hereby incorporated by reference in its entirety). This concept was tested and it was found that if the facing surfaces are super-hydrophobic (water contact angles >130°), the capillary forces are sufficient to withstand the pressure drop in a typical microfluidic channel. Test parts were created by double-sided injection molding cyclic olefin copolymer parts with microfluidic through holes near an edge to permit observation through a microscope, alignment standards for measuring the relative offset of the mating parts and v-grooves to act as ball bearing seats (see FIG. 28B). Different gaps were created using different diameter precision ceramic ball bearings as the kinematic constraints. Super-hydrophobic surfaces were generated by spin coating the polymer surfaces around the through holes with a commercial coating (see FIG. 52). FIG. 53 is a graph showing that the measured maximum pressures the seals could withstand were consistent with those estimated using the Young-Laplace equation.

Although the invention has been described in detail for the purpose of illustration, it is understood that such details are solely for that purpose and variations can be made therein by those skilled in the art without departing from the spirit and scope of the invention which is defined by the following claims.

What is claimed:
1. A device comprising:
   a biomolecular processor, each biomolecular processor comprising:
      a bioreactor chamber defined by a solid substrate;
      a plurality of spaced support structures within said bioreactor chamber and attached to the solid substrate;
      one or more capture molecules immobilized to some or all of said plurality of spaced support structures, said one or more capture molecules suitable to bind to a portion of a target nucleic acid molecule in a sample;

one or more nanotubes defined by the solid substrate and fluidically coupled to the bioreactor chamber, each of said one or more nanotubes having a passage extending between an input end proximate to said bioreactor chamber and an output end distal to said bioreactor chamber and comprising one or more nanopores within the passage with each nanopore having a reduced diameter relative to the passage; and one or more units defined by the solid substrate and upstream of said biomolecular processor and one or more nanotubes, said one or more units being configured to carry out sample preparation.

2. The device according to claim 1 further comprising:
a separator unit defined by the solid substrate and upstream of said biomolecular processor and one or more nanotubes, said separator unit comprising:
  a separation chamber including solid surfaces defining channels between them with cell specific capture agents attached to the solid surfaces;
  an inlet to the chamber; and
  an outlet from the chamber.

3. The device according to claim 1 further comprising:
a sensor unit defined by the solid substrate and upstream of said biomolecular processor and one or more nanotubes, said sensor unit comprising:
  an inlet;
  an outlet; and
  a cell counter positioned to count cells passing from the inlet to the outlet of said sensor unit.

4. The device according to claim 1 further comprising:
an extractor unit defined by the solid substrate and upstream of said biomolecular processor and one or more nanotubes, said extractor unit comprising solid supports and passages between them, wherein the solid supports are provided with a material suitable to immobilize nucleic acids or exosomes or vesicles.

5. The device according to claim 1 further comprising:
a longitudinally-extending plasma isolation unit defined by the solid substrate and upstream of said biomolecular processor and one or more nanotubes, said longitudinally-extending plasma isolation unit comprising:
  an entrance passage;
  a discharge passage which is wider and shallower than the entrance passage;
  a transition passage connecting the entrance passage and the discharge passage, said transition passage becoming wider and shallower as the transition passages progresses from the entrance passage to the discharge passage;
  primary side channels extending laterally away from the entrance passage, wherein a separator, positioned between the entrance passage and each primary side channel, is sized to permit plasma, but not cells, to pass from the entrance passage to the primary side channels; and
  secondary side channels extending laterally away from the discharge passage, wherein a separator, positioned between the discharge passage and each secondary side channel, is sized to permit plasma, but not cells, to pass from the entrance passage to the secondary side channels.

6. The device according to claim 5 further comprising:
a separator unit defined by the solid substrate, said separator unit comprising:
  a separation chamber including solid surfaces defining channels between them with cell specific capture agents attached to the solid surfaces;
  an inlet to the chamber; and an outlet from the chamber;
a first extractor unit defined by the solid substrate and fluidically coupled to said longitudinally extending plasma isolation unit, said first extractor unit comprising solid supports and passages between them, wherein the solid supports are provided with a material suitable to immobilize nucleic acids or exosomes or vesicles;
a sensor unit defined by the solid substrate and upstream of said biomolecular processor and one or more nanotubes, said sensor unit comprising:
  an inlet;
  an outlet; and
  a cell counter positioned to count cells passing from the inlet to the outlet of said sensor unit; and
a second extractor unit defined by the solid support and fluidically coupled to said sensor unit, said second extractor unit comprising solid supports and passages between them, wherein the solid supports are provided with a material to immobilize nucleic acids;
one or more reactor units defined by the solid substrate and fluidically coupled to said second extractor unit, said one or more reactors comprising a reaction channel with a heater; and
a flow purification unit defined by the solid substrate and fluidically coupled to the one or more reactor units and said biomolecular processor, said flow purification unit comprising:
  a housing defining a chamber,
  one or more inlets connected to the chamber,
  a product outlet connected to the chamber,
  a waste outlet connected to the chamber, and
  a plurality of obstacles positioned within the chamber and oriented to preferentially direct product, in the chamber, to the product outlet and to direct waste, in the chamber, to the waste outlet.

7. A device comprising:
a longitudinally-extending plasma isolation unit defined by a solid substrate, said longitudinally-extending plasma isolation unit comprising:
  an entrance passage;
  a discharge passage which is wider and shallower than the entrance passage;
  a transition passage connecting the entrance passage and the discharge passage, said transition passage becoming wider and shallower as the transition passages progresses from the entrance passage to the discharge passage;
  primary side channels extending laterally away from the entrance passage, wherein a separator, positioned between the entrance passage and each primary side channel, is sized to permit plasma, but not cells, to pass from the entrance passage to the primary side channels; and
  secondary side channels extending laterally away from the discharge passage, wherein a separator, positioned between the discharge passage and each secondary side channel, is sized to permit plasma, but not cells, to pass from the entrance passage to the secondary side channels.

* * * * *

UNITED STATES PATENT AND TRADEMARK OFFICE
CERTIFICATE OF CORRECTION

PATENT NO. : 10,393,726 B2
APPLICATION NO. : 15/560028
DATED : August 27, 2019
INVENTOR(S) : Soper et al.

It is certified that error appears in the above-identified patent and that said Letters Patent is hereby corrected as shown below:

In the Specification

Column 11, Line 10: Please correct "5,000" to read -- ~5,000 --

Column 11, Line 11: Please correct "78,500" to read -- ~78,500 --

Column 15, Line 22: Please correct "2,500" to read -- ~2,500 --

Column 24, Line 55: Please correct "0.24 cm" to read -- ~0.24 cm --

Column 50, Line 12: Please correct "P 31" to read -- $P \approx 31$ --

Column 51, Line 3: Please correct "$\Delta\mu_{app,avg}$" to read -- $\mu_{app,avg}$ --

Column 51, Line 38: Please correct "$d/\Delta_d$" to read -- $d/\lambda_d$ --

Column 51, Line 47: Please correct "$\Delta_D$" to read -- $\lambda_D$ --

Column 53, Line 50: Please correct "(At)" to read -- ($\Delta$t) --

Signed and Sealed this
Twenty-fourth Day of December, 2019

Andrei Iancu
*Director of the United States Patent and Trademark Office*